(12) United States Patent
Grimmond et al.

(10) Patent No.: US 8,765,977 B2
(45) Date of Patent: *Jul. 1, 2014

(54) HYDROXYLATED CONTRAST ENHANCEMENT AGENTS AND IMAGING METHOD

(75) Inventors: Brian James Grimmond, Clifton Park, NY (US); Michael James Rishel, Saratoga Springs, NY (US); Rong Zhang, Niskayuna, NY (US); Jeannette Christine Roberts, Troy, NY (US)

(73) Assignee: General Electric Company, Niskayuna, NY (US)

( * ) Notice: Subject to any disclaimer, the term of this patent is extended or adjusted under 35 U.S.C. 154(b) by 326 days.

This patent is subject to a terminal disclaimer.

(21) Appl. No.: 13/077,746

(22) Filed: Mar. 31, 2011

(65) Prior Publication Data

US 2011/0243858 A1    Oct. 6, 2011

Related U.S. Application Data

(63) Continuation-in-part of application No. 12/956,629, filed on Nov. 30, 2010, and a continuation-in-part of application No. 12/751,286, filed on Mar. 31, 2010, now Pat. No. 8,326,281.

(51) Int. Cl.
    C07D 319/08    (2006.01)
    C07D 309/30    (2006.01)

(52) U.S. Cl.
    USPC ............. 549/365; 549/214; 549/220; 556/19; 556/405

(58) Field of Classification Search
    USPC ............. 424/1.77, 9.1, 9.3, 9.6; 549/214, 365
    See application file for complete search history.

(56) References Cited

U.S. PATENT DOCUMENTS

| | | | |
|---|---|---|---|
| 4,647,447 A | 3/1987 | Gries et al. |
| 4,863,716 A | 9/1989 | Quay et al. |
| 4,880,007 A | 11/1989 | Sadler et al. |
| 4,915,922 A | 4/1990 | Filss |
| 5,039,512 A | 8/1991 | Kraft et al. |
| 5,162,109 A | 11/1992 | Rajagopalan et al. |
| 5,236,695 A | 8/1993 | Winchell et al. |
| 5,409,689 A | 4/1995 | Winchell et al. |
| 5,649,537 A | 7/1997 | Anelli et al. |
| 5,756,688 A | 5/1998 | Snow et al. |
| 5,834,456 A | 11/1998 | Kiefer et al. |
| 5,958,372 A | 9/1999 | Ladd |
| 6,017,522 A | 1/2000 | Butterfield et al. |
| 6,193,749 B1 | 2/2001 | Schroeder et al. |
| 6,509,319 B1 | 1/2003 | Raad et al. |
| 6,652,835 B1 | 11/2003 | Lauffer et al. |
| 7,220,402 B1 | 5/2007 | Andersen et al. |
| 7,988,950 B2 * | 8/2011 | Aime et al. ............... 424/9.365 |
| 2004/0020344 A1 | 2/2004 | Bazala |
| 2005/0232866 A1 | 10/2005 | Melchior et al. |
| 2007/0258905 A1 | 11/2007 | Aime et al. |
| 2009/0317335 A1 | 12/2009 | Lin et al. |

FOREIGN PATENT DOCUMENTS

EP    0275215 B1    4/1992

* cited by examiner

Primary Examiner — Michael G Hartley
Assistant Examiner — Jagadishwar Samala
(74) Attorney, Agent, or Firm — Andrew J. Caruso

(57) ABSTRACT

A method of diagnostic imaging is disclosed comprising administering a medical formulation to a subject, the formulation comprising a contrast enhancement agent having structure I and salts thereof

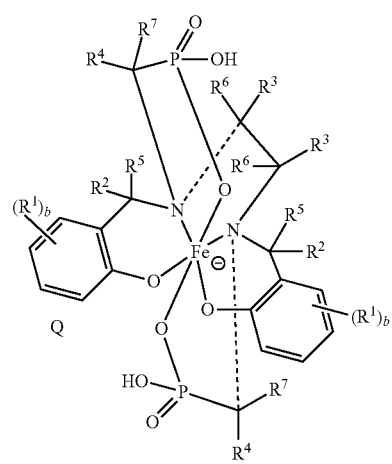

wherein $R^1$ is independently at each occurrence a hydroxy group, a $C_1$-$C_3$ hydroxyalkyl group, or a $C_1$-$C_3$ alkyl group, and b is 0-4; $R^2$-$R^7$ are independently at each occurrence hydrogen, a $C_1$-$C_3$ hydroxyalkyl group, or a $C_1$-$C_3$ alkyl group, with the proviso that at least one of $R^1$-$R^7$ is a hydroxy group or a $C_1$-$C_3$ hydroxyalkyl group; and wherein Q is one or more charge balancing counterions; and one or more pharmaceutically acceptable carriers and excipients. The subject is subjected to a diagnostic imaging technique such as magnetic resonance imaging. The technique may be used in a variety of diagnostic imaging regimes, such as imaging of circulatory systems, genitourinary systems, hepatobiliary systems, central nervous systems, tumors, and abscesses among others.

7 Claims, 5 Drawing Sheets

PRE

POST

HYDROXYLATED CONTRAST ENHANCEMENT AGENTS AND IMAGING METHOD

This application is a Continuation-in-Part of and claims the benefit of U.S. application Ser. No. 12/956,629, filed Nov. 30, 2010 and U.S. application Ser. No. 12/751,286, filed Mar. 31, 2010.

BACK GROUND

This invention relates to the use of contrast enhancement agents in magnetic resonance imaging and to metal chelating ligands and metal chelate compounds useful to such imaging techniques.

Magnetic resonance (MR) imaging has become a critical medical diagnostic tool in human health. The use of MR contrast enhancement agents in MR imaging protocols has proven to be a valuable addition to the technique by improving both the quality of images obtained in an MR imaging procedure and the efficiency with which such images can be gathered. Known MR contrast enhancement agents suffer from a variety of deficiencies. For example, MR contrast enhancement agents containing gadolinium (Gd) chelates, while themselves are not toxic comprise gadolinium ion which in free ionic form is toxic. Contrast enhancement agents comprising chelates of manganese (Mn) may be subject to dissociation of the chelating ligand from the manganese metal center which is undesirable. Various other metal chelates may serve as MR contrast enhancement agents but are frequently less effective than gadolinium chelates and/or are not cleared from the body of the subject at sufficiently high rates following the imaging procedure.

Considerable effort and ingenuity has been expended to reduce the latent toxicity and control bio-distribution of MR contrast enhancement agents comprising gadolinium chelates. Potential MR contrast enhancement agents should exhibit good in-vivo and in-vitro stability, as well as prompt clearance from the body following an MR imaging procedure. MR contrast enhancement agents comprising a paramagnetic iron center are attractive because iron has an extensive and largely innocuous natural biochemistry as compared to gadolinium. This has led to increased interest in the use of iron-based materials as contrast agents for MR imaging.

There exists a need for MR imaging methods employing iron-containing contrast enhancement agents that exhibit performance superior to or equivalent to known contrast enhancement agents while providing one or more additional advantages, such as improved image quality at lower patient dosages, greater patient tolerance and safety when higher doses are required, and improved clearance from the patient following the imaging procedure.

BRIEF DESCRIPTION

In one embodiment, the present invention provides a method of diagnostic imaging comprising: (a) administering a medical formulation to a subject, the formulation comprising a contrast enhancement agent having structure I and salts thereof

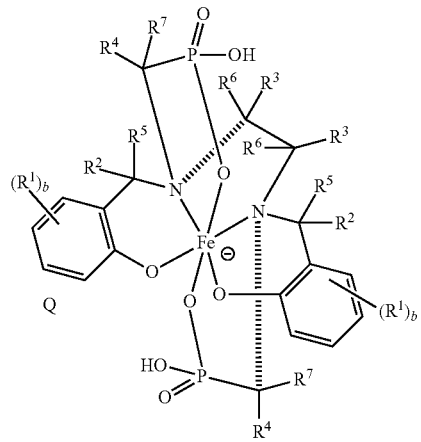

I wherein $R^1$ is independently at each occurrence a hydroxy group, a $C_1$-$C_3$ hydroxyalkyl group, or a $C_1$-$C_3$ alkyl group, and b is 0-4; $R^2$-$R^7$ are independently at each occurrence hydrogen, a $C_1$-$C_3$ hydroxyalkyl group, or a $C_1$-$C_3$ alkyl group, with the proviso that at least one of $R^1$-$R^7$ is a hydroxy group or a $C_1$-$C_3$ hydroxyalkyl group; and wherein Q is one or more charge balancing counterions; and one or more pharmaceutically acceptable carriers and excipients; and (b) subjecting the subject to a diagnostic imaging technique.

In another embodiment, the present invention provides a method of diagnostic imaging comprising: (a) administering a medical formulation to a subject, the formulation comprising a contrast enhancement agent having structure II and salts thereof

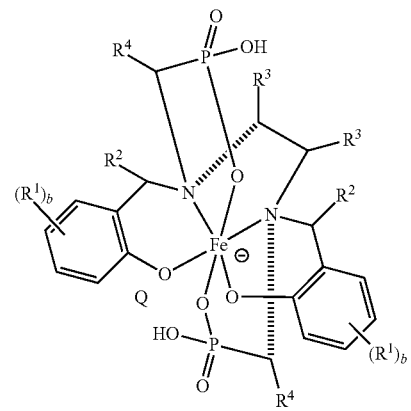

II wherein $R^1$ is independently at each occurrence a hydroxy group, a $C_1$-$C_3$ hydroxyalkyl group, or a $C_1$-$C_3$ alkyl group, and b is 0-4; $R^2$-$R^4$ are hydrogen, a $C_1$-$C_3$ hydroxyalkyl group, or a $C_1$-$C_3$ alkyl group, with the proviso that at least one of $R^1$-$R^4$ is a hydroxy group or $C_1$-$C_3$ hydroxyalkyl group; and wherein Q is one or more charge balancing counterions; and one or more pharmaceutically acceptable carriers and excipients; and (b) subjecting the subject to a diagnostic imaging technique.

In yet another embodiment, the present invention provides a method of diagnostic imaging comprising: (a) administering a medical formulation to a subject, the formulation comprising a contrast enhancement agent having structure FeH-BEDP and salts thereof wherein Q is one or more charge balancing counterions;

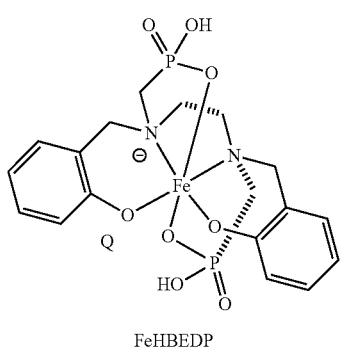

FeHBEDP and one or more pharmaceutically acceptable carriers and excipients; and (b) subjecting the subject to a diagnostic imaging technique.

In yet another embodiment, the present invention comprises the use of a medical formulation comprising a contrast enhancement agent having structure I and salts thereof

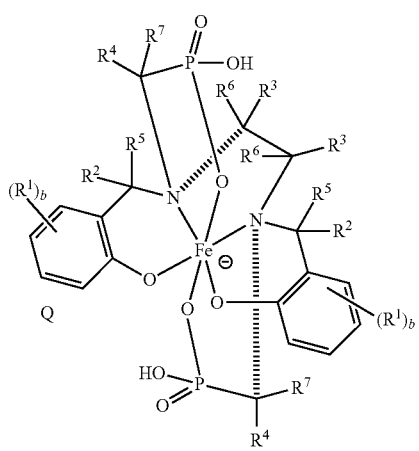

I wherein $R^1$ is independently at each occurrence a hydroxy group, a $C_1$-$C_3$ hydroxyalkyl group, or a $C_1$-$C_3$ alkyl group, and b is 0-4; $R^2$-$R^7$ are independently at each occurrence hydrogen, a $C_1$-$C_3$ hydroxyalkyl group, or a $C_1$-$C_3$ alkyl group, with the proviso that at least one of $R^1$-$R^7$ is a hydroxy group or a $C_1$-$C_3$ hydroxyalkyl group; and wherein Q is one or more charge balancing counterions.

In yet another embodiment, the present invention comprises the use of a medical formulation comprising a contrast enhancement agent having structure II and salts thereof

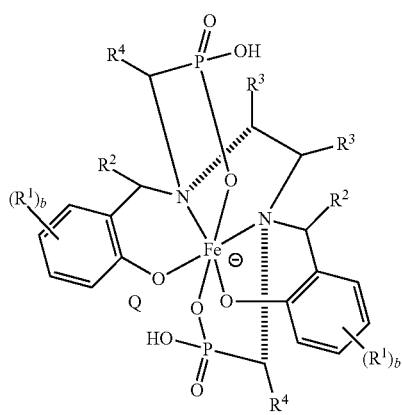

II wherein $R^1$ is independently at each occurrence a hydroxy group, a $C_1$-$C_3$ hydroxyalkyl group, or a $C_1$-$C_3$ alkyl group, and b is 0-4; $R^2$-$R^4$ are hydrogen, a $C_1$-$C_3$ hydroxyalkyl group, or a $C_1$-$C_3$ alkyl group, with the proviso that at least one of $R^1$-$R^4$ is a hydroxy group or $C_1$-$C_3$ hydroxyalkyl group; and wherein Q is one or more charge balancing counterions.

BRIEF DESCRIPTION OF THE DRAWING FIGURES

These and other features, aspects, and advantages of the present invention will become better understood when the following detailed description is read with reference to the accompanying drawings in which like characters represent like parts throughout the drawings, wherein.

DETAILED DESCRIPTION

Figure 1:
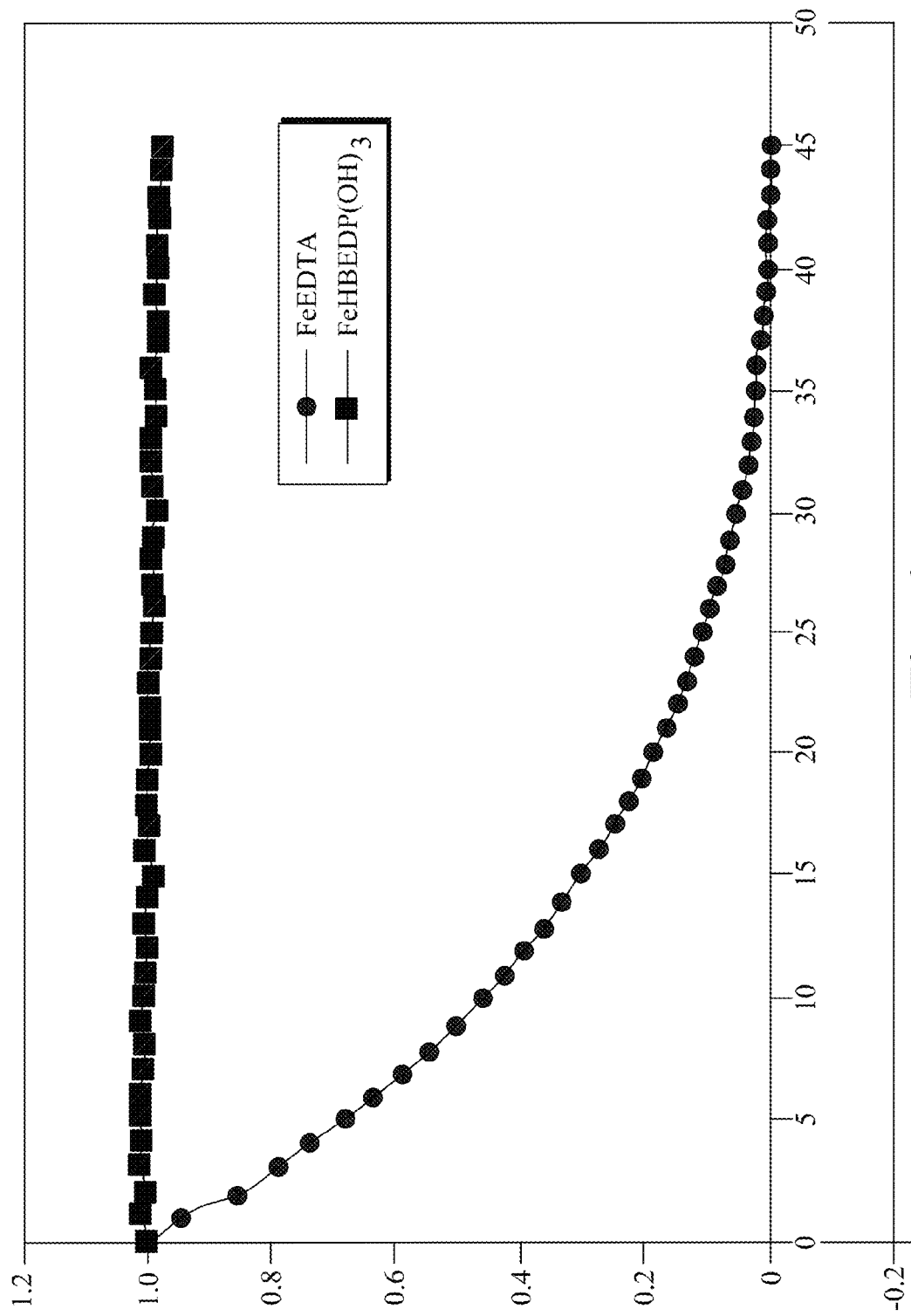
FIG. 1 is a graphical representation of results from an ascorbic acid oxidation assay with different iron chelates (30 mol %[Fe]) in accordance with an embodiment of the invention.

In the following specification and the claims, which follow, reference will be made to a number of terms, which shall be defined to have the following meanings.

The singular forms "a", "an" and "the" include plural referents unless the context clearly dictates otherwise.

"Optional" or "optionally" means that the subsequently described event or circumstance may or may not occur, and that the description includes instances where the event occurs and instances where it does not.

As used herein, the term "solvent" can refer to a single solvent or a mixture of solvents.

Approximating language, as used herein throughout the specification and claims, may be applied to modify any quantitative representation that could permissibly vary without resulting in a change in the basic function to which it is related. Accordingly, a value modified by a term or terms, such as "about", is not to be limited to the precise value specified. In some instances, the approximating language may correspond to the precision of an instrument for measuring the value.

As used herein, the term "aromatic radical" refers to an array of atoms having a valence of at least one comprising at least one aromatic group. The array of atoms having a valence of at least one comprising at least one aromatic group may include heteroatoms such as nitrogen, sulfur, selenium, silicon and oxygen, or may be composed exclusively of carbon and hydrogen. As used herein, the term "aromatic radical" includes but is not limited to phenyl, pyridyl, furanyl, thienyl, naphthyl, phenylene, and biphenyl radicals. As noted, the aromatic radical contains at least one aromatic group. The aromatic group is invariably a cyclic structure having 4n+2 "delocalized" electrons where "n" is an integer equal to 1 or greater, as illustrated by phenyl groups (n=1), thienyl groups (n=1), furanyl groups (n=1), naphthyl groups (n=2), azulenyl groups (n=2), anthraceneyl groups (n=3) and the like. The aromatic radical may also include nonaromatic components. For example, a benzyl group is an aromatic radical which comprises a phenyl ring (the aromatic group) and a methylene group (the nonaromatic component). Similarly a tetrahydronaphthyl radical is an aromatic radical comprising an aromatic group ($C_6H_3$) fused to a nonaromatic component —$(CH_2)_4$—. For convenience, the term "aromatic radical" is defined herein to encompass a wide range of functional groups such as alkyl groups, alkenyl groups, alkynyl groups, haloalkyl groups, haloaromatic groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylphenyl radical is a $C_7$ aromatic radical comprising a methyl group, the methyl group being a functional group which is an alkyl group. Similarly, the 2-nitrophenyl group is a $C_6$ aromatic radical comprising a nitro group, the nitro group being a functional group. Aromatic radicals include halogenated aromatic radicals such as 4-trifluoromethylphenyl, hexafluoro isopropylidenebis(4-phen-1-yloxy) (i.e., —$OPhC(CF_3)_2PhO$—), 4-chloromethylphen-1-yl, 3-trifluorovinyl-2-thienyl, 3-trichloromethylphen-1-yl (i.e., 3-$CCl_3$Ph-), 4-(3-bromoprop-1-yl)phen-1-yl (i.e., 4-$BrCH_2CH_2CH_2$Ph-), and the like. Further examples of aromatic radicals include 4-allyloxyphen-1-oxy, 4-aminophen-1-yl (i.e., 4-$H_2N$Ph-), 3-aminocarbonylphen-1-yl (i.e., $NH_2$COPh-), 4-benzoylphen-1-yl, dicyanomethylidenebis (4-phen-1-yloxy) (i.e., —$OPhC(CN)_2PhO$—), 3-methylphen-1-yl, methylenebis(4-phen-1-yloxy) (i.e., —$OPhCH_2PhO$—), 2-ethylphen-1-yl, phenylethenyl, 3-formyl-2-thienyl, 2-hexyl-5-furanyl, hexamethylene-1,6-bis(4-phen-1-yloxy) (i.e., —$OPh(CH_2)_6PhO$—), 4-hydroxymethylphen-1-yl (i.e., 4-$HOCH_2$Ph-), 4-mercaptomethylphen-1-yl (i.e., 4-$HSCH_2$Ph-), 4-methylthiophen-1-yl (i.e., 4-$CH_3$SPh-), 3-methoxyphen-1-yl, 2-methoxycarbonylphen-1-yloxy (e.g., methyl salicyl), 2-nitromethylphen-1-yl (i.e., 2-$NO_2CH_2$Ph), 3-trimethylsilylphen-1-yl, 4-t-butyldimethylsilylphen-1-yl, 4-vinylphen-1-yl, vinylidenebis (phenyl), and the like. The term "a $C_3$-$C_{10}$ aromatic radical" includes aromatic radicals containing at least three but no more than 10 carbon atoms. The aromatic radical 1-imidazolyl ($C_3H_2N_2$—) represents a $C_3$ aromatic radical. The benzyl radical ($C_7H_7$—) represents a $C_7$ aromatic radical.

As used herein the term "cycloaliphatic radical" refers to a radical having a valence of at least one, and comprising an array of atoms which is cyclic but which is not aromatic. As defined herein a "cycloaliphatic radical" does not contain an aromatic group. A "cycloaliphatic radical" may comprise one or more noncyclic components. For example, a cyclohexylmethyl group ($C_6H_{11}CH_2$—) is a cycloaliphatic radical which comprises a cyclohexyl ring (the array of atoms which is cyclic but which is not aromatic) and a methylene group (the noncyclic component). The cycloaliphatic radical may include heteroatoms such as nitrogen, sulfur, selenium, silicon and oxygen, or may be composed exclusively of carbon and hydrogen. For convenience, the term "cycloaliphatic radical" is defined herein to encompass a wide range of functional groups such as alkyl groups, alkenyl groups, alkynyl groups, haloalkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylcyclopent-1-yl radical is a $C_6$ cycloaliphatic radical comprising a methyl group, the methyl group being a functional group which is an alkyl group. Similarly, the 2-nitrocyclobut-1-yl radical is a $C_4$ cycloaliphatic radical comprising a nitro group, the nitro group being a functional group. A cycloaliphatic radical may comprise one or more halogen atoms which may be the same or different. Halogen atoms include, for example; fluorine, chlorine, bromine, and iodine. Cycloaliphatic radicals comprising one or more halogen atoms include 2-trifluoromethylcyclohex-1-yl, 4-bromodifluoromethylcyclooct-1-yl, 2-chlorodifluoromethylcyclohex-1-yl, hexafluoroisopropylidene-2,2-bis(cyclohex-4-yl) (i.e., —$C_6H_{10}C(CF_3)_2C_6H_{10}$—), 2-chloromethylcyclohex-1-yl, 3-difluoromethylenecyclohex-1-yl, 4-trichloromethylcyclohex-1-yloxy, 4-bromodichloro methylcyclohex-1-ylthio, 2-bromoethylcyclopent-1-yl, 2-bromopropylcyclohex-1-yloxy (e.g., $CH_3$CHBr$CH_2C_6H_{10}$O—), and the like. Further examples of cycloaliphatic radicals include 4-allyloxycyclohex-1-yl, 4-aminocyclohex-1-yl (i.e., $H_2NC_6H_{10}$—), 4-aminocarbonylcyclopent-1-yl (i.e., $NH_2COC_5H_8$—), 4-acetyloxycyclohex-1-yl, 2,2-dicyanoisopropylidenebis(cyclohex-4-yloxy) (i.e., —$OC_6H_{10}C(CN)_2C_6H_{10}O$—), 3-methylcyclohex-1-yl, methylenebis(cyclohex-4-yloxy) (i.e., —$OC_6H_{10}CH_2C_6H_{10}O$—), 1-ethylcyclobut-1-yl, cyclopropylethenyl, 3-formyl-2-terahydrofuranyl, 2-hexyl-5-tetrahydrofuranyl, hexamethylene-1,6-bis(cyclohex-4-yloxy) (i.e., —$OC_6H_{10}(CH_2)_6C_6H_{10}O$—), 4-hydroxymethylcyclohex-1-yl (i.e., 4-$HOCH_2C_6H_{10}$—), 4-mercaptomethylcyclohex-1-yl (i.e., 4-$HSCH_2C_6H_{10}$—), 4-methylthiocyclohex-1-yl (i.e., 4-$CH_3SC_6H_{10}$—), 4-methoxycyclohex-1-yl, 2-methoxycarbonylcyclohex-1-yloxy (2-$CH_3OCOC_6H_{10}O$—), 4-nitromethylcyclohex-1-yl (i.e., $NO_2CH_2C_6H_{10}$—), 3-trimethylsilylcyclohex-1-yl, 2-t-butyldimethylsilylcyclopent-1-yl, 4-trimethoxysilylethylcyclohex-1-yl (e.g., ($CH_3O)_3SiCH_2CH_2C_6H_{10}$—), 4-vinylcyclohexen-1-yl, vinylidenebis (cyclohexyl), and the like. The term "a $C_3$-$C_{10}$ cycloaliphatic radical" includes cycloaliphatic radicals containing at least three but no more than 10 carbon atoms. The cycloaliphatic radical 2-tetrahydrofuranyl ($C_4H_7O$—) represents a $C_4$ cycloaliphatic radical. The cyclohexylmethyl radical ($C_6H_{11}CH_2$—) represents a $C_7$ cycloaliphatic radical.

As used herein the term "aliphatic radical" refers to an organic radical having a valence of at least one consisting of a linear or branched array of atoms which is not cyclic. Aliphatic radicals are defined to comprise at least one carbon atom. The array of atoms comprising the aliphatic radical may include heteroatoms such as nitrogen, sulfur, silicon, selenium and oxygen or may be composed exclusively of carbon and hydrogen. For convenience, the term "aliphatic radical" is defined herein to encompass, as part of the "linear or branched array of atoms which is not cyclic" a wide range of functional groups such as alkyl groups, alkenyl groups, alkynyl groups, haloalkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylpent-1-yl radical is a $C_6$ aliphatic radical comprising a methyl group, the methyl group being a functional group which is an alkyl group. Similarly, the 4-nitrobut-1-yl group is a $C_4$ aliphatic radical comprising a nitro group, the nitro group being a functional group. An aliphatic radical may be a haloalkyl group which comprises one or more halogen atoms which may be the same or different. Halogen atoms include, for example; fluorine, chlorine, bromine, and iodine. Aliphatic radicals comprising one or more halogen atoms include the alkyl halides trifluoromethyl, bromodifluoromethyl, chlorodifluoromethyl, hexafluoroisopropylidene, chloromethyl, difluorovinylidene, trichloromethyl, bromodichloromethyl, bromoethyl, 2-bromotrimethylene (e.g., $-CH_2CHBrCH_2-$), and the like. Further examples of aliphatic radicals include allyl, aminocarbonyl (i.e., $-CONH_2$), carbonyl, 2,2-dicyanoisopropylidene (i.e., $-CH_2C(CN)_2CH_2-$), methyl (i.e., $-CH_3$), methylene (i.e., $-CH_2-$), ethyl, ethylene, formyl (i.e., $-CHO$), hexyl, hexamethylene, hydroxymethyl (i.e., $-CH_2OH$), mercaptomethyl (i.e., $-CH_2SH$), methylthio (i.e., $-SCH_3$), methylthiomethyl (i.e., $-CH_2SCH_3$), methoxy, methoxycarbonyl (i.e., $CH_3OCO-$), nitromethyl (i.e., $-CH_2NO_2$), thiocarbonyl, trimethylsilyl (i.e., $(CH_3)_3Si-$), t-butyldimethylsilyl, 3-trimethyoxysilylpropyl (i.e., $(CH_3O)_3SiCH_2CH_2CH_2-$), vinyl, vinylidene, and the like. By way of further example, a $C_1$-$C_{10}$ aliphatic radical contains at least one but no more than 10 carbon atoms. A methyl group (i.e., $CH_3-$) is an example of a $C_1$ aliphatic radical. A decyl group (i.e., $CH_3(CH_2)_9-$) is an example of a $C_{10}$ aliphatic radical.

As noted, in one embodiment, the present invention provides a method of diagnostic imaging comprising: (a) administering a medical formulation to a subject, the formulation comprising a contrast enhancement agent having structure I and salts thereof

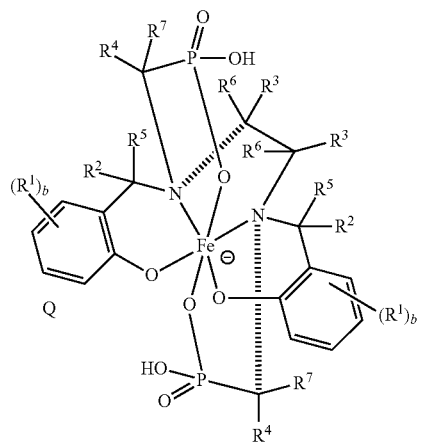

wherein $R^1$ is independently at each occurrence a hydroxy group, a $C_1$-$C_3$ hydroxyalkyl group, or a $C_1$-$C_3$ alkyl group, and b is 0-4; $R^2$-$R^7$ are independently at each occurrence hydrogen, a $C_1$-$C_3$ hydroxyalkyl group, or a $C_1$-$C_3$ alkyl group, with the proviso that at least one of $R^1$-$R^7$ is a hydroxy group or a $C_1$-$C_3$ hydroxyalkyl group; and wherein Q is one or more charge balancing counterions; and one or more pharmaceutically acceptable carriers and excipients; and (b) subjecting the subject to a diagnostic imaging technique.

As used herein, the expression, "and salts thereof" following a numbered chemical structure indicates that the structure as drawn may represent salts of that structure in addition to the structure itself. For example, "an iron chelate having structure I and salts thereof" should be read to mean structure I and salts of structure I. For example, when applied to structure I the expression "and salts thereof" herein is intended to include the structure identified as I (salt) wherein the phosphonic acid moieties are shown as ionized

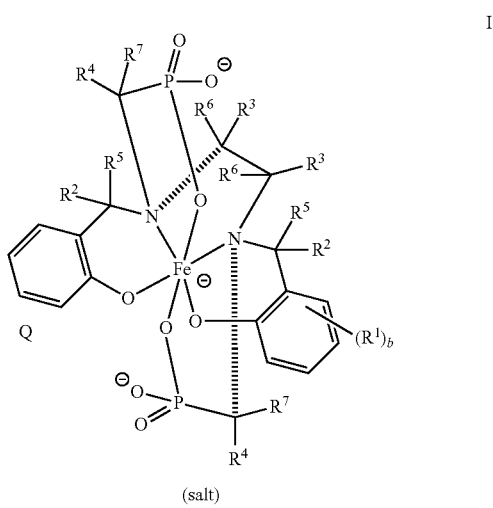

(salt)

(i.e. negatively charged) and Q represents one or more charge balancing counterions, for example three sodium ions. Additional examples of this principle of inclusiveness are given at various points in this disclosure, for example in Table 1 (Iron Chelates 1f-1i), Table 2 (Iron Chelates 2f-2i), Table 3 (Ligands 3e-3f), Table 4 (Ligands 4f-4i) and Table 5 (Ligand Precursors 5e-5g). Thus, in claims presented herein, "a contrast enhancement agent comprising an iron chelate having structure I and salts thereof" is in one distinct embodiment a contrast enhancement agent comprising a iron chelate having structure I; in an alternate distinct embodiment, a contrast enhancement agent comprising one or more salts of an iron chelate having structure I; and in yet another distinct embodiment, a contrast enhancement agent comprising a mixture of an iron chelate having structure I together with one or more salts of an iron chelate having structure I. Similarly a claim reciting "a medical formulation comprising a contrast enhancement agent having structure I and salts thereof" is in one distinct embodiment a medical formulation comprising structure I; in an alternate and distinct embodiment, a medical formulation comprising one or more salts of structure I; and in yet another distinct embodiment, a medical formulation comprising a mixture of structure I together with one or more salts of structure I. Those of ordinary skill in the art, however, taking note of the tendency of phosphonic acids to ionize and the ubiquity of counterions such as sodium cations, will understand that to some degree most compositions represented by structure I will be mixtures of related chemical species at least some of which will qualify as salts of structure I (i.e. salts thereof).

Although throughout this disclosure there is considerable focus on human health, the contrast enhancement agents used according to the method of the present invention are useful in the study and treatment of variety of human and animal diseases as imaging agents, and as probes for the development of imaging agents. Thus, the term "subject" may refer to a human subject or a non-human subject, for example pets (dogs cats) and livestock. Moreover, the term subject may also refer to an inanimate object from which diagnostic imaging information is desired. (See for example the example presented herein.)

Contrast enhancement agents comprising an iron chelate and falling within generic structure I and salts thereof are illustrated in Table 1 below

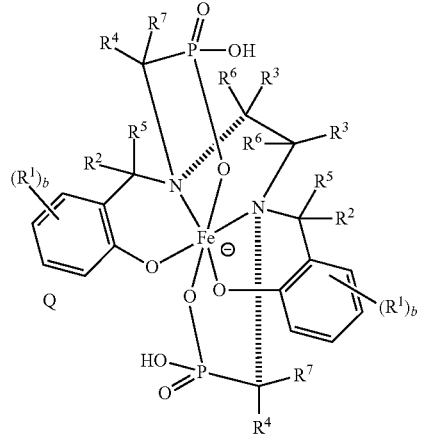

I

TABLE 1

Examples of Iron Chelate Contrast Enhancement Agents Having Structure I And Salts Thereof

| Entry | Structure | Variables $R^1$-$R^7$ Defined As | Variable Q Defined As |
|---|---|---|---|
| 1a | 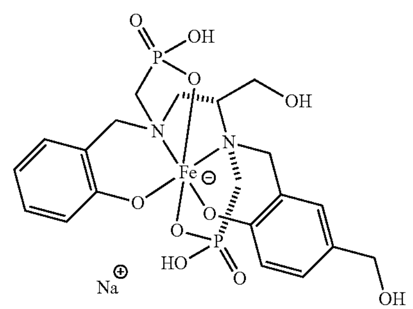 | $R^1$ is hydroxymethyl; $R^2$-$R^5$ are hydrogen; $R^6$ is hydroxymethyl and hydrogen; $R^7$ is hydrogen; b is 0 and 1. | $Na^+$ |
| 1b | 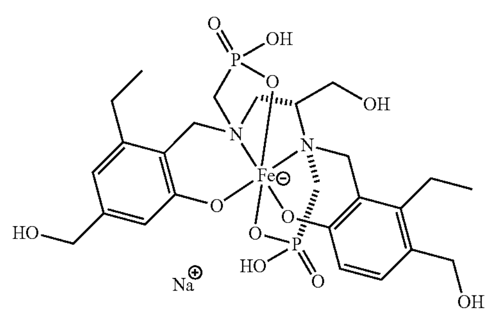 | $R^1$ is hydroxymethyl and ethyl; $R^2$-$R^5$ are hydrogen; $R^6$ is hydroxymethyl and hydrogen; $R^7$ is hydrogen; b is 2. | $Na^+$ |
| 1c | 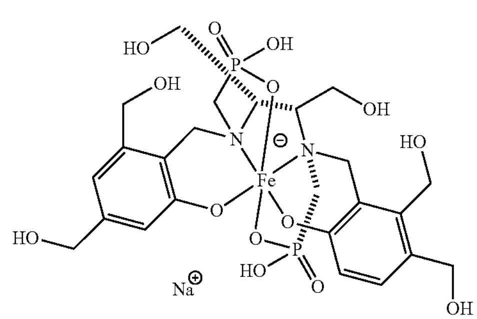 | $R^1$ is hydroxymethyl; $R^2$-$R^5$ are hydrogen, $R^6$ is hydroxymethyl; $R^7$ is hydrogen; b is 2. | $Na^+$ |

TABLE 1-continued

Examples of Iron Chelate Contrast Enhancement Agents Having Structure I And Salts Thereof

| Entry | Structure | Variables $R^1$-$R^7$ Defined As | Variable Q Defined As |
|---|---|---|---|
| 1d | 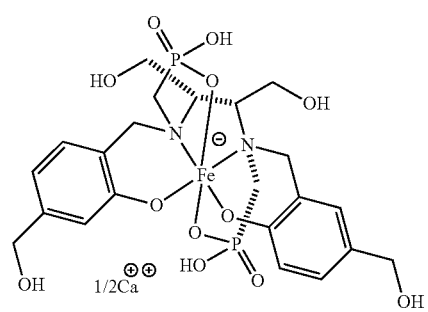 | $R^1$ is hydroxymethyl; $R^2$-$R^5$ are hydrogen; $R^6$ is hydroxymethyl; $R^7$ is hydrogen; b is 1. | ½ Ca$^{++}$ |
| 1e | 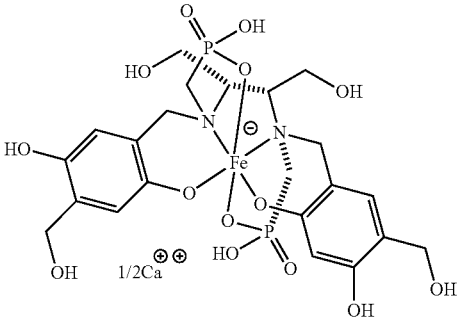 | $R^1$ is hydroxy and hydroxymethyl; $R^2$-$R^5$ are hydrogen; $R^6$ is hydroxymethyl; $R^7$ is hydrogen; b is 2. | ½ Ca$^{++}$ |
| 1f | 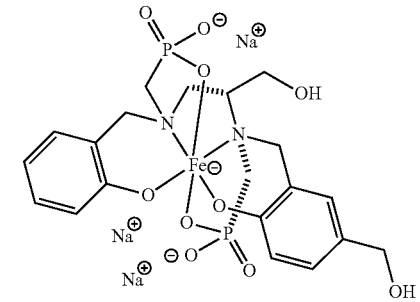 | $R^1$ is hydroxymethyl; $R^2$-$R^5$ are hydrogen; $R^6$ is hydroxymethyl and hydrogen; $R^7$ is hydrogen; b is 0 and 1. | 3 Na$^+$ |
| 1g | 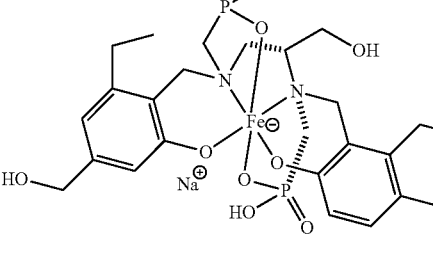 | $R^1$ is hydroxymethyl and ethyl; $R^2$-$R^5$ are hydrogen; $R^6$ is hydroxymethyl and hydrogen; $R^7$ is hydrogen; b is 2. | triethylammonium, Na$^+$ |

TABLE 1-continued

Examples of Iron Chelate Contrast Enhancement Agents Having Structure I And Salts Thereof

| Entry | Structure | Variables $R^1$-$R^7$ Defined As | Variable Q Defined As |
|---|---|---|---|
| 1h | 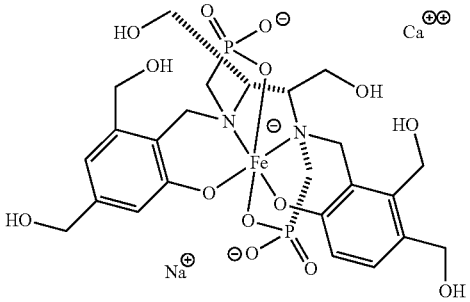 | $R^1$ is hydroxymethyl; $R^2$-$R^5$ are hydrogen, $R^6$ is hydroxymethyl; $R^7$ is hydrogen; b is 2. | $Na^+$, $Ca^{++}$ |
| 1i | 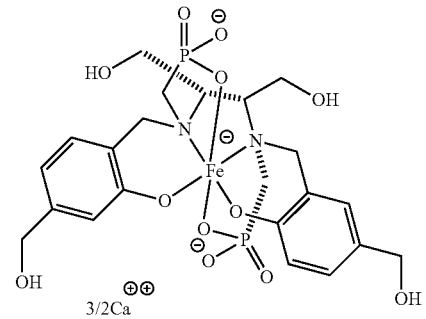 | $R^1$ is hydroxymethyl; $R^2$-$R^5$ are hydrogen; $R^6$ is hydroxymethyl; $R^7$ is hydrogen; b is 1. | ½ $Ca^{++}$ |

In general, and throughout this disclosure, no absolute or relative stereochemistry is intended to be shown for a structure, as in for example structures I and II, and the structures are intended to encompass all possible absolute and relative stereochemical configurations, unless specified otherwise. Thus, structure I depicts an iron chelate compound in which no absolute or relative stereochemistry is intended to be shown. As such, structure I is intended to represent a genus of iron chelate compounds which includes racemic compounds, single enantiomers, enantiomerically enriched compositions and mixtures of diastereomers. In one embodiment, the present invention comprises the use of a contrast enhancement agent having structure 1a (Table 1) which is a racemic mixture having equal concentrations of levorotatory and dextrorotatory enantiomers of contrast enhancement agent 1a. In an alternate embodiment, the present invention comprises the use of a contrast enhancement agent having structure 1b (Table 1) which is an enantiomerically enriched mixture having unequal concentrations of levorotatory and dextrorotatory enantiomers of 1b. In yet another embodiment, the present invention comprises the use of a contrast enhancement agent having structure 1c (Table 1) which is a diastereomeric mixture comprising at least two compounds having structure 1c which are not enantiomers.

Those skilled in the art will appreciate that the iron chelate compositions used according to the method of the present invention may comprise a principal component enantiomer, a minor component enantiomer, and additional diastereomeric iron chelate components. In one embodiment, the present invention comprises the use of an iron chelate composition comprising a principal component enantiomer and related diastereomers. In an alternate embodiment, the present invention comprises the use of an iron chelate composition having no principal component enantiomer and which is a diastereomeric mixture.

In another embodiment, the present invention comprises the use of a contrast enhancement agent comprising an iron chelate having structure II and salts thereof

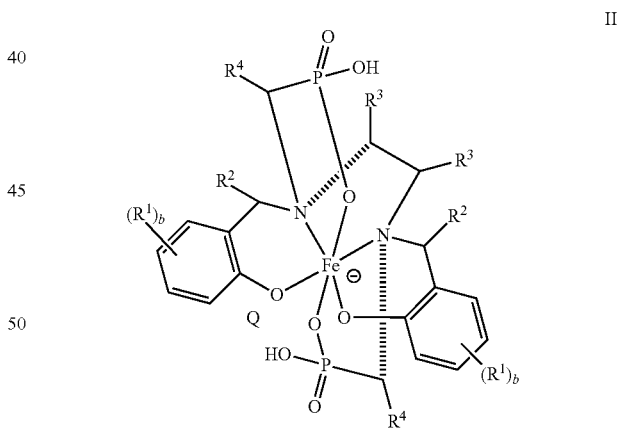

wherein $R^1$ is independently at each occurrence a hydroxy group, a $C_1$-$C_3$ hydroxyalkyl group, or a $C_1$-$C_3$ alkyl group, and b is 0-4; $R^2$-$R^4$ are hydrogen, a $C_1$-$C_3$ hydroxyalkyl group, or a $C_1$-$C_3$ alkyl group, with the proviso that at least one of $R^1$-$R^4$ is a hydroxy group or a $C_1$-$C_3$ hydroxyalkyl group; and wherein Q is one or more charge balancing counterions.

Contrast enhancement agents comprising an iron chelate and falling within generic structure II and salts thereof are illustrated in Table 2 below.

TABLE 2

Examples of Iron Chelate Contrast Enhancement Agents Having Structure II And Salts Thereof

| Entry | Structure | Variables $R^1$-$R^4$ Defined As | Variable Q Defined As |
|---|---|---|---|
| 2a | (structure) | $R^1$ is methyl and hydroxymethyl; $R^2$ and $R^4$ are hydrogen; $R^3$ is hydroxymethyl and hydrogen; b is 1. | $Na^+$ |
| 2b | (structure) | $R^1$ is hydroxymethyl and ethyl; $R^2$-$R^3$ are hydrogen; $R^4$ is hydroxymethyl and hydrogen; b is 2. | $Na^+$ |
| 2c | (structure) | $R^1$ is hydroxymethyl; $R^2$ and $R^4$ are hydrogen; $R^3$ is hydroxymethyl; b is 2. | $Na^+$ |
| 2d | (structure) | $R^1$ is hydroxymethyl; $R^2$-$R^3$ are hydrogen; $R^4$ is methyl and ethyl; b is 1. | ½ $Ca^{++}$ |

TABLE 2-continued

Examples of Iron Chelate Contrast Enhancement Agents Having Structure II And Salts Thereof

| Entry | Structure | Variables $R^1$-$R^4$ Defined As | Variable Q Defined As |
|---|---|---|---|
| 2e | 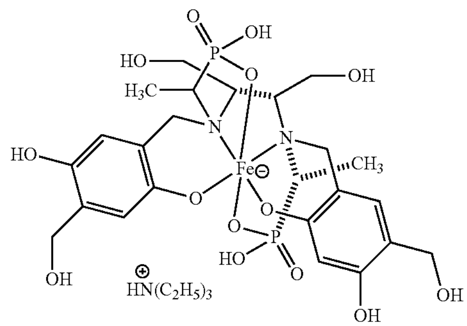 | $R^1$ is hydroxy and hydroxymethyl; $R^2$ is hydrogen; $R^3$ is hydroxymethyl; $R^4$ is methyl; b is 2. | $^+HN(C_2H_5)_3$ |
| 2f | 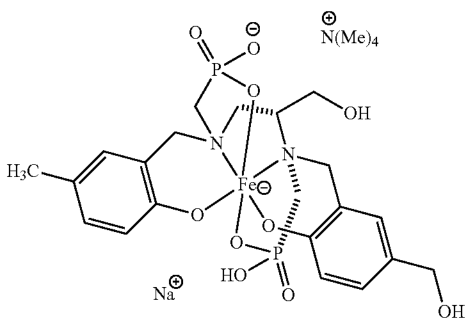 | $R^1$ is methyl and hydroxymethyl; $R^2$ and $R^4$ are hydrogen; $R^3$ is hydroxymethyl and hydrogen; b is 1. | $Na^+$, $N^+(Me)_4$ |
| 2g | 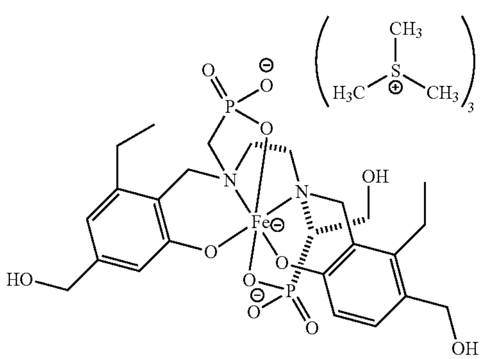 | $R^1$ is hydroxymethyl and ethyl; $R^2$-$R^3$ are hydrogen; $R^4$ is hydroxymethyl and hydrogen; b is 2. | 3 $H_3C-\overset{CH_3}{\underset{\oplus}{S}}-CH_3$ |
| 2h | 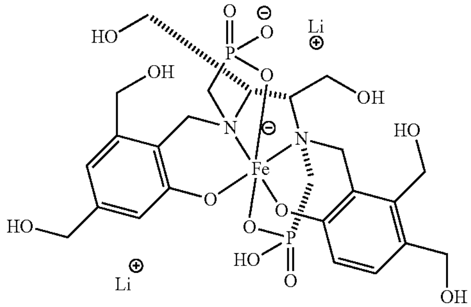 | $R^1$ is hydroxymethyl; $R^2$ and $R^4$ are hydrogen; $R^3$ is hydroxymethyl; b is 2. | 2 $Li^+$ |

TABLE 2-continued

Examples of Iron Chelate Contrast Enhancement Agents Having Structure II And Salts Thereof

| Entry | Structure | Variables $R^1$-$R^4$ Defined As | Variable Q Defined As |
|---|---|---|---|
| 2i | 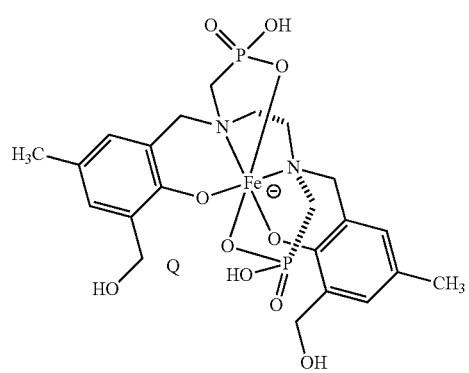 | $R^1$ is hydroxymethyl; $R^2$-$R^3$ are hydrogen; $R^4$ is methyl and ethyl; b is 1. | 1/2 $Ca^{++}$, $(Bu)_4N^+$ |

The one or more charge balancing counterions Q may be an organic cation or an inorganic cation, or a mixture of organic and inorganic cations (See Table 1, Entry 1g and Table 2, Entry 2l). Thus, in one embodiment, the charge balancing counterion Q is an inorganic cation. Non-limiting examples of inorganic cations include alkali metal cations, alkaline earth metal cations, transition metal cations, and inorganic ammonium cations ($NH_4^+$). In another embodiment, the charge balancing counterion Q is an organic cation, for example an organic ammonium cation, an organic phosphonium cation, an organic sulfonium cation, or a mixture thereof. In one embodiment, the charge balancing counterion is the ammonium salt of an amino sugar such as the 2-(N,N,N-trimethylammonium)-2-deoxyglucose. In one embodiment, the charge balancing counterion is the protonated form of N-methyl glucamine.

In one embodiment, the contrast enhancing agent used according to the method of the present invention includes an iron chelate having structure III and salts thereof

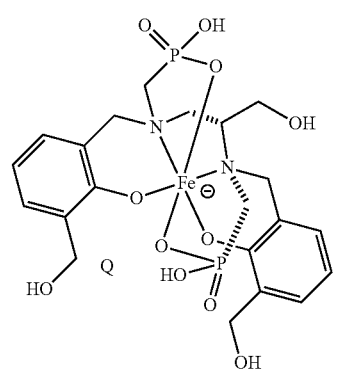

III wherein Q is one or more charge balancing counterions.

In another embodiment, the contrast enhancing agent used according to the method of the present invention includes an iron chelate having structure IV and salts thereof

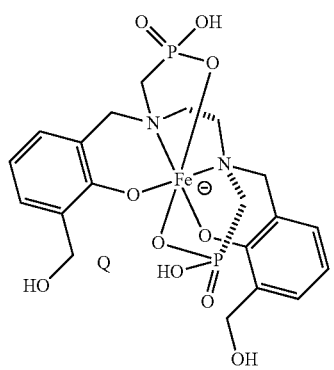

IV wherein Q is one or more charge balancing counterions.

In another embodiment, the contrast enhancing agent used according to the method of the present invention includes an iron chelate having structure V and salts thereof

V wherein Q is one or more charge balancing counterions.

In yet another embodiment, the contrast enhancing agent used according to the method of the present invention includes an iron chelate having structure VI and salts thereof

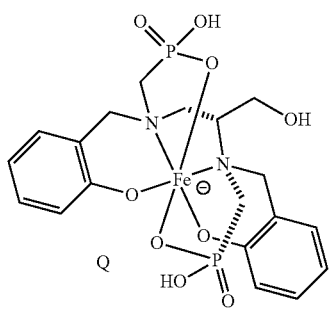

VI wherein Q is one or more charge balancing counterions.

In another embodiment, the contrast enhancing agent used according to the method of the present invention includes an iron chelate having structure VII and salts thereof

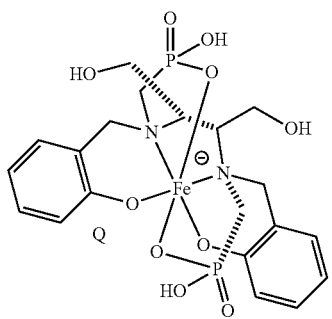

VII wherein Q is one or more charge balancing counterions.

In yet another embodiment, the contrast enhancing agent used according to the method of the present invention includes an iron chelate having structure VIII and salts thereof

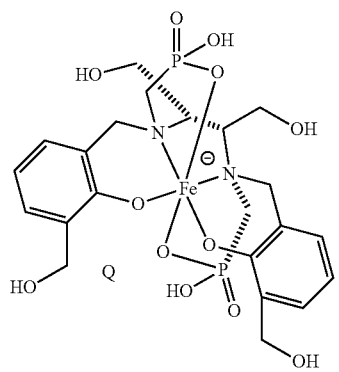

VIII wherein Q is one or more charge balancing counterions.

In one embodiment, the contrast enhancement agent used according to the method of the present invention is prepared from a metal chelating ligand having idealized structure IX and salts thereof,

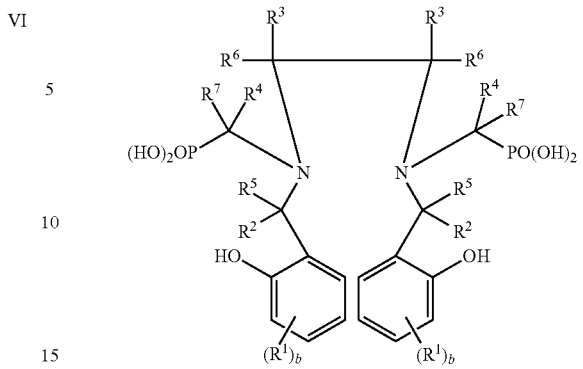

IX wherein $R^1$ is independently at each occurrence a hydroxy group, a $C_1$-$C_3$ hydroxyalkyl group, or a $C_1$-$C_3$ alkyl group, and b is 0-4; $R^2$-$R^7$ are independently at each occurrence hydrogen, a $C_1$-$C_3$ hydroxyalkyl group, or a $C_1$-$C_3$ alkyl group, with the proviso that at least one of $R^1$-$R^7$ is a hydroxy group or a $C_1$-$C_3$ hydroxyalkyl group.

The term "idealized structure" is used herein to designate the structure indicated and additional structures which may include protonated and deprotonated forms of the metal chelating ligand having the idealized structure and may also include charge balancing counterions. Those having ordinary skill in the art will appreciate that the individual metal chelating ligands used to prepare the contrast enhancement agents used according to the method of the present invention may comprise protonated and deprotonated forms of the metal chelating ligand, for example the idealized structure of metal chelating ligand of structure IX comprises one or more of the protonated and the deprotonated forms having structure X-XII

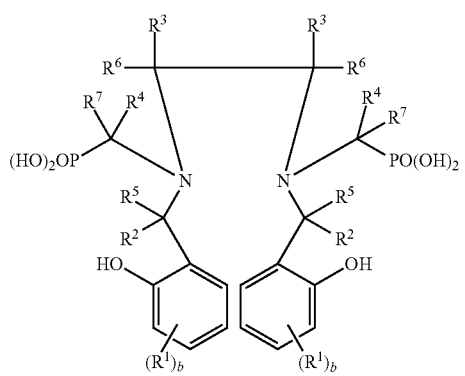

IX

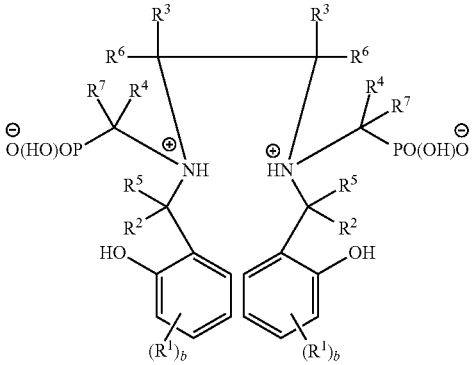

X

-continued

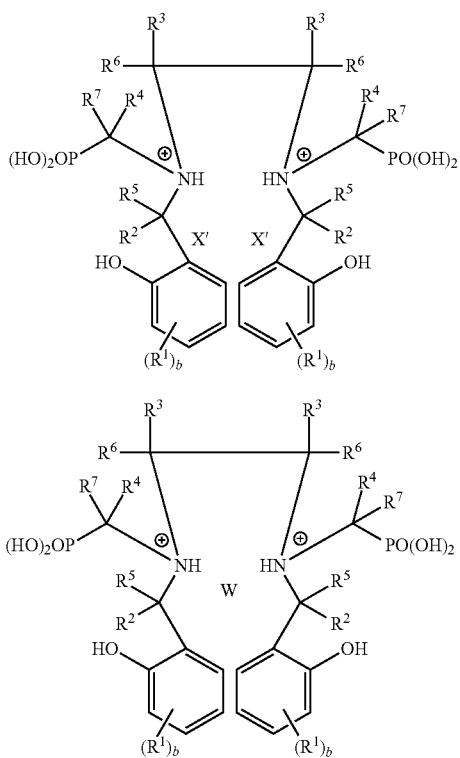

XI

XII wherein W and X' are charge balancing counterions which are anions. Entries 3e and 3f illustrate salts of ligand IX which comprise charge balancing counterions which are cations. In one embodiment, the charge balancing counterion X' may be an inorganic anion or an organic anion. Similarly, W may be an inorganic anion or an organic anion. Thus, in one embodiment, the charge balancing counterion W is an inorganic anion. In another embodiment, the charge balancing counterion W is an organic anion. Similarly, in one embodiment, the charge balancing counterion X' is an inorganic anion. In another embodiment, the charge balancing counterion X' is an organic anion. Those skilled in the art will appreciate that charge balancing counterions X' include monovalent anions such as chloride, bromide, iodide, bicarbonate, acetate, glycinate, ammonium succinate, and the like. Similarly, those skilled in the art will appreciate that charge balancing counterions W include polyvalent anions such as carbonate, sulfate, succinate, malonate, and the like.

Metal chelating ligands having idealized structure IX and salts thereof are further illustrated in Table 3 below.

TABLE 3

Examples of Metal Chelating Ligands Having Structure IX and Salts Thereof

| Entry | Structure | Variables $R^1$-$R^7$ Defined As | W | X' |
|---|---|---|---|---|
| 3a | 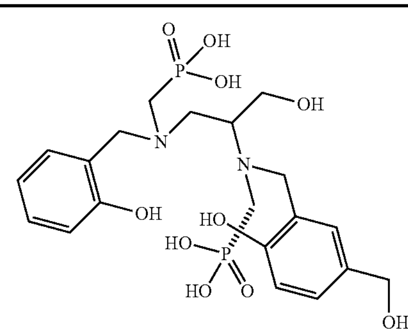 | $R^1$ is hydroxymethyl; $R^2$-$R^5$ are hydrogen; $R^6$ is hydroxymethyl and hydrogen; $R^7$ is hydrogen; b is 0 and 1. | — | — |
| 3b | 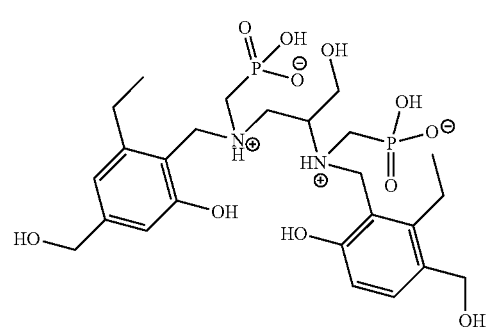 [SMILES: CCc1cc(CO)cc(O)c1C[NH+](CC(CO)[NH+](Cc1c(O)ccc(CO)c1CC)CP(=O)([O-])O)CP(=O)([O-])O] | $R^1$ is hydroxymethyl and ethyl; $R^2$-$R^5$ are hydrogen; $R^6$ is hydroxymethyl and hydrogen; $R^7$ is hydrogen; b is 2. | — | — |

TABLE 3-continued

Examples of Metal Chelating Ligands Having Structure IX and Salts Thereof

| Entry | Structure | Variables $R^1$-$R^7$ Defined As | W | X' |
|---|---|---|---|---|
| 3c | 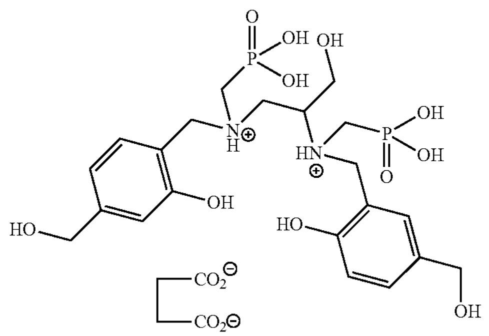 | $R^1$ is hydroxymethyl; $R^2$-$R^5$ are hydrogen; $R^6$ is hydroxymethyl and hydrogen; $R^7$ is hydrogen; b is 1. | —$CO_2^\ominus$ —$CO_2^\ominus$ (succinate) | — |
| 3d | 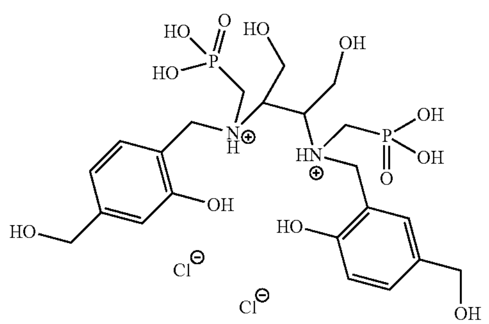 [SMILES: O=P(O)(O)C[NH+](Cc1ccc(CO)cc1O)C(CO)C(CO)[NH+](Cc1cc(CO)ccc1O)CP(=O)(O)O ; [Cl-] ; [Cl-]] | $R^1$ is hydroxymethyl; $R^2$-$R^5$ are hydrogen; $R^6$ is hydroxymethyl; $R^7$ is hydrogen; b is 1. | — | Cl⁻ |
| 3e | 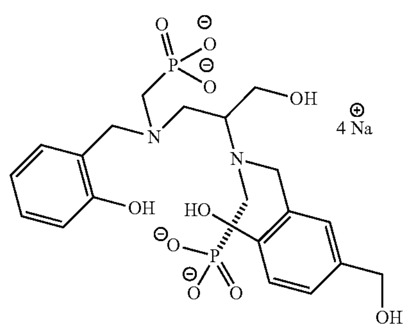 | $R^1$ is hydroxymethyl; $R^2$-$R^5$ are hydrogen; $R^6$ is hydroxymethyl and hydrogen; $R^7$ is hydrogen; b is 0 and 1. | — | — |
| 3f | 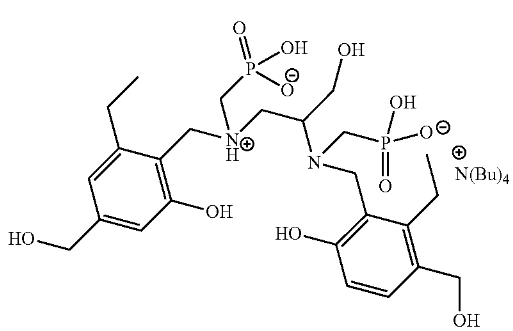 [SMILES: CCc1cc(CO)cc(O)c1C[NH+](CC(CO)N(Cc1c(O)ccc(CO)c1CC)CP(=O)([O-])O)CP(=O)([O-])O] | $R^1$ is hydroxymethyl and ethyl; $R^2$-$R^5$ are hydrogen; $R^6$ is hydroxymethyl and hydrogen; $R^7$ is hydrogen; b is 2. | — | — |

In an alternate embodiment, the contrast enhancement agents used according to the method of the present invention may be prepared from a metal chelating ligand having an idealized structure XIII and salts thereof

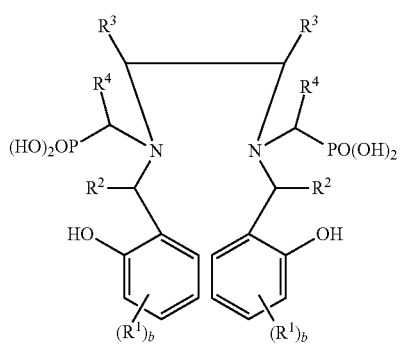

XIII wherein $R^1$ is independently at each occurrence a hydroxy group, a $C_1$-$C_3$ hydroxyalkyl group, or a $C_1$-$C_3$ alkyl group, and b is 0-4; and $R^2$-$R^4$ are hydrogen, a $C_1$-$C_3$ hydroxyalkyl group, or a $C_1$-$C_3$ alkyl group, with the proviso that at least one of $R^1$-$R^4$ is a hydroxy group or $C_1$-$C_3$ hydroxyalkyl group.

The metal chelating ligands having structure XIII and salts thereof are illustrated in Table 4 below.

TABLE 4

Examples of Metal Chelating Ligands Having Structure XIII And Salts Thereof

| Entry | Structure | Variables $R^1$-$R^4$ Defined As | W | X' |
|---|---|---|---|---|
| 4a | 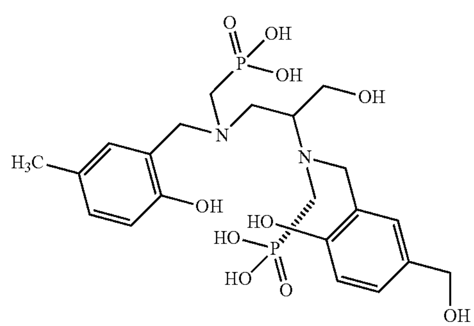 | $R^1$ is methyl and hydroxymethyl; $R^2$ and $R^4$ are hydrogen; $R^3$ is hydroxymethyl and hydrogen; b is 1. | — | — |
| 4b | 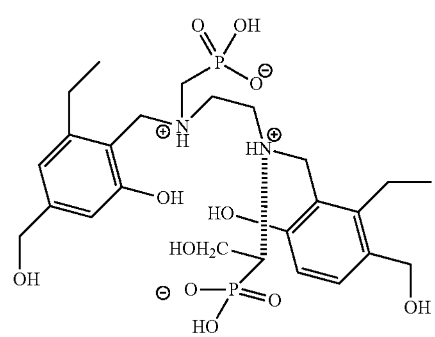 [SMILES: CCc1cc(CO)cc(O)c1C[NH+](CC[N@H+](Cc1c(O)ccc(CO)c1CC)C(CO)P(=O)([O-])O)CP(=O)([O-])O] | $R^1$ is hydroxymethyl and ethyl; $R^2$-$R^3$ are hydrogen; $R^4$ is hydroxymethyl and hydrogen; b is 2. | — | — |
| 4c | 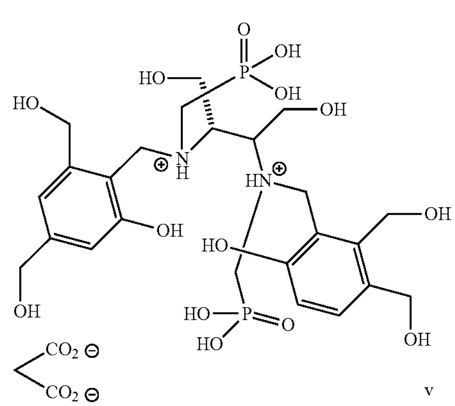 | $R^1$ is hydroxymethyl; $R^2$ and $R^4$ are hydrogen; $R^3$ is hydroxymethyl; b is 2. | $\overset{\ominus}{\phantom{.}}CO_2$ $\phantom{..}CO_2^{\ominus}$ (malonate) | — |

TABLE 4-continued

Examples of Metal Chelating Ligands Having Structure XIII And Salts Thereof

| Entry | Structure | Variables $R^1$-$R^4$ Defined As | W | X' |
|---|---|---|---|---|
| 4d | 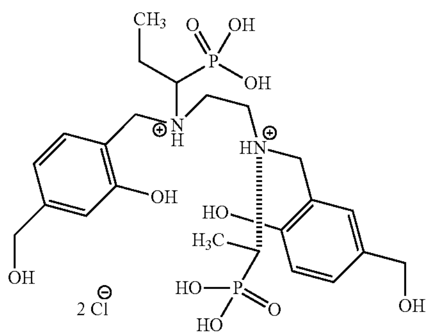 [SMILES: CCC([NH+](CC[N@H+](Cc1cc(CO)ccc1O)C(C)P(=O)(O)O)Cc1ccc(CO)cc1O)P(=O)(O)O] | $R^1$ is hydroxymethyl; $R^2$-$R^3$ are hydrogen; $R^4$ is methyl and ethyl; b is 1. | — | Cl⁻ |
| 4e | 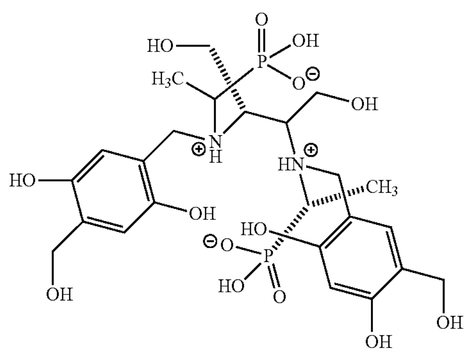 [SMILES: CC([NH+](Cc1cc(O)c(CO)cc1O)[C@H](CO)C(CO)[NH+](Cc1cc(CO)c(O)cc1O)[C@H](C)P(=O)([O-])O)P(=O)([O-])O] | $R^1$ is hydroxy and hydroxymethyl; $R^2$ is hydrogen $R^3$ is hydroxymethyl; $R^4$ is methyl; b is 2. | — | — |
| 4f | 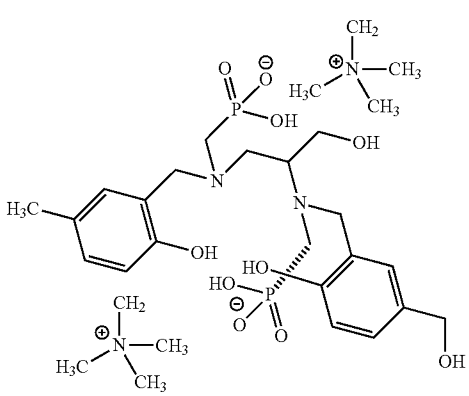 | $R^1$ is methyl and hydroxymethyl; $R^2$ and $R^4$ are hydrogen; $R^3$ is hydroxymethyl and hydrogen; b is 1. | — | — |
| 4g | 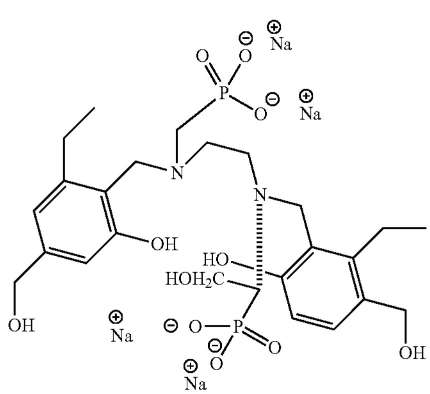 | $R^1$ is hydroxymethyl and ethyl; $R^2$-$R^3$ are hydrogen; $R^4$ is hydroxymethyl and hydrogen; b is 2. | — | — |

TABLE 4-continued

Examples of Metal Chelating Ligands Having Structure XIII And Salts Thereof

| Entry | Structure | Variables R¹-R⁴ Defined As | W | X' |
|---|---|---|---|---|
| 4h | 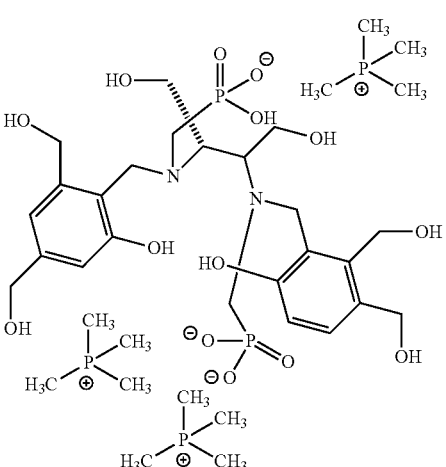 | R¹ is hydroxymethyl; R² and R⁴ are hydrogen; R³ is hydroxymethyl; b is 2. | — | — |
| 4i | 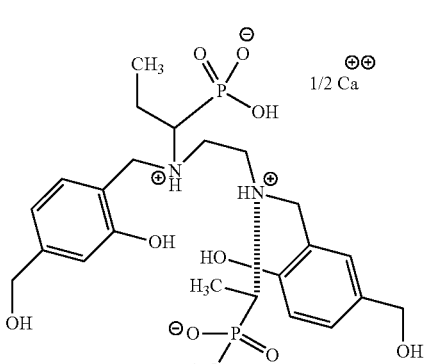 | R¹ is hydroxymethyl; R²-R³ are hydrogen; R⁴ is methyl and ethyl; b is 1. | — | — |

The metal chelating ligands form coordinate complexes with a variety of metals. In one embodiment, the metal chelating ligands form complexes with transition metals. In a particular embodiment, the transition metal is iron.

In one embodiment, the contrast enhancement agent used according to the method of the present invention may be prepared from a metal chelating ligand having an idealized structure XIV and salts thereof.

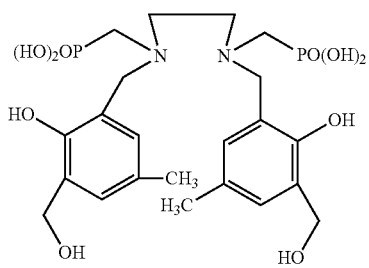

XIV

In another embodiment, the contrast enhancement agent used according to the method of the present invention may be prepared from a metal chelating ligand having an idealized structure XV and salts thereof.

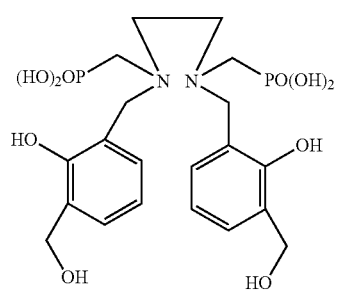

XV

In yet another embodiment, the contrast enhancement agent used according to the method of the present invention may be prepared from a metal chelating ligand having an idealized structure XVI and salts thereof.

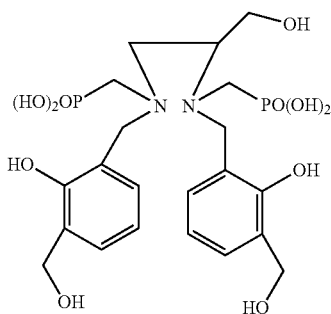

In another embodiment, the contrast enhancement agent used according to the method of the present invention may be prepared from a metal chelating ligand having an idealized structure XVII and salts thereof.

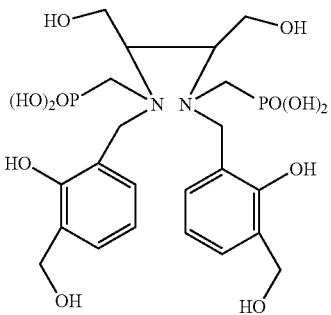

In one embodiment, the contrast enhancement agent used according to the method of the present invention may be prepared from a partially deprotected ligand precursor XVIII and salts thereof having free phosphonic acid groups (or ionized forms thereof)

XVIII wherein with respect only to structure XVIII, $R^8$ is independently at each occurrence a hydroxy group, a protected hydroxy group, a $C_1$-$C_3$ hydroxyalkyl group, a protected $C_1$-$C_3$ hydroxyalkyl group, or a $C_1$-$C_3$ alkyl group; $R^9$-$R^{11}$ are independently at each occurrence hydrogen, a $C_1$-$C_3$ hydroxyalkyl group, a protected $C_1$-$C_3$ hydroxyalkyl group, or a $C_1$-$C_3$ alkyl group; $R^{14}$ and $R^{15}$ are independently at each occurrence a $C_1$-$C_{10}$ alkyl group, a $C_1$-$C_{10}$ alkoxy group, or an aryl group; M is independently at each occurrence a B, Si or carbon; c is 0-3; and d is 0 or 1. The partially deprotected ligand precursor XVIII may be converted to a metal chelating ligand as is demonstrated in the Examples section of this disclosure.

The partially deprotected ligand precursors falling within generic structure XVIII and salts thereof are illustrated in Table 5 below. Those of ordinary skill in the art will understand that Ligand Precursors 5e-5g represent salts of Ligand Precursors 5a-5c.

TABLE 5

Examples Partially Deprotected Ligand Precursors XVIII Having Structure XVIII And Salts Thereof

| Entry | Structure | Variables c, d, $R^8$-$R^{11}$, $R^{14}$, $R^{15}$ and M Defined As |
|---|---|---|
| 5a | (structure) | $R^8$ is $OCH_3$; $R^9$ is $CH_2OH$, $R^{10}$ and $R^{11}$ are hydrogen, c is 1; d is 1; M is carbon, $R^{14}$ is methyl and $R^{15}$ is ethyl. |
| 5b | (structure) | $R^9$ is hydrogen; $R^{10}$ is hydroxymethyl and hydrogen; c is 0; d is 1; M is carbon, $R^{14}$ and $R^{15}$ are $CH_3$. |

TABLE 5-continued

Examples Partially Deprotected Ligand Precursors XVIII Having Structure XVIII And Salts Thereof

| Entry | Structure | Variables c, d, $R^8$-$R^{11}$, $R^{14}$, $R^{15}$ and M Defined As |
|---|---|---|
| 5c | 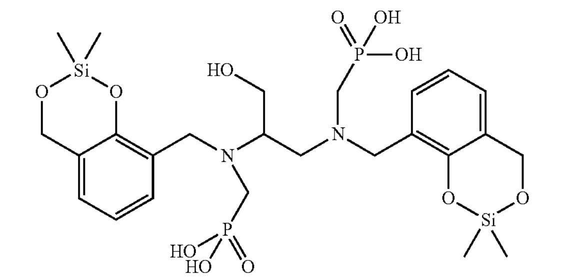 [SMILES: C[Si]1(C)OCc2cccc(CN(CC(CO)N(Cc3cccc4c3O[Si](C)(C)OC4)CP(=O)(O)O)CP(=O)(O)O)c2O1] | $R^9$ is hydrogen; $R^{10}$ is hydroxymethyl and hydrogen; c is 0; d is 1; M is silicon (Si); and $R^{14}$ and $R^{15}$ are $CH_3$. |
| 5d | 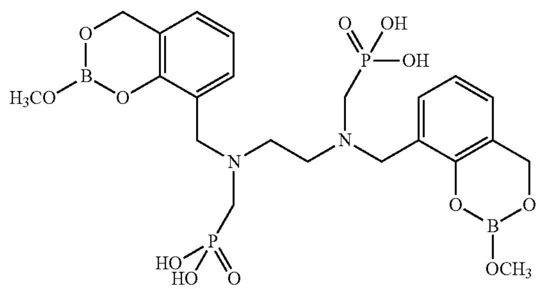 [SMILES: COB1OCc2cccc(CN(CCN(Cc3cccc4c3OB(OC)OC4)CP(=O)(O)O)CP(=O)(O)O)c2O1] | $R^9$-$R^{10}$ are hydrogen; c is 0; d is 0; M is boron (B); and $R^{14}$ is methoxy ($OCH_3$). |
| 5e | 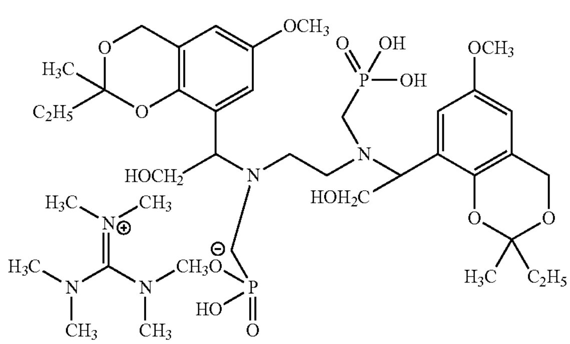 | $R^8$ is $OCH_3$; $R^9$ is $CH_2OH$, $R^{10}$ and $R^{11}$ are hydrogen, c is 1; d is 1; M is carbon, $R^{14}$ is methyl and $R^{15}$ is ethyl. |
| 5f | 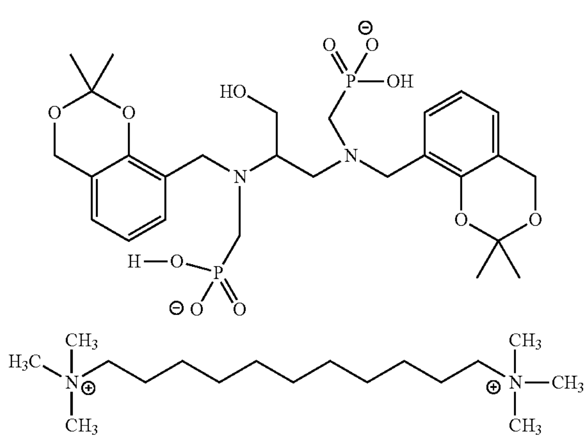 | $R^9$ is hydrogen; $R^{10}$ is hydroxymethyl and hydrogen; c is 0; d is 1; M is carbon, $R^{14}$ and $R^{15}$ are $CH_3$. |

TABLE 5-continued

Examples Partially Deprotected Ligand Precursors XVIII Having Structure XVIII And Salts Thereof

| Entry | Structure | Variables c, d, $R^8$-$R^{11}$, $R^{14}$, $R^{15}$ and M Defined As |
|---|---|---|
| 5g | 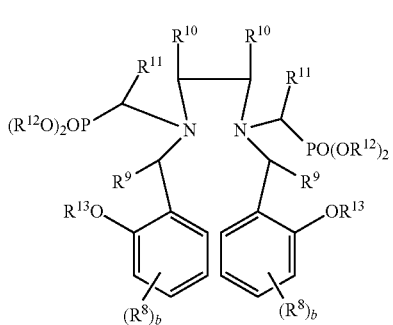 | $R^9$ is hydrogen; $R^{10}$ is hydroxymethyl and hydrogen; c is 0; d is 1; M is silicon (Si); and $R^{14}$ and $R^{15}$ are $CH_3$. |

In one embodiment, the contrast enhancement agent used according to the method of the present invention may be prepared from a partially deprotected ligand precursor falling within the generic structure XVIII having structure XIX and salts thereof.

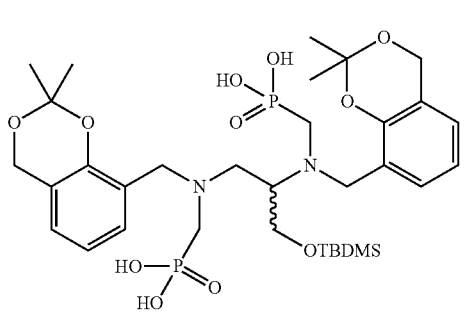

XIX

In one embodiment, the contrast enhancement agent used according to the method of the present invention may be prepared from a partially deprotected ligand precursor corresponding to XVIII wherein the group $R^{15}$ is phenyl.

The contrast enhancement agents used according to the method of the present invention may be prepared from protected ligand precursors. In one embodiment, the protected ligand precursor has a structure XX

XX wherein $R^8$ is independently at each occurrence a protected hydroxy group, a protected $C_1$-$C_3$ hydroxyalkyl group, or a $C_1$-$C_3$ alkyl group, and b is 0-4; $R^9$-$R^{11}$ are independently at each occurrence hydrogen, a protected $C_1$-$C_3$ hydroxyalkyl group, or a $C_1$-$C_3$ alkyl group, with the proviso that at least one of $R^8$-$R^{11}$ is a protected hydroxy group or a protected $C_1$-$C_3$ hydroxyalkyl group; and $R^{12}$ and $R^{13}$ are independently at each occurrence a protecting group selected from the group consisting of $C_1$-$C_{30}$ aliphatic radicals, $C_3$-$C_{30}$ cycloaliphatic radicals, and $C_2$-$C_{30}$ aromatic radicals. A wide variety of protecting groups may be incorporated into the protected ligand precursors provided by the present invention. These include acid sensitive protecting groups (for example the methylthiomethyl group), base sensitive protecting groups for example the acetate and trichloroacetate groups), light sensitive protecting groups (for example the ortho-nitrobenzyl group), groups susceptible to hydrogenolysis (for example the benzyl group), and groups susceptible to metal mediated transformations which enhance their lability (for example the allyl group).

In one embodiment, the contrast enhancement agent used according to the method of the present invention may be prepared from a protected ligand precursor having structure XX wherein $R^{12}$ is independently at each occurrence an ethyl group, a trichloroethyl group, a beta-cyanoethyl group, a trimethylsilyl ethyl group, or a tertiary butyl group. In one embodiment, the contrast enhancement agent used according to the method of the present invention may be prepared from a protected ligand precursor having structure XX wherein $R^{12}$ is at each occurrence an ethyl group. In an alternate embodiment, the contrast enhancement agent used according to the method of the present invention may be prepared from a protected ligand precursor having structure XX wherein $R^{12}$ is at each occurrence a trichloroethyl group. In yet another embodiment, the contrast enhancement agent used according to the method of the present invention may be prepared from a protected ligand precursor having structure XX wherein $R^{12}$ is at each occurrence a beta-cyanoethyl group. In yet still another embodiment, the contrast enhancement agent used according to the method of the present invention may be prepared from a protected ligand precursor having structure XX wherein $R^{12}$ is at each occurrence a trimethylsilyl ethyl group. In yet another embodiment, the contrast enhancement agent used according to the method of the present invention may be prepared from a protected ligand precursor having structure XX wherein $R^{12}$ is at each occurrence a tertiary butyl group.

Protected ligand precursors falling within generic structure XX are illustrated in Table 6 below.

TABLE 6

Examples of Protected Ligands Precursor Having Structure XX

| Entry | Structure | Variables b and $R^8$-$R^{13}$ Defined As |
|---|---|---|
| 6a | 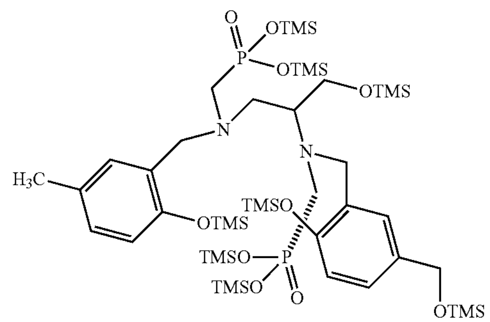 | $R^8$ is methyl and protected hydroxymethyl ($CH_2OTMS$); $R^9$ and $R^{11}$ are hydrogen; $R^{10}$ is protected hydroxymethyl ($CH_2OTMS$) and hydrogen; b is 1; $R^{12}$ is trimethylsilyl; $R^{13}$ is trimethylsilyl. |
| 6b | 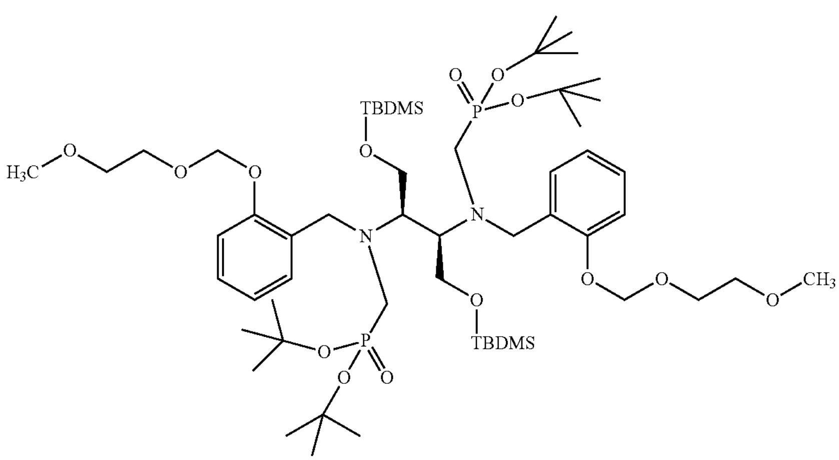 | $R^9$ and $R^{11}$ are hydrogen; $R^{10}$ is protected hydroxymethyl ($CH_2OTBDMS$); b is 0; $R^{12}$ is t-butyl; $R^{13}$ is $CH_3OCH_2CH_2OCH_2$. |
| 6c | 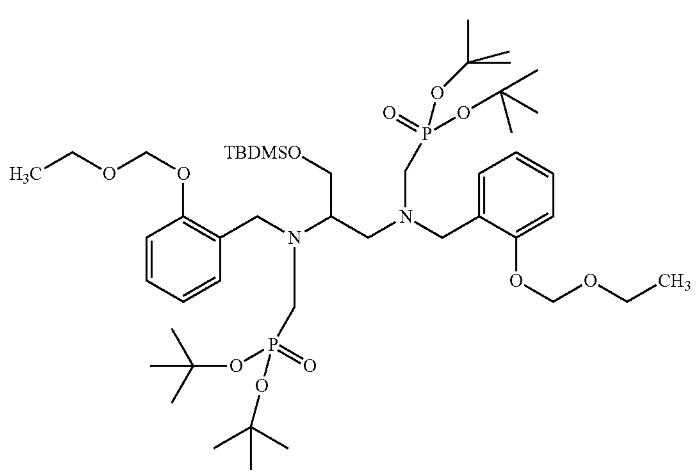 [SMILES: CCOCOc1ccccc1CN(CC(CO[Si](C)(C)C(C)(C)C)N(Cc1ccccc1OCOCC)CP(=O)(OC(C)(C)C)OC(C)(C)C)CP(=O)(OC(C)(C)C)OC(C)(C)C] | $R^9$ and $R^{11}$ are hydrogen; $R^{10}$ is protected hydroxymethyl ($CH_2OTBDMS$); b is 0; $R^{12}$ is t-butyl; $R^{13}$ is $C_2H_5OCH_2$. |

TABLE 6-continued

Examples of Protected Ligands Precursor Having Structure XX

| Entry | Structure | Variables b and $R^8$-$R^{13}$ Defined As |
|---|---|---|
| 6d | 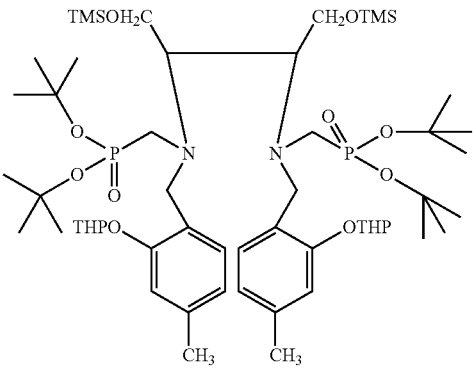 | $R^8$ is methyl; $R^9$ and $R^{11}$ are hydrogen; $R^{10}$ is protected hydroxymethyl ($CH_2OTMS$); b is 1; $R^{12}$ is t-butyl; $R^{13}$ is THP (tetrahydropyranyl). |

In one embodiment, the contrast enhancement agent used according to the method of the present invention may be prepared from a protected ligand precursor having structure XX wherein $R^{12}$ and $R^{13}$ are independently at each occurrence an acid sensitive protecting group. Non-limiting examples of acid sensitive protecting groups include an acetal group, a ketal group, a methoxthyethoxymethyl group, a t-butyl group, a t-butyldimethylsilyl group, a trimethylsilyl group, and a trimethylsilyl ethyl group. In one embodiment, $R^{12}$ is a tertiary butyl group. In another embodiment, $R^{12}$ is a trimethylsilyl group. In another embodiment, $R^{12}$ is a tert-butyldimethylsilyl group. In yet another embodiment, $R^{12}$ is a trimethylsilyl ethyl group. In one embodiment, $R^{13}$ is a THP group. In another embodiment, $R^{13}$ is a methoxthyethoxymethyl group. In another embodiment, $R^{13}$ is a t-butyldimethylsilyl group. In yet another embodiment, $R^{13}$ is a trimethylsilyl group.

In one embodiment, the contrast enhancement agent used according to the method of the present invention may be prepared from a protected ligand precursor having structure XXI.

In another embodiment, the contrast enhancement agent used according to the method of the present invention may be prepared from a protected ligand precursor having structure XXII.

XXII

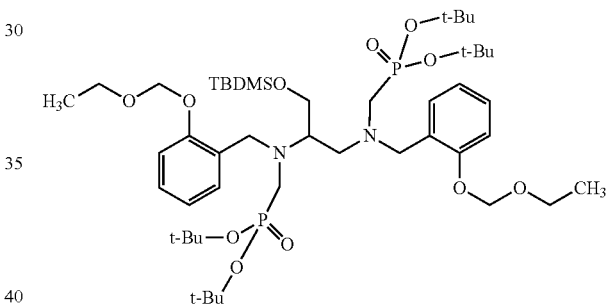

In one embodiment, the contrast enhancement agent used according to the method of the present invention may be prepared from a protected ligand precursor having structure XXIII

XXI

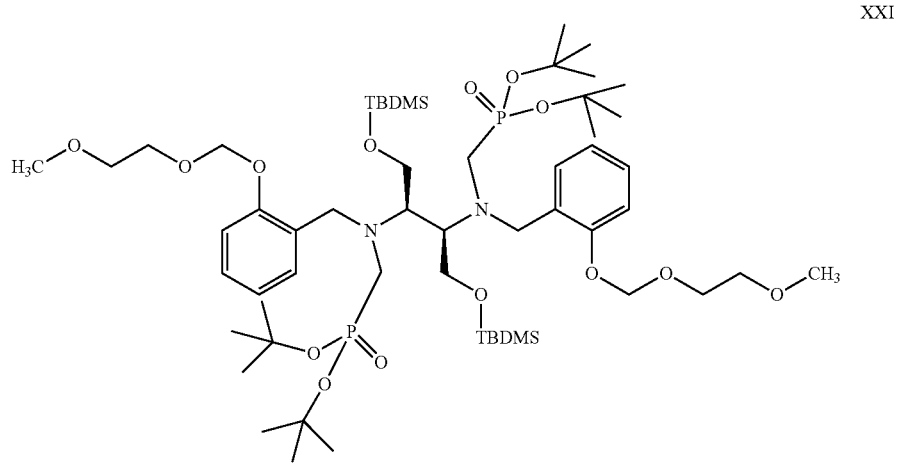

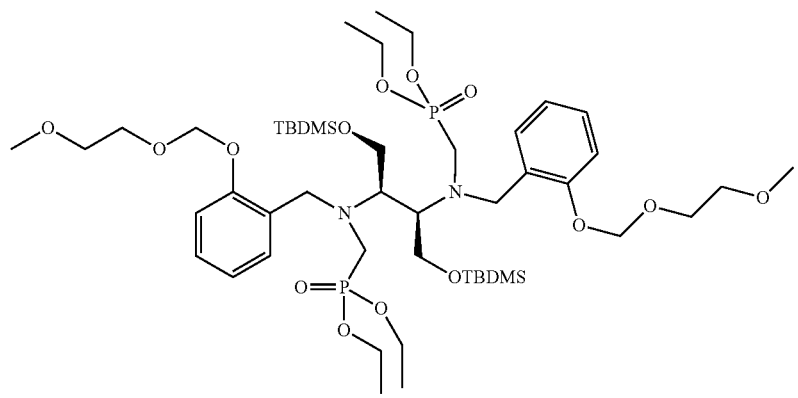

XXIII

In one embodiment, the contrast enhancement agent used according to the method of the present invention may be prepared from a protected ligand precursor having structure XXIV

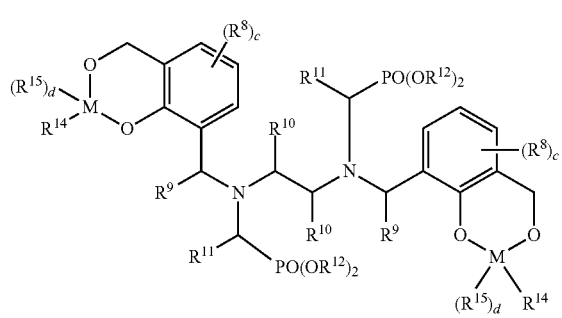

XXIV wherein $R^8$ is independently at each occurrence a protected hydroxy group, a protected $C_1$-$C_3$ hydroxyalkyl group, or a $C_1$-$C_3$ alkyl group; $R^9$-$R^{11}$ are independently at each occurrence hydrogen, a protected $C_1$-$C_3$ hydroxyalkyl group, or a $C_1$-$C_3$ alkyl group; $R^{12}$ is independently at each occurrence a protecting group selected from the group consisting of $C_1$-$C_{30}$ aliphatic radicals, $C_3$-$C_{30}$ cycloaliphatic radicals, and $C_2$-$C_{30}$ aromatic radicals; $R^{14}$ and $R^{15}$ are independently at each occurrence hydrogen, a $C_1$-$C_{10}$ alkyl group, a $C_1$-$C_{10}$ alkoxy group, or an aryl group; or the groups $R^{14}$ and $R^{15}$ may together with M form a carbonyl group or a thiocarbonyl group; M is independently at each occurrence B, Si or carbon; c is 0-3; and d is 0 or 1.

In one embodiment, the contrast enhancement agent used according to the method of the present invention may be prepared from a protected ligand precursor having structure XXIV wherein $R^{12}$ is independently at each occurrence an ethyl group, a trichloroethyl group, a beta-cyanoethyl group, a trimethylsilyl ethyl group, or a tertiary butyl group. In one embodiment, the contrast enhancement agent used according to the method of the present invention may be prepared from a protected ligand precursor having structure XXIV wherein $R^{12}$ is at each occurrence an ethyl group. In an alternate embodiment, the contrast enhancement agent used according to the method of the present invention may be prepared from a protected ligand precursor having structure XXIV wherein $R^{12}$ is at each occurrence a trichloroethyl group. In yet another embodiment, the contrast enhancement agent used according to the method of the present invention may be prepared from a protected ligand precursor having structure XXIV wherein $R^{12}$ is at each occurrence a beta-cyanoethyl group. In yet still another embodiment, the contrast enhancement agent used according to the method of the present invention may be prepared from a protected ligand precursor having structure XXIV wherein $R^{12}$ is at each occurrence a trimethylsilyl ethyl group. In yet another embodiment, the contrast enhancement agent used according to the method of the present invention may be prepared from a protected ligand precursor having structure XXIV wherein $R^{12}$ is at each occurrence a tertiary butyl group.

Protected ligand precursors falling within generic structure XXIV are illustrated in Table 7 below.

TABLE 7

Examples of Protected Ligand Precursors Having Structure XXIV

| Entry | Structure | Variables c, d, $R^8$-$R^{12}$, $R^{14}$, $R^{15}$ and M Defined As |
|---|---|---|
| 7a | 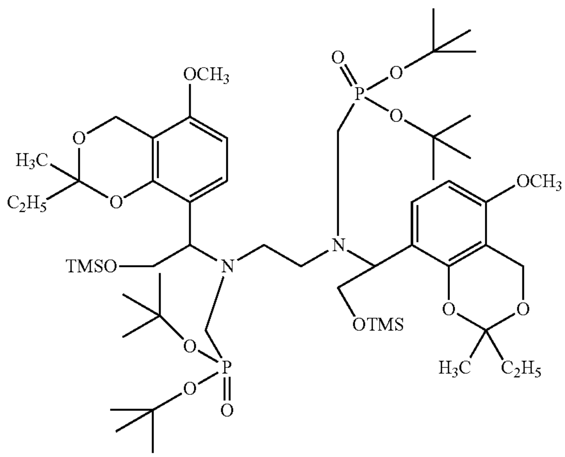 | $R^8$ is OCH3; c is 1; d is 1; $R^9$ is protected hydroxymethyl ($CH_2OTMS$); $R^{10}$ and $R^{11}$ are hydrogen; $R^{12}$ is t-butyl; M is carbon, $R^{14}$ is methyl group and $R^{15}$ is ethyl. |
| 7b | 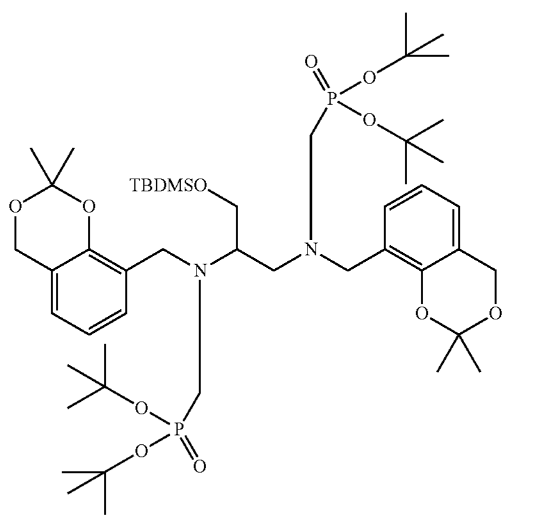 [SMILES: CC(C)(C)OP(=O)(CN(Cc1cccc2c1OC(C)(C)OC2)CC(CO[Si](C)(C)C(C)(C)C)N(Cc1cccc2c1OC(C)(C)OC2)CP(=O)(OC(C)(C)C)OC(C)(C)C)OC(C)(C)C] | $R^9$ and $R^{11}$ are hydrogen; $R^{10}$ is protected hydroxymethyl ($CH_2OTBDMS$); c is 0; d is 1; $R^{12}$ is t-butyl; $R^{14}$ and $R^{15}$ are $CH_3$ |
| 7c | 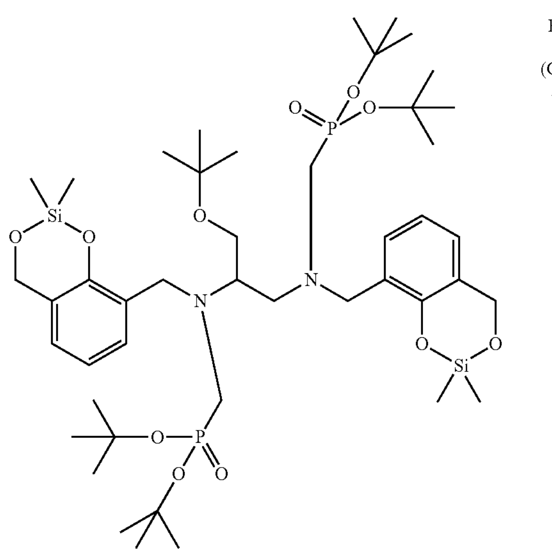 | $R^9$ and $R^{11}$ are hydrogen; $R^{10}$ is protected hydroxymethyl ($CH_2$O-t-butyl); c is 0; d is 1; $R^{12}$ is t-butyl; M is Si; and $R^{14}$ and $R^{15}$ are $CH_3$. |

TABLE 7-continued

Examples of Protected Ligand Precursors Having Structure XXIV

| Entry | Structure | Variables c, d, $R^8$-$R^{12}$, $R^{14}$, $R^{15}$ and M Defined As |
|---|---|---|
| 7d | 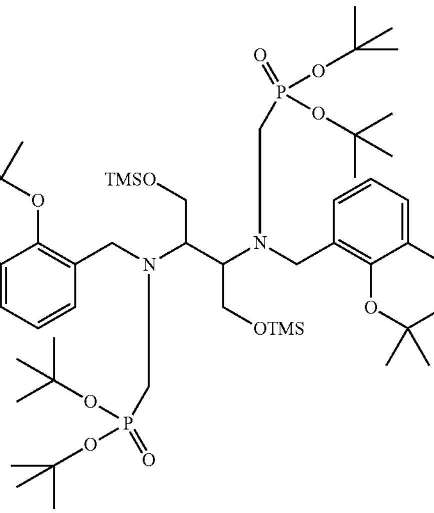 | $R^9$ and $R^{11}$ are hydrogen; $R^{10}$ is protected hydroxymethyl ($CH_2OTMS$); c is 0; d is 1; $R^{12}$ is t-butyl; M is carbon, $R^{14}$ and $R^{15}$ are $CH_3$. |

In one embodiment, protected ligand precursor having structure has structure XXIV wherein $R^{12}$ is independently at each occurrence an acid sensitive protecting group selected from the group consisting of an acetal group, a ketal group, methoxthyethoxymethyl group, t-butyl group, t-butyldimethylsilyl group, trimethylsilyl group, and a trimethylsilyl ethyl group. In one embodiment, $R^{12}$ is a tertiary butyl group. In another embodiment, $R^{12}$ is a trimethylsilyl group. In another embodiment, $R^{12}$ is a tert-butyldimethylsilyl group. In yet another embodiment, $R^{12}$ is a trimethylsilyl ethyl group.

In a particular embodiment, the contrast enhancement agent used according to the method of the present invention may be prepared from a protected ligand precursor corresponding to XXIV wherein the group $R^{15}$ is phenyl, for example as in the case in which M is carbon, $R^{14}$ is methyl, and $R^{15}$ is phenyl.

In one embodiment, the contrast enhancement agent used according to the method of the present invention may be prepared from a protected ligand precursor having structure XXV.

XXV

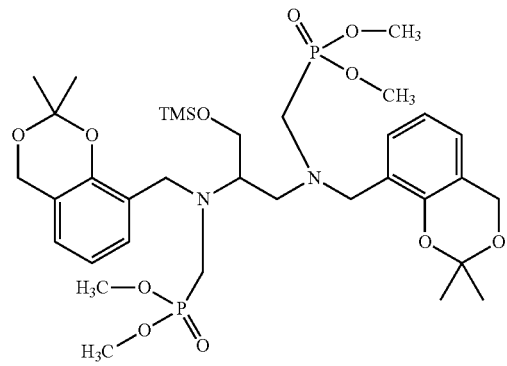

In another embodiment, the contrast enhancement agent used according to the method of the present invention may be prepared from a protected ligand precursor having structure XXVI.

XXVI

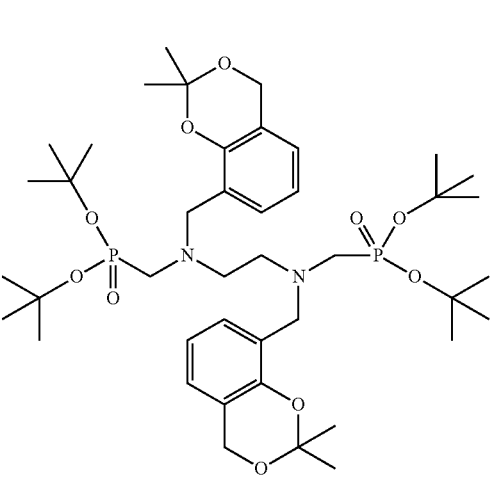

In yet another embodiment, the contrast enhancement agent used according to the method of the present invention may be prepared from a protected ligand precursor having s structure XXVII.

XXVII

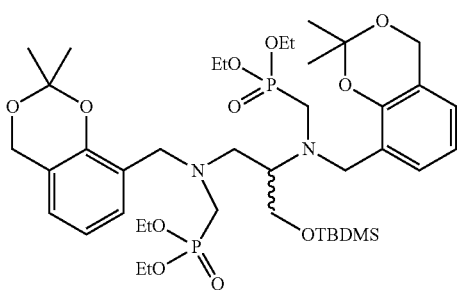

In yet another embodiment, the contrast enhancement agent used according to the method of the present invention may be prepared from a protected ligand precursor having structure XXVIII.

XXVIII

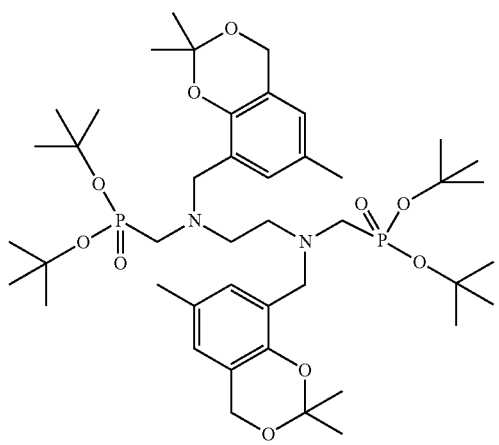

In another embodiment, the contrast enhancement agent used according to the method of the present invention may be prepared from a protected ligand precursor having structure XXIX.

XXIX

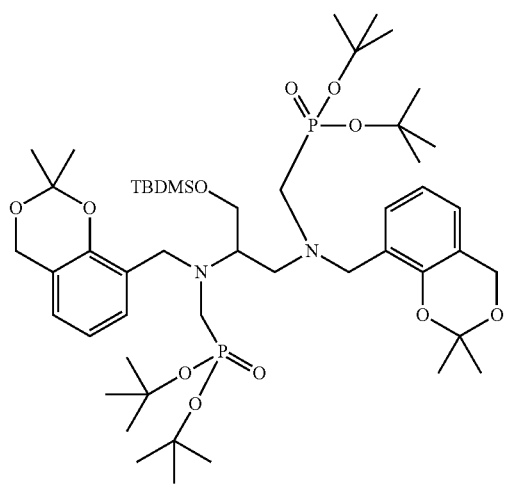

As mentioned above throughout this disclosure, no absolute or relative stereochemistry is intended to be shown for a structure, as in for example structures XX and XXIV, and the structures are intended to encompass all possible absolute and relative stereochemical configurations, unless specified otherwise. Thus, for example, structure XX depicts a compound in which no absolute or relative stereochemistry is intended to be shown. As such, structure XX is intended to represent a genus of compounds which includes the racemic compounds, single enantiomers, enantiomerically enriched compositions and mixtures of diastereomers.

In one embodiment, the present invention comprises the use of a medical formulation comprising the contrast enhancement agent having structure I and salts thereof. In yet another embodiment, the present invention comprises the use of a medical formulation comprising the contrast enhancement agent having structure II and salts thereof. In another embodiment, the method of the present invention comprises the use of a medical formulations comprising at least one structure selected from structures III and salts thereof, IV and salts thereof, V and salts thereof, VI and salts thereof, VII and salts thereof, and VIII and salts thereof. The contrast enhancement agents used according to the method of the present invention are suitable for use as imaging agents for magnetic resonance (MR) screening of human patients for various pathological conditions. As will be appreciated by those of ordinary skill in the art, MR imaging has become a medical imaging technique of critical importance to human health. In one embodiment, the present invention provides a method for increasing the emitted signal, and thus obtaining in vivo differentiation of tissues in an organism by administering a contrast enhancement agent to a living subject and conducting magnetic resonance imaging of the subject. In one embodiment, the contrast enhancement agent used according to the method of the present invention includes an iron chelate wherein the iron is paramagnetic. Contrast enhancement agents used according to the method of the present invention comprising a paramagnetic iron center are believed to be readily excreted by human patients and by animals and as such are rapidly and completely cleared from the patient following the magnetic resonance imaging procedure. In addition, the contrast enhancement agents used according to the method of the present invention may enable the administration of lower levels of the contrast enhancement agent to the patient relative to known contrast enhancement agents without sacrificing image quality. Thus, in one embodiment, useful MR contrast enhancement using the contrast enhancement agent according to the method of the present invention, is achieved at lower dosage level in comparison with known MR contrast agents. In an alternate embodiment, the contrast enhancement agents used according to the method of the present invention may be administered to a patient at a higher dosage level in comparison with known MR contrast agents in order to achieve a particular result. Higher dosages of the contrast enhancement agents of the present invention may be acceptable in part because of the enhanced safety of such iron-based contrast enhancement agents, and improved clearance of the contrast enhancement agent from the patient following the imaging procedure. In one embodiment, the contrast enhancement agent is administered in a dosage amount corresponding to from about 0.001 to about 5 millimoles per kilogram weight of the patient. As will be appreciated by those of ordinary skill in the art, contrast enhancement agents used according to the method of the present invention may be selected and/or further modified to optimize the residence time of the contrast enhancement agent in the patient, depending on the length of the imaging time required.

In one embodiment, the method of the present invention may be used for imaging the circulatory system, the genitourinary system, hepatobiliary system, central nervous system, for imaging tumors, abscesses and the like. In another embodiment, the method of the present invention may also be useful to improve lesion detectability by MR enhancement of either the lesion or adjacent normal structures. In certain embodiments, the method of the present invention may be used in abiotic systems to elucidate structures within the system. Under such circumstances the subject is inanimate or abiotic. Thus, in one embodiment the contrast enhancement agent of the present invention may be used to image flow channels formed in a subject which is fixed bed catalyst. Thus, a solution containing the contrast enhancement agent may be circulated through a fixed bed catalyst column which is susceptible to channeling. Channels are associated with higher flow rates and thus greater exposure to the contrast enhancement agent over time. When the contrast enhancement agent is susceptible to a relatively strong interaction with the catalyst surface, significantly higher concentrations of the contrast enhancement agent may be present in the channel regions as opposed to non-channel regions of the fixed bed catalyst after a given period of passing the contrast enhancement agent through the catalyst bed. The catalyst bed may then be imaged, for example using standard MR imaging equipment.

In applications involving living subjects, the contrast enhancement agent may be administered by any suitable method for introducing a contrast enhancement agent to the area of interest, for example by injection of ingestion, or both. When administered to a living subject, the contrast enhancement agent is typically administered as a medical formulation comprising the contrast enhancement agent and one or more pharmaceutically acceptable carriers and excipients. As used herein when referring to a medical formulation, the expression "one or more pharmaceutically acceptable carriers and excipients", means that at least one of a pharmaceutically acceptable carrier or a pharmaceutically acceptable excipient is present in the formulation. Thus, in one embodiment, a medical formulation used according to the method of the present invention comprises a contrast enhancement agent and one or more pharmaceutically acceptable carriers. In an alternate embodiment, a medical formulation used according to the method of the present invention comprises a contrast enhancement agent and one or more pharmaceutically acceptable excipients. In another embodiment, a medical formulation used according to the method of the present invention comprises a contrast enhancement agent and one or more pharmaceutically acceptable carriers and one or more pharmaceutically acceptable excipients. The medical formulation containing the contrast enhancement agent is desirably sterile and is typically administered intravenously and may contain various pharmaceutically acceptable agents, which promote the dispersal of the contrast enhancement agent. In one embodiment, the medical formulation used according to the method of the present invention is an aqueous solution containing the contrast enhancement agent and an aqueous solvent. In one embodiment of the present invention, a medical formulation is administered to a human subject (patient) in an aqueous formulation comprising ethanol and the contrast enhancement agent. In an alternate embodiment, the medical formulation (as an MR imagining agent) may be administered to a patient as an aqueous formulation comprising dextrose and the contrast enhancement agent. In yet another embodiment, the MR imagining agent may be administered to a patient as an aqueous formulation comprising saline and the contrast enhancement agent.

In addition to being useful as MR imaging agents and as probes for determining the suitability of a given iron chelate compound for use as a MR imaging agent, the contrast enhancement agents used according to the method of the present invention may also, in certain embodiments, possess therapeutic utility in the treatment of one or more pathological conditions in humans and/or animals. Thus, in one embodiment, the contrast enhancement agent used according to the method of the present invention and having structure I and salts thereof, may be useful in treating a pathological condition in a patient. In an alternate embodiment, the contrast enhancement agent used according to the method of the present invention and having structure II and salts thereof, may be useful in treating a pathological condition in a patient.

Those skilled in the art will appreciate that iron chelate compounds falling within the scope of generic structure I may under a variety of conditions form salts which are useful as MR imaging agents, probes for the discovery and development of imaging agents, and/or as therapeutic agents. Thus, the present invention provides methodology for the productive use of a host of novel and useful iron chelate compounds and their salts.

The contrast enhancement agent used according to the method of the present invention may be prepared by a variety of methods including those provided in the experimental section of this disclosure. For example, stoichiometric amounts of the metal ion and the metal chelating ligand may be admixed in a solution with an appropriate adjustment of pH, if necessary. The contrast enhancement agent may be isolated by conventional methods such as crystallization, chromatography, and the like, and admixed with conventional pharmaceutical carriers suitable for pharmaceutical administration.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

EXAMPLES

Method 1 Preparation of Diphosphonate Compound 1

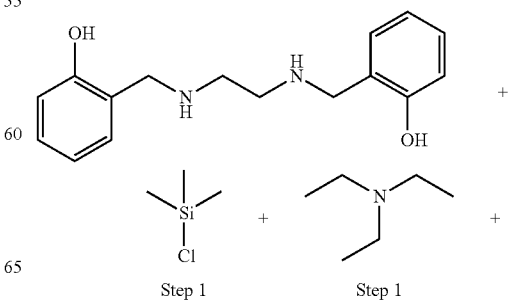

Step 1  Step 1

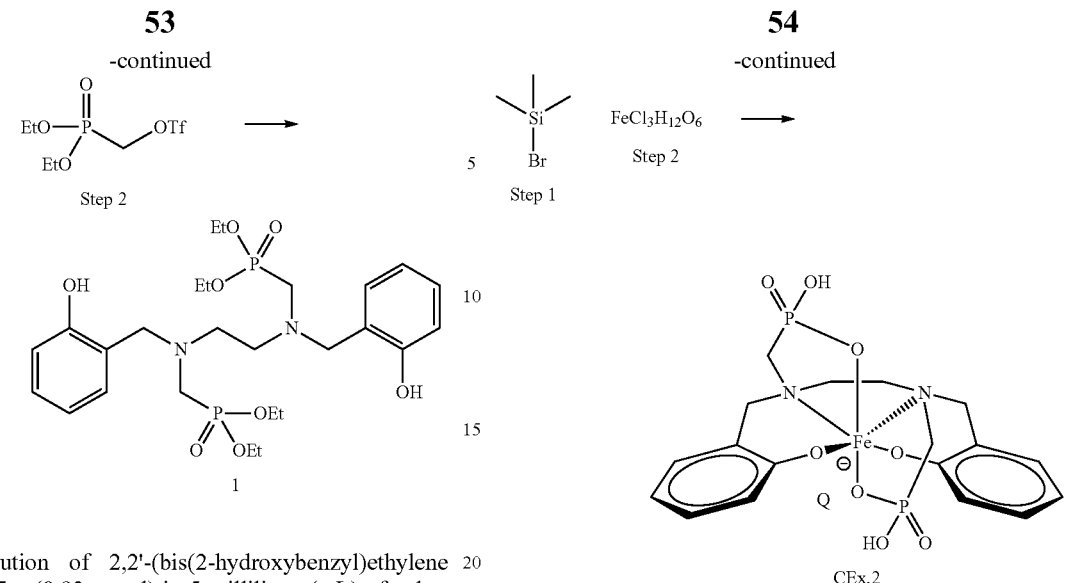

To a solution of 2,2'-(bis(2-hydroxybenzyl)ethylene diamine (0.25 g (0.92 mmol) in 5 milliliters (mL) of anhydrous tetrahydrofuran (THF) at 0° C. was added triethylamine (0.63 mL, 4.6 mmol) followed by the addition of 0.23 mL (2.0 mmol) of trimethylsilyl chloride (TMSCl). The reaction mixture was stirred for 30 minutes. A solution of phosphonomethyltriflate (0.67 gram, 2.0 mmol) in 1 mL of THF was added to the reaction mixture. The reaction mixture was stirred overnight, slowly warming to room temperature over this time. The mixture was poured into saturated aqueous sodium bicarbonate solution and diluted with 20 mL of diethylether. The aqueous and organic layers were separated and the aqueous layer was extracted with diethylether (3×25 mL). The combined organic layers were washed with saturated aqueous sodium bicarbonate solution, (2×25 mL), and brine (2×25 mL), dried over $MgSO_4$ and filtered. The filtrate was concentrated under reduced pressure to provide the crude product as a pale yellow oil. The crude product was purified by flash chromatography on normal phase silica ($SiO_2$, 12 g) using the following gradient program at 30 mL/min: 2% MeOH-Dichloromethane for 5 column volumes, then ramp to 10% MeOH-Dichloromethane over 30 column volumes, finally holding at 10% MeOH-Dichloromethane for 5 column volumes. The column eluant was monitored at 277 nm and the purified material was pooled and concentrated under reduced pressure to provide compound 1 as a colorless oil that was further dried under high vacuum (80% yield), and analyzed using liquid chromatography—mass spectrometry—electrospray ionization (LCMS (ESI)) 595 (M+Na)$^+$.

Method 2 Preparation of Iron Chelate Compound CEx.2

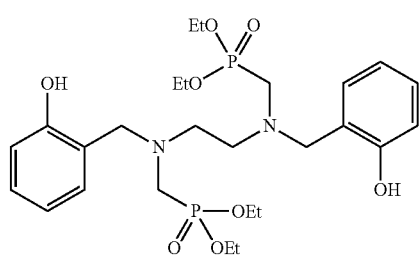

To a solution of tetraethyl (ethane-1,2-diylbis((2-hydroxybenzyl)azanediyl))bis(methylene)diphosphonate (0.42 g, 0.74 mmol) 1 was added 0.78 mL, (5.9 mmol) of trimethylsilyl bromide at room temperature. The reaction mixture was heated to a temperature of 75° C. for 120 min to allow for clean conversion to the product CEx.2 as evidenced by LCMS ESI 461 (M+H)+. The solvent was removed under reduced pressure, and the residue was diluted with acetone-water (4:1) and stirred overnight. The remaining solvent was removed under reduced pressure and the residue was dissolved in water. Ferric chloride ($FeCl_3$ $6H_2O$, 0.93 equivalents) solution was added to the residue followed by addition of 1 molar (M) sodium hydroxide to adjust the pH of the solution to 7.4. The solution was filtered through a Sephadex G-10 column to yield a filtrate containing the complex CEx.2 in which the charge balancing counterion Q is believed to be primarily sodium cation. The filtrate was subsequently assessed for total Fe concentration and relaxivity, LCMS (ESI) 513 (M+H)$^+$$\lambda_{max}$ (DI)=455 nm.

Method 3 Preparation of Diamine Compound 2

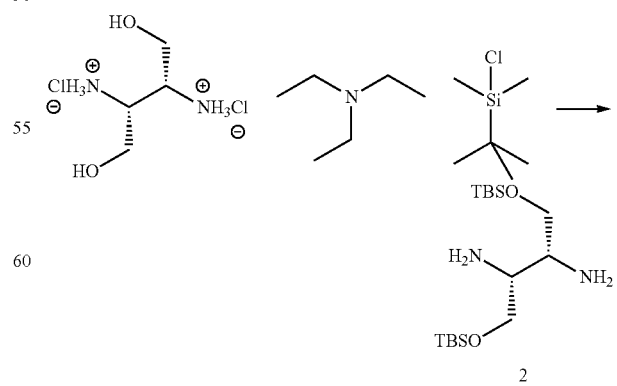

To a stirred solution of 2,3-diamino butane-1,4-diol bishydrochloride (1.87 g, 9.7 mmol) in 10 mL of anhydrous DMF at room temperature, was added 6.6 mL (48 mmol) of triethylamine followed by the addition of tert-butyldimethylsilyl chloride (TBDMS-Cl) (3.0 g, 19.8 mmol). The reaction mixture was allowed to stir overnight. The reaction mixture was then concentrated under reduced pressure to remove most of the DMF and then quenched by the addition of saturated aqueous potassium carbonate solution (20 mL) and further diluted with 10 mL of dichloromethane. The aqueous and organic layers were separated. The aqueous layer was extracted with dichloromethane (3×25 mL) and the combined organic layers were washed with saturated aqueous potassium carbonate solution, (2×25 mL) and brine, dried over MgSO$_4$ and filtered. The resultant solution was concentrated under reduced pressure to provide the crude product 2 as a crystalline solid. The crude product 2 was purified by flash chromatography on normal phase silica gel (40 gram column) using the following gradient program at 40 mL/min: 100% dichloromethane containing 0.5% triethylamine for 2 column volumes, then ramp to 20% MeOH-Dichloromethane each containing 0.5% triethylamine over 20 column volumes, finally holding at 20% MeOH-Dichloromethane each containing 0.5% triethylamine for 3 column volumes. The column eluant was monitored at 230 nm and the fractions containing the purified diamine compound 2 were pooled and concentrated under reduced pressure. Purified diamine 2 having the absolute stereochemistry shown was analyzed by LCMS (ESI) 349 (M+H)$^+$ and was then taken on to the next step (Method 5 below).

Method 4 Preparation of Aldehyde Compound 3

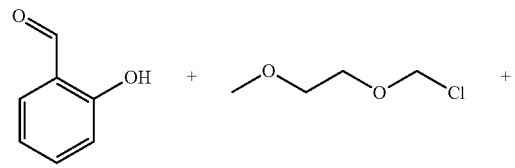

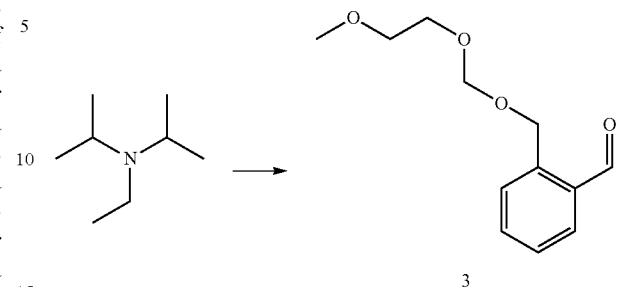

To a solution containing 6 mL (57.3 mmol) of 2-hydroxybenzaldehyde in 190 mL of dichloromethane at 0° C. was added 13.6 mL (80 mmol) of Hunig's base. This was followed by addition of 7.3 mL (57.3 mmol) of MEM-Cl. The reaction mixture was allowed to stir overnight while, slowly warming to room temperature. At the end of the allotted time, the reaction mixture was quenched by the addition of saturated aqueous NH$_4$Cl solution (100 mL). The aqueous and organic layers were separated. The aqueous layer was extracted with two additional 50 mL portions of dichloromethane. The combined organic layers were washed with saturated aqueous potassium carbonate solution, (2×20 mL), brine (50 mL), dried over MgSO$_4$ and filtered. The filtrate was concentrated under reduced pressure to provide the crude product 3 as an oil. The crude product 3 was purified by flash chromatography on normal phase silica gel (40 gram column, 0-10% EtOAc-hexanes) to provide the purified compound 3 which was analyzed by LCMS (ESI) 233 (M+Na)$^+$.

Method 5 Preparation of Compound 4

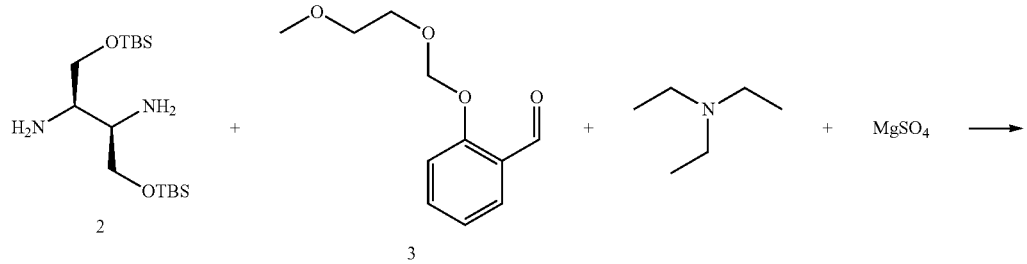

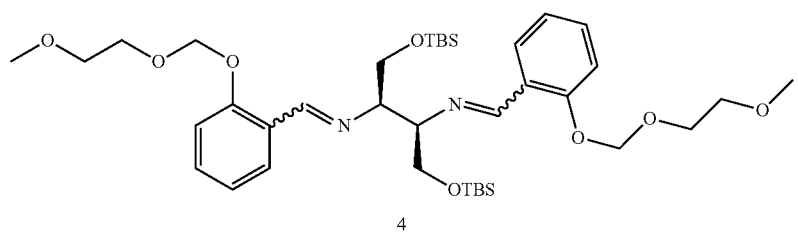

To a stirred suspension of the diamine compound 2 (1.3 g, 3.7 mmol) in dichloromethane (10 mL), were added triethylamine (1.3 mL, 9.3 mmol) and MgSO$_4$ (1.8 g, 14.9 mmol). After stirring for 1.5 h at room temperature a solution of the aldehyde compound 3 (1.57 g, 7.46 mmol) in dichloromethane (5 mL) was added. The reaction mixture was allowed to stir overnight. The reaction mixture was then filtered to remove solid materials and then concentrated under reduced pressure to provide a crude product. The crude product was triturated with diethyl ether, the ether was filtered and concentrated under reduced pressure to provide a yellow oil. The conversion of aldehyde 3 ($\delta$ 10.55 ppm) to bisimine 4 ($\delta$ 8.76 ppm) was confirmed by NMR spectroscopy. $^1$H NMR (CD$_2$Cl$_2$, 400 MHz) $\delta$ 0.06 (s, 6H), 0.11 (s, 6H), 0.93 (s, 18H), 3.36 (s, 6H), 3.54-3.58 (m, 4H), 3.65-3.70 (m, 2H), 3.75-3.80 (m, 2H), 3.81-3.84 (m, 4H), 4.07-4.13 (m, 2H), 5.32 (s, 4H), 7.03-7.09 9 m, 2H), 7.20-7.25 (m, 2H), 7.37-7.43 (m, 2H), 8.01-8.07 (m, 2H) and 8.76 (s, 2H); $^{13}$C{$^1$H}NMR $\delta$ −5.49, 18.13, 25.69, 50.60, 66.83, 67.92, 71.59, 74.55, 93.70, 114.66, 121.65, 125.61, 127.42, 131.52, 156.77, and 157.86.

Method 6 Preparation of Diamine Compound 5 organic layers were separated and the aqueous layer was extracted with dichloromethane (3×25 mL) and the combined organic layers were washed with saturated aqueous sodium bicarbonate solution, (2×25 mL), brine (2×25 mL), dried over MgSO$_4$ and filtered. The filtrate was concentrated under reduced pressure to provide the crude product as a pale yellow oil which was purified by flash chromatography (SiO$_2$, 40 gram column) using the following gradient program at 60 mL/min: 100% dichloromethane containing 0.5% triethylamine for 3 column volumes, then ramp to 10% MeOH-Dichloromethane each containing 0.5% triethylamine over 20 column volumes, finally holding at 10% MeOH-Dichloromethane each containing 0.5% triethylamine for 2 column volumes. The column eluant was monitored at 278 nm and the fractions containing the purified material were pooled, concentrated under reduced pressure. The orange colored product obtained was further dried under high vacuum and was then analyzed by LCMS. LCMS analysis indicated that only partial purification of the reaction product had been achieved. Thus, the crude product was again subjected to flash chromatography on normal phase silica gel (40 gram column) using the following gradient program at 40 mL/min: 50% EtOAc-hexanes for 3 column volumes, then ramp to 75% EtOAc-hexanes over 20 column volumes, finally holding at 75%

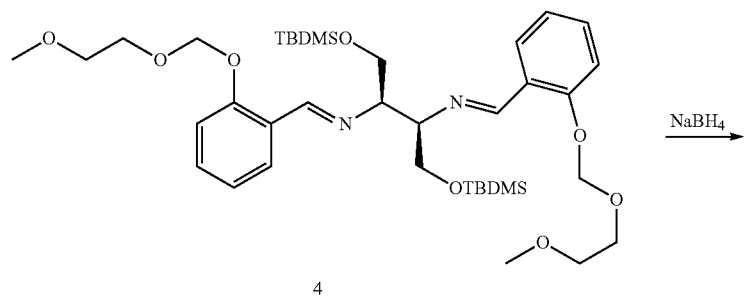

4

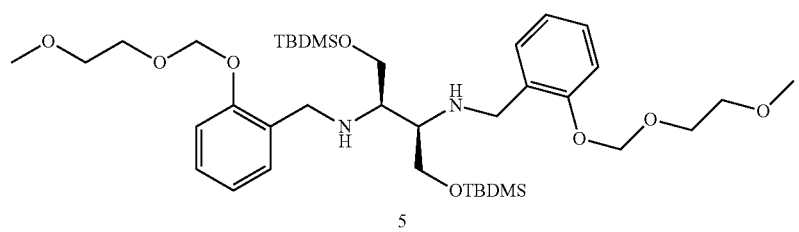

5

To a solution of 2.7 g (3.7 mmol) of the bisimine 4 in 4 mL of dichloromethane at 0° C. was added a solution of 0.56 g (14.9 mmol) of sodium borohydride in 1 mL of methanol via an additional funnel. The reaction mixture was allowed to warm to room temperature and stirred overnight. The reaction mixture was then quenched by the addition of 10 mL saturated aqueous potassium carbonate solution. The aqueous and EtOAc-hexanes for 6 column volumes. The column eluant was monitored at 277 nm, and the fractions containing the purified material were pooled and concentrated under reduced pressure. The purified material was obtained as a colorless oil and then dried under high vacuum to yield purified diamine compound 5 as a colorless oil, LCMS (ESI) 737 [M+H]$^+$.

Example 1

Preparation of Ligand Precursor Compound XXIII

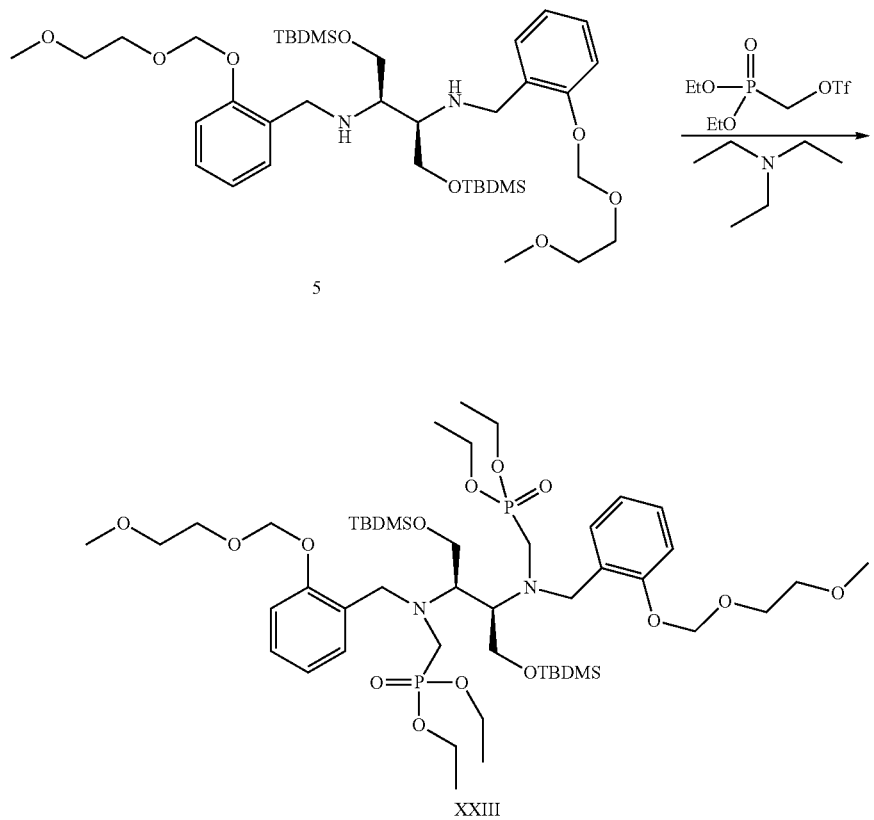

TBDMS = t-butyldimethysilyl

To a stirred solution of the diamine compound 5 (0.1 g, 0.14 mmol) in 1.4 mL of THF at 0° C. was added triethylamine (74 μL, 0.54 mmol) followed by 0.12 g (0.41 mmol) of (diethoxyphosphoryl)methyl trifluoromethanesulfonate. The reaction mixture was allowed to warm to room temperature and stirred overnight. The reaction mixture was then quenched with 10 mL of saturated aqueous potassium carbonate solution and diluted with 10 mL of dichloromethane. The aqueous and organic layers were separated and the aqueous layer was extracted with dichloromethane (3×25 mL). The combined organic layers were dried over MgSO₄ and filtered. The filtrate was concentrated under reduced pressure to provide the crude product as a pale yellow oil which was purified by flash chromatography on normal phase silica gel (40 gram column) using the following gradient program at 40 mL/min: 75% EtOAc-hexanes containing 0.5% triethylamine for 3 column volumes, then ramp to 95% EtOAc-hexanes containing 0.5% triethylamine over 12 column volumes, finally holding at 95% EtOAc-hexanes containing 0.5% triethylamine for 12 column volumes. The column eluant was monitored at 281 nm and fractions containing the purified material were pooled, and concentrated under reduced pressure to yield purified diamine compound XXIII as a colorless oil, 1037 [M+H]⁺, 1059 (M+Na)⁺.

Method 7 Preparation of Aldehyde Compound 6

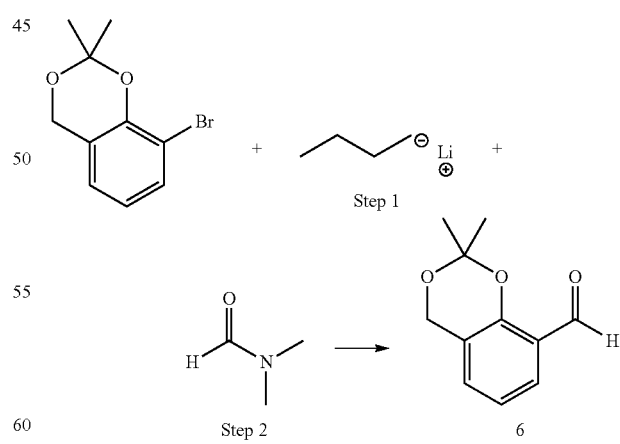

The starting material, 3-bromosalicyl alcohol isopropylidene acetal was prepared as using the method described in Meier C. et al. *Eur J. Org. Chem.* 2006, 197-206. A suitable reaction vessel was charged with 8.31 mL of n-butyllithium (2.5 M in hexanes, 20.77 mmol) and was diluted with 30 mL of anhydrous tetrahydrofuran (THF) and cooled to −75° C. (acetone/dry ice bath). A solution of 3-bromosalicyl alcohol isopropylidene acetal (5.05 g, 22.1 mmol) in 15 mL anhydrous THF was then added over a period of 1.5 h, while maintaining the internal reaction temperature at or below −70° C. Following the addition of the 3-bromosalicyl alcohol isopropylidene acetal, the reaction mixture was stirred for an additional 30 minutes while maintaining the temperature at or below −70° C. Anhydrous DMF (1.62 mL, 20.77 mmol) was then added to the reaction mixture over a period of 30 seconds. The reaction mixture was allowed to re-equilibrate to a temperature of −70° C., and was then warmed to 0° C. and quenched with methanol (30 mL). The quenched reaction mixture was poured into saturated aqueous NaHCO$_3$, and extracted portionwise with dichloromethane (3×75 mL). The combined organic extracts were dried over MgSO$_4$, filtered, and concentrated under reduced pressure to provide a yellow oil that solidified on standing under high vacuum. The crude product was purified by flash chromatography on silica gel (40 g column, isocratic, 10% EtOAc-hexanes, 254 and 327 nm) to afford the aldehyde compound, 6, as a pale yellow solid in 70% yield. $^1$H NMR (CD$_2$Cl$_2$, 400 MHz) δ 1.63 (s, 6H), 4.93 (s, 2H), 7.01 (t., J=7.6 Hz, 1H), 7.24-7.28 (m., 1H), 7.69-7.73 (m., 1H), 10.43 (d., J=0.75 Hz).

Method 8 Preparation of Compound 7

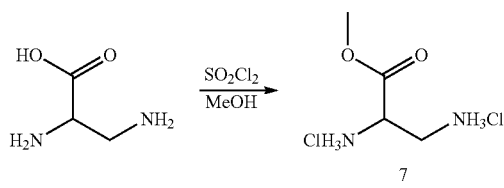

Thionyl chloride (31.7 g, 266.8 mmol) was added drop wise to a stirred suspension of 2,3-diaminopropionic acid monohydrochloride (5.0 g, 35.6 mmol) in methanol (75 mL) over a period of 5 min. The reaction mixture was heated to 80° C. for 6 h. At the end of the stipulated time, the reaction mixture was cooled and the volatiles were removed under reduced pressure to obtain compound 7 (6.8 g, 100%) as an off-white solid. $^1$H NMR (MeOD): δ 4.51 (m, 1H), δ 3.96 (s, 3H), δ 3.53 (m, 2H).

Method 9 Preparation of Aldehyde Compound 8

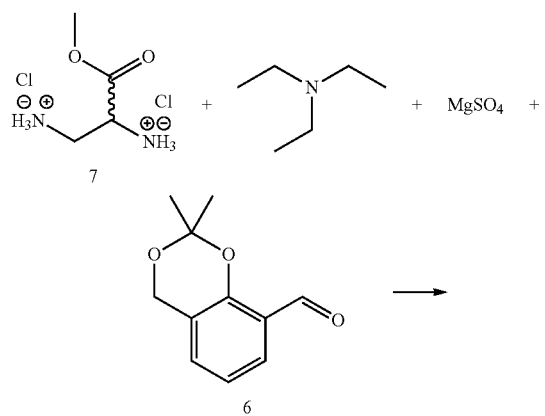

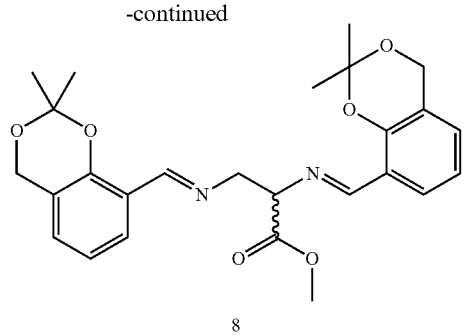

To a suspension of the diamine compound 7 (1.00 g, 5.2 mmol) in dichloromethane (15 mL) at room temperature was added triethylamine (3.3 mL, 23.6 mmol) and MgSO$_4$ (2.5 g, 20.9 mmol). The reaction mixture was stirred for 1.5 h at room temperature and then a solution of the aldehyde 6 (2.0 g, 10.6 mmol) in anhydrous dichloromethane (6 mL) was added to the reaction mixture. The reaction mixture was stirred overnight. Following this time, the reaction was filtered and concentrated under reduced pressure to provide the bisimine 8 which was analyzed by NMR to confirm the presence of the desired imine protons at δ 8.71 and 8.69 ppm.

Method 10 Preparation of Diamine Compound 9

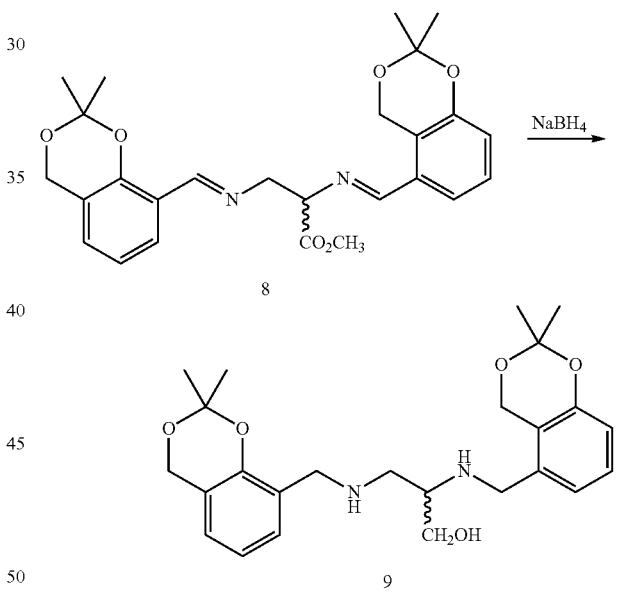

To a stirred solution of compound 8 (2.4 g, 5.2 mmol) in dichloromethane (21 mL) at 0° C. was added a solution of sodium borohydride (1.2 g, 31.9 mmol) in methanol (5.3 mL) via an additional funnel. The reaction mixture was allowed to slowly warm to room temperature with stirring overnight. The reaction mixture was quenched with 25 mL of saturated aqueous potassium carbonate solution. The aqueous layer and the organic layers were separated. The aqueous layer was extracted with dichloromethane (3×25 mL) and the combined organic layers were washed with saturated aqueous sodium bicarbonate solution, (2×25 mL), and brine (2×25 mL), dried over MgSO$_4$ and filtered. The filtrate was concentrated under reduced pressure to provide the crude product, compound 9, as a pale yellow oil which was purified by flash chromatography on normal phase silica gel (40 gram column) using the following gradient program at 60 mL/min: 100% dichloromethane containing 0.5% triethylamine for 3 column volumes, then ramp to 5% MeOH-dichloromethane each containing 0.5% triethylamine over 20 column volumes, finally holding at 5% MeOH-Dichloromethane each containing 0.5% triethylamine for 5 column volumes. The column eluant was monitored at 285 nm and the fractions containing the purified material were pooled and concentrated under reduced pressure. The purified diamine compound 9 was obtained as a colorless oil that was further dried under high vacuum, and analyzed by LCMS (ESI) 443 [M+H]+.

Method 11 Preparation of Diamine Compound 10

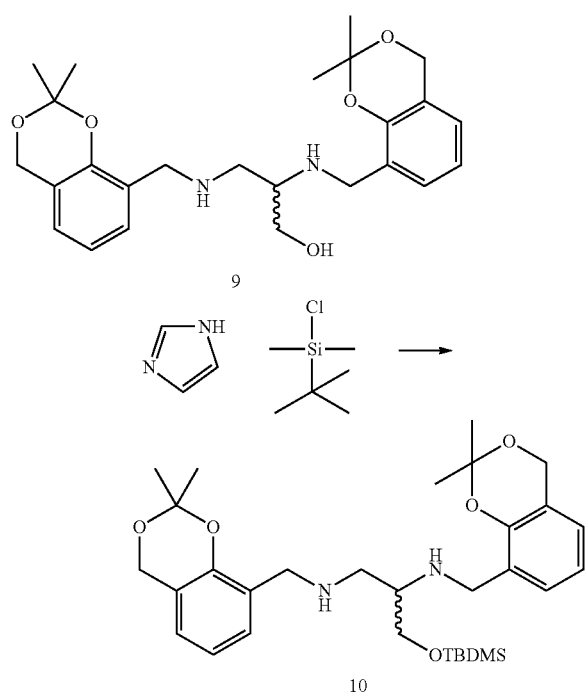

To a solution of the diamine compound 9 (0.95 g, 2.15 mmol) in anhydrous dichloromethane (21.5 mL) was added imidazole (0.6 g, 8.62 mmol) and tert-butyldimethylsilyl chloride (0.66 g, 4.3 mmol). The reaction mixture was stirred for 16 h at room temperature and then quenched with saturated aqueous sodium bicarbonate solution (25 mL). The aqueous and organic layers were separated and the aqueous layer was extracted with dichloromethane (3×25 mL). The combined organic layers were washed with saturated aqueous sodium bicarbonate solution, (2×25 mL), and brine, dried over MgSO4 and filtered. The filtrate was concentrated under reduced pressure to provide the crude product 10 as a oil which was purified by flash chromatography on normal phase silica gel (40 gram column) using the following gradient program at 40 mL/min: 100% dichloromethane containing 0.5% triethylamine for 2 column volumes, then ramp to 10% MeOH-Dichloromethane each containing 0.5% triethylamine over 20 column volumes, finally holding at 10% MeOH-Dichloromethane each containing 0.5% triethylamine for 4 column volumes. The column eluant was monitored at 285 nm and fractions containing the purified material were pooled, and concentrated under reduced pressure to yield purified tert-butyldimethylsilyl ether 10 as a colorless oil (1.11 g, 2.0 mmol, 93%) which was further dried under high vacuum and then analyzed by LCMS (ESI) 558 (M+H)+.

Example 2

Preparation of Ligand Precursor Compound XXVII

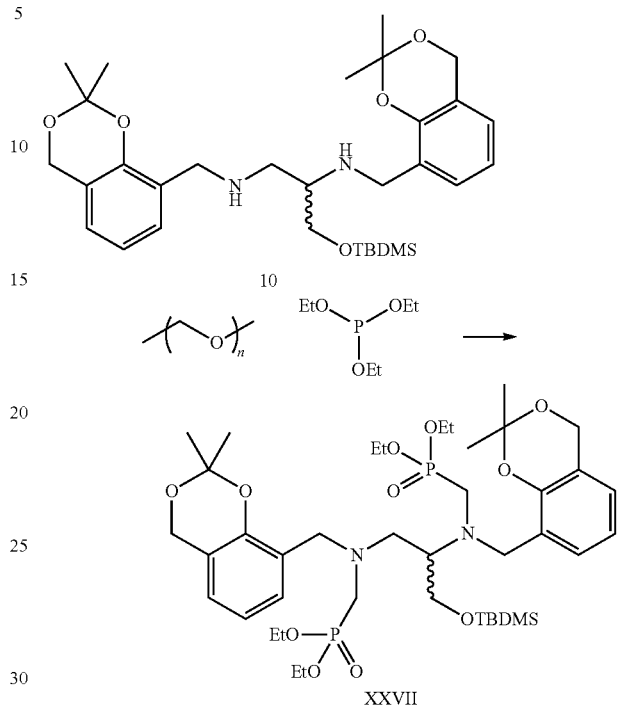

The diamine compound 10 (1.11 g, 1.99 mmol) was dissolved in a solution containing triethylphosphite (25 mL, 146 mmol) and chloroform (10 mL). Paraformaldehyde (0.5 g) was added to the reaction mixture and the mixture was heated and maintained at a temperature of 35° C. for 4 days. At the end of the stipulated time, the reaction mixture was checked by LCMS, which indicated that the reaction had not proceeded to completion. An aliquot (1 mL) from the reaction mixture was added to a microwave reaction vessel followed by addition of paraformaldehyde 100 mg. The mixture was subjected to microwave irradiation for 10 min at 85° C. Following the microwave irradiation, an additional portion of paraformaldehyde (100 mg) was added and the mixture was heated for 20 min at a temperature of 85° C. in the microwave. LCMS analysis of the reaction mixture, indicated further conversion to the product XXVII. Heating the aliquot for an additional 60 minutes at 100° C. under microwave irradiation resulted in complete conversion to product. The remainder of the reaction mixture was divided between 5 microwave tubes and each of the tubes was treated with paraformaldehyde (500 mg) and subjected to microwave heating at a temperature of 100° C. for 90 minutes to provide good conversion to the product XXVII. The tubes were pooled and concentrated under reduced pressure. The residue was co-evaporated with three portions of ethanol and placed under high vacuum overnight. The crude product was purified by flash chromatography on normal phase silica gel (120 gram column) using the following gradient program at 80 mL/min: 88% EtOAc-hexanes containing 0.5% triethylamine for 20 column volumes. The column eluant was monitored at 277 nm and the fractions containing the purified material were pooled and concentrated under reduced pressure. The purified compound XXVII was obtained as a colorless oil that was dried under high vacuum, and analyzed by LCMS (ESI) 857 [M+H]+, 879 [M+Na]+.

Example 3

Preparation of Compound XIX

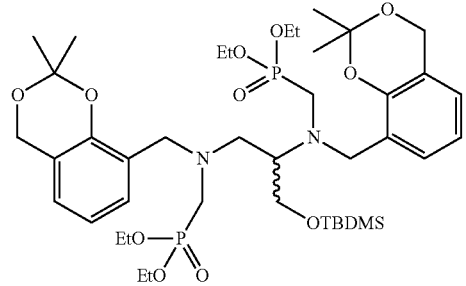

XXVII

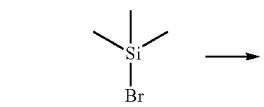

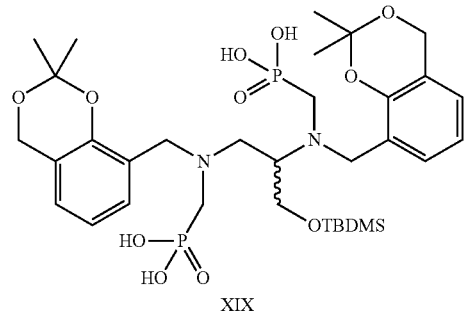

XIX

To a stirred solution of ligand precursor compound XXVII (0.26 g, 0.30 mmol) in dichloromethane (3.0 mL) at room temperature was added bromotrimethylsilane (0.20 mL, 1.5 mmol). The reaction mixture was stirred at room temperature and the progress of the reaction was monitored by LCMS. After 18 hours the reaction was deemed to be complete, the major product being bisphosphonic acid XIX which was free of the bisphosphonate starting material XXVII. The solvent was evaporated under reduced pressure and the residue further dried under high vacuum for 15 min to provide a colorless foam comprising the bisphosphonic acid XIX and lesser amounts of partially deprotected compounds XIXa, XIXb, XIXc, and XIXd. This crude product mixture was used immediately in the acid mediated deprotection-iron complexation protocol of Example 4.

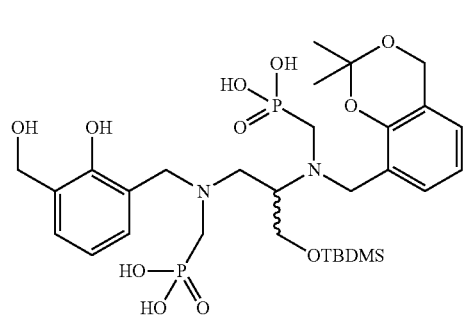

XIXa

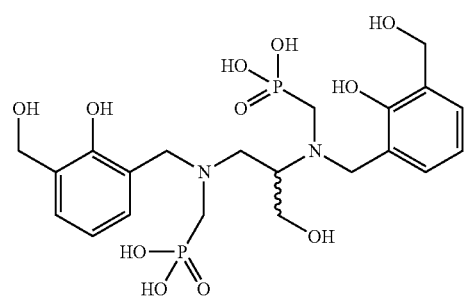

XIXb

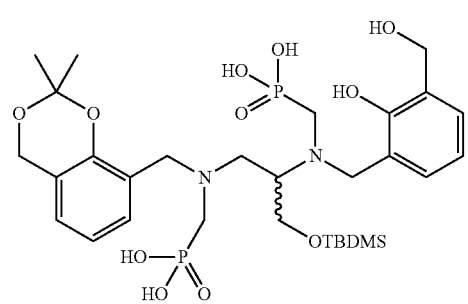

XIXc

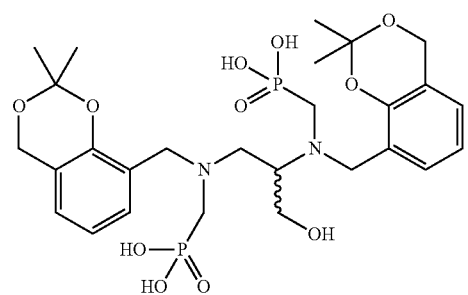

XIXd

Example 4

Preparation of FE Complex Compound V

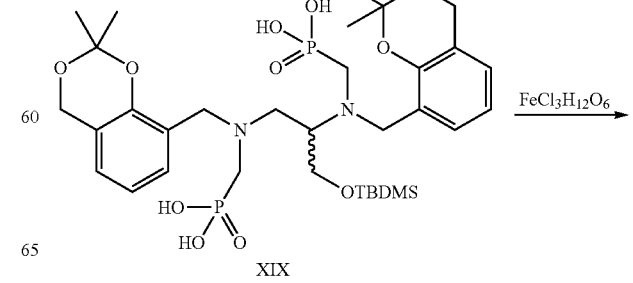

XIX

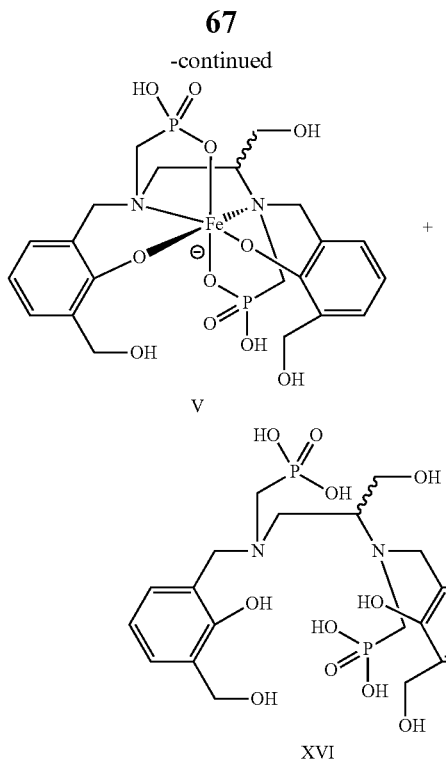

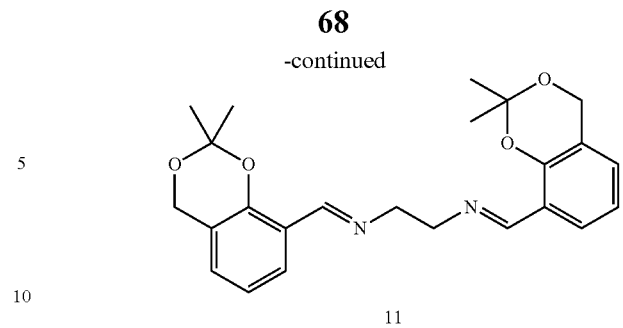

To ethylenediamine (126 μL, 1.88 mmol) in dichloromethane (5 mL) was added triethylamine (654 μL, 4.69 mmol) followed by MgSO$_4$ (903 mg, 7.5 mmol) and the resultant mixture was stirred for 1.5 h at room temperature. The aldehyde 6 (721 mg, 3.75 mmol) in dichloromethane (3 mL) was then added and the reaction mixture was stirred overnight. The reaction mixture was filtered and then concentrated under reduced pressure to provide the crude bisimine 11 containing a small quantity of unreacted aldehyde. The conversion of aldehyde to imine was confirmed by NMR spectroscopy: $^1$H NMR (CD$_2$Cl$_2$, 400 MHz) δ 1.54 (s, 12H), 3.94 (s, 4H), 4.87 (s, 4H), 6.92 (t, J=8 Hz, 2H), 7.05 (d, J=8 Hz, 2H), 7.82 (d, J=8 Hz, 2H), and 8.64 (s, 2H).

Method 13 Preparation of Diamine Compound 12

The crude product from Example 3 above comprising ligand XIX was dissolved in dioxane (1 mL) and water (1 mL) and FeCl$_3$ hexahydrate (88 mg, 0.26 mmol) was added followed by the addition of 4M HCl in dioxane (1 mL, 4 mmol). The reaction mixture was stirred at room temperature and progress of the reaction was monitored by LCMS. The reaction appeared to be complete after 2.5 hours. The reaction mixture was then quenched with excess saturated aqueous sodium carbonate solution and diluted with dichloromethane. The aqueous layer and the organic layers were separated. The aqueous layer (pH ~8) containing the product iron complex V was extracted with dichloromethane (2×20 mL) and was then filtered through a sintered glass funnel and further concentrated under reduced pressure to remove trace volatiles. Iron complex V was obtained as a deep red solution (approximately 30 mL) which was filtered through a 30000 MWCO filter and analyzed by LCMS (ESI) 602 (M–H)$^-$ V, $\lambda_{max}$ (DI)=466 nm.

Method 12 Preparation of Compound 11

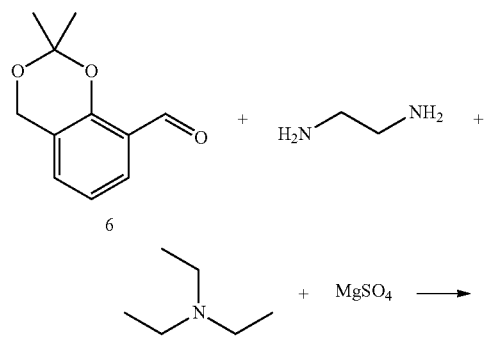

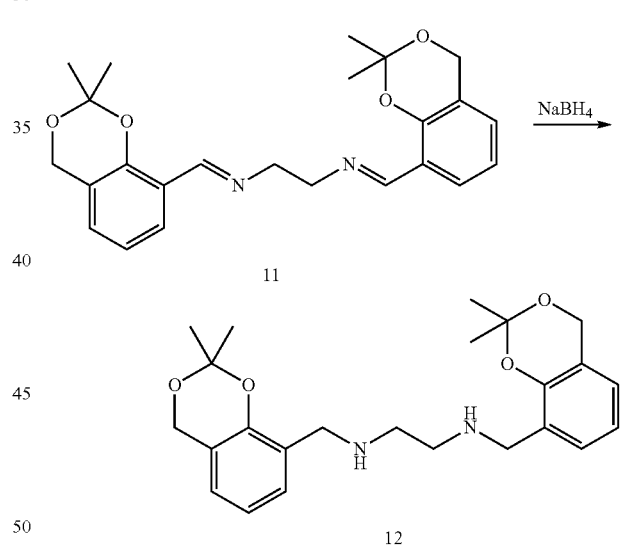

To a solution of bisimine 11 (700 mg, 1.71 mmol) in dichloromethane (6.8 mL) and methanol (1.7 mL) at 0° C. was added sodium borohydride powder (259 mg, 6.85 mmol). The reaction mixture was allowed to stir overnight while slowly warming to room temperature and was then diluted with saturated aqueous sodium carbonate solution. The aqueous and organic layers were separated. The aqueous layer was extracted with dichloromethane (3×25 mL). The combined organic layers were washed with saturated aqueous sodium bicarbonate solution (2×25 mL) and brine (2×25 mL), dried over Na$_2$SO$_4$ and filtered. The filtrate was concentrated under reduced pressure to provide the crude product 12 as a pale yellow oil. The crude product 12 was purified by flash chromatography on normal phase silica gel (40 gram column) using the following gradient program at 40 mL/min: 100% dichloromethane containing 0.5% triethylamine for 3 column volumes, then ramp to 5% MeOH-dichloromethane each containing 0.5% triethylamine over 20 column volumes, finally holding at 5% MeOH-dichloromethane each containing 0.5% triethylamine for 5 column volumes. The column eluant was monitored at 285 nm and fractions containing the purified material were combined, concentrated under reduced pressure and dried under high vacuum to yield the purified compound 12 as a colorless oil. The purified compound 12 was analyzed by NMR spectroscopy and mass spectrometry. $^1$H NMR (CD$_2$Cl$_2$, 400 MHz) δ 1.57 (s, 12H), 1.86 (br s, 2H), 2.73 (s, 4H), 3.78 (s, 4H), 4.88 (s, 4H), 6.88-6.94 (m, 4H), and 7.19 (m, 2H); m/z=414 [M+H]$^+$.

Example 5

Preparation of Ligand Precursor Compound XXX

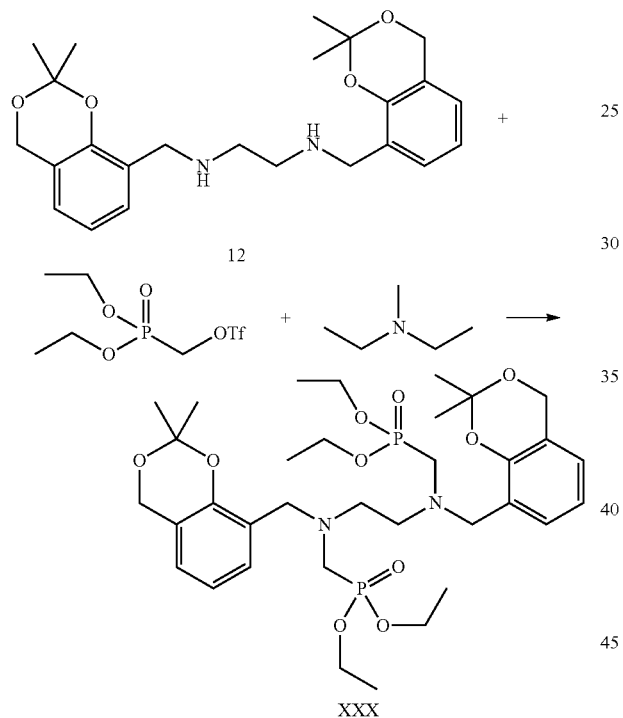

To a solution of diamine compound 12 (486 mg, 1.18 mmol) in anhydrous THF (12 mL) at 0° C. was added triethylamine (658 μL, 4.72 mmol) followed by dropwise addition of (diethoxyphosphoryl)methyl trifluoromethanesulfonate (1.08 g, 3.60 mmol). The reaction mixture was allowed to warm to room temperature and stirred overnight. The reaction mixture was then quenched with saturated aqueous sodium carbonate solution. The aqueous and organic layers were separated and the aqueous layer was extracted with dichloromethane (3×25 mL). The combined organic layers were washed with saturated aqueous sodium bicarbonate solution (2×25 mL) and brine (2×25 mL), dried over Na$_2$SO$_4$ and filtered. The filtrate was concentrated under reduced pressure to provide the crude product as a pale yellow oil which was purified by flash chromatography on normal phase silica gel (40 gram column) using the following gradient program at 40 mL/min: ramp from hexanes containing 0.5% triethylamine to 75% ethyl acetate-hexanes each containing 0.5% triethylamine over 2 column volumes, then ramp to 95% ethyl acetate-hexanes each containing 0.5% triethylamine over 13 column volumes, finally holding at 95% ethyl acetate-hexanes each containing 0.5% triethylamine for 10 column volumes. The column eluant was monitored at 285 nm and fractions containing the purified material were combined and concentrated under reduced pressure to yield purified compound XXX as a colorless oil after drying under high vacuum. The structure of compound XXX was confirmed by NMR spectroscopy and LCMS. $^1$H NMR (CD$_2$Cl$_2$, 400 MHz) δ 1.29 (t, J=8 Hz, 12H), 1.53 (s, 12H), 2.87 (s, 4H), 2.94 (d, J=8 Hz, 4H), 3.75 (s, 4H), 4.03-4.12 (m, 8H), 4.85 (s, 4H), 6.86-6.91 (m, 4H), and 7.30 (d, J=8 Hz, 2H); LCMS m/z=714 [M+H]$^+$, 736 [M+Na]$^+$.

Example 6

Preparation of Compound XXXI

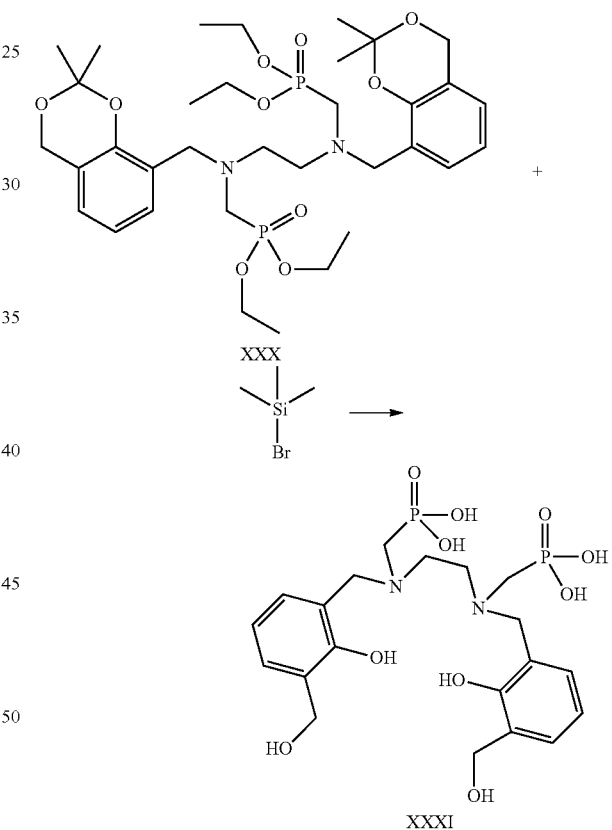

To a stirred solution of compound XXX (157 mg, 0.22 mmol) in of anhydrous dichloromethane (7.0 mL) and anhydrous acetonitrile (7.0 mL) was added bromotrimethylsilane (0.40 mL, 3.09 mmol) at room temperature. The reaction mixture was then heated at 50° C. for 30 hours. The solvent was removed under reduced pressure and the residue was stirred overnight in an acetone:water mixture (4:1 v/v) at room temperature. The resulting suspension was subjected to centrifugation and the precipitate was washed with water and acetone to afford ligand XXXI as a colorless solid which was used immediately in Example 7 below.

Example 7

Preparation of Compound IV

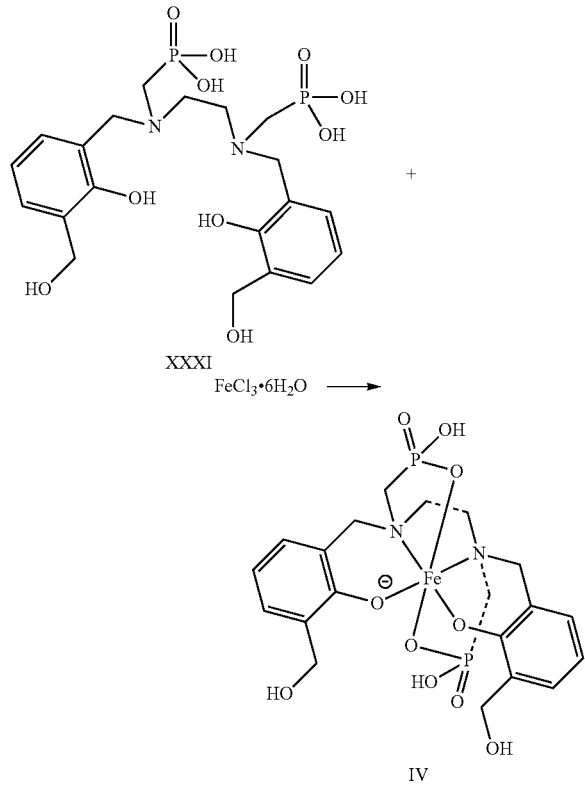

Ligand XXXI prepared in Example 6 above was suspended in 3 mL of water and a solution of FeCl₃ hexahydrate (76 mg, 0.29 mmol) was added. The resultant mixture was stirred at 50° C. and progress of the reaction was monitored by LCMS. Upon completion of the reaction, the pH of the reaction mixture was adjusted to 5 by the addition of N-methyl-D-glucamine. Iron complex IV was obtained as a precipitate which was collected by centrifugation, washed twice with water, and then resuspended in water. Additional N-methyl-D-glucamine was then added to adjust the pH to 9. The resulting red solution was filtered through a 0.1 μm syringe filter and analyzed by LCMS to confirm the presence of iron complex IV, m/z=572 [M]⁺, $\lambda_{max}$ (DI)=465 nm.

Method 14 Preparation of Imine Compound 13

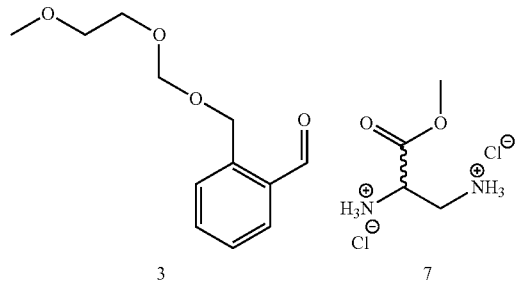

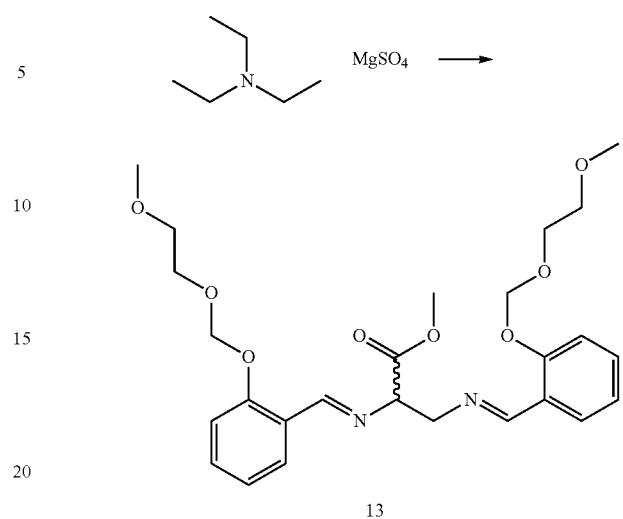

To a suspension of MgSO₄ (2.38 g, 19.8 mmol) in dichloromethane (17 mL) was added triethylamine (3.1 mL, 22.3 mmol). The diamine compound 7 (945 mg, 5.0 mmol) was then added as a powder. The suspension was stirred at room temperature for 1 hr, followed by the addition of the aldehyde compound 3 (2.08 g, 9.9 mmol) in dichloromethane (3 mL). The reaction mixture was allowed to stir overnight. As the imine product is highly sensitive to hydrolysis care to exclude water from the workup and chromatographic steps were avoided. Following this time, the reaction mixture was filtered to remove solid materials. The filtrate was concentrated under reduced pressure to a solid material, which was triturated with anhydrous ethyl ether and filtered. The filtrate was concentrated under reduced pressure to obtain the compound 13 as a yellow oil, which was dried in vacuum overnight. ¹H NMR (CD2Cl2, 400 MHz) δ 3.33 (s, 6H), 3.50 (t, J=4 Hz, 4H), 3.56 (m, 1H), 3.75 (m, 4H), 3.79 (s, 3H), 3.89 (m, 2H), 4.31 (m, 1H), 4.43 (m, 1H), 5.26 (s, 4H), 7.03 (m, 2H), 7.16 (t, J=8 Hz, 2H), 7.39 (m, 2H), 7.94 (dd, J1=8 Hz, J2=8 Hz, 2H), and 8.71 (d, J=8 Hz, 2H).

Method 15 Preparation of Compound 14

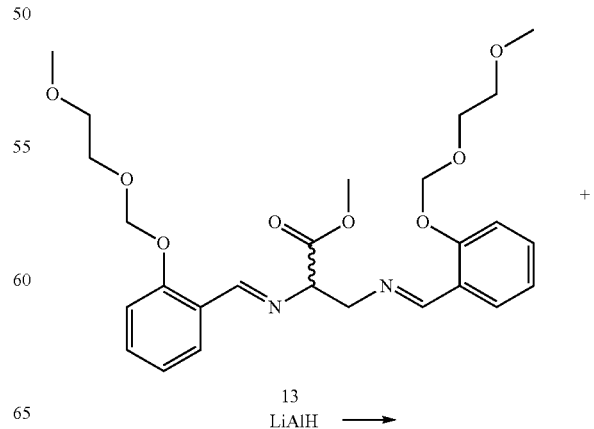

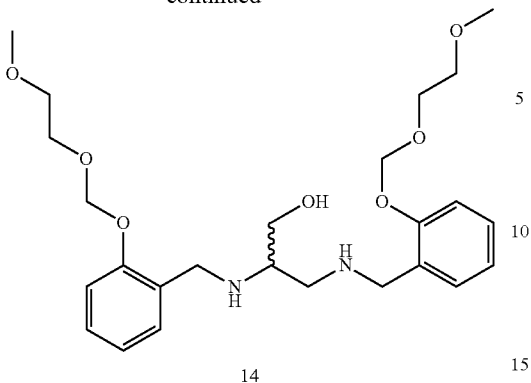

14

Lithium aluminum hydride (760 mg, 19.8 mmol) as a powder was added to a solution of the compound 13 in tetrahydrofuran (50 mL) at 0° C. under stirring conditions. The stirring was continued, while slowly warming the reaction mixture to room temperature overnight followed by dropwise addition of water at 0° C. to quench the reaction mixture. The reaction mixture was stirred for 1 hr, the resulting solid was filtered and diluted with dichloromethane. The aqueous and organic layers were separated and the aqueous layer was extracted with dichloromethane (3×25 mL). The combined organic layers were washed with water (1×25 mL), brine (1×25 mL), and dried over $Na_2SO_4$ and filtered. The filtrate was concentrated under reduced pressure to provide the crude product as a pale yellow oil which was purified by flash chromatography on normal phase silica gel (40 gram column) using the following gradient program at 40 mL/min: 100% dichloromethane w/0.3% triethylamine for 2 column volumes, then ramp to 20% MeOH-dichloromethane each w/0.3% triethylamine over 20 column volumes, finally holding at 20% MeOH-dichloromethane each w/0.3% triethylamine for 2 column volumes. The column eluant was monitored at 254 nm and fractions containing the purified material were combined and concentrated under reduced pressure to give the compound 14 as a colorless oil (1.08 g, yield 46% based on the 2 steps). $^1$H NMR (CD2Cl2, 400 MHz) δ 2.75-2.8 (m, 3H), 2.85-3.1 (br s, 2H), 3.34 (s, 6H), 3.50-3.58 (m, 5H), 3.66-3.76 (m, 1H), 3.76-3.82 (m, 8H), 5.28 (s, 2H), 5.29 (s, 2H), 6.99 (t, J=8 Hz, 2H), 7.13 (dd, J1=8 Hz, J2=1.6 Hz, 2H), and 7.21-7.31 (m, 4H); m/z=479 [M+H]+, 501 [M+Na]+.

Example 8

Preparation of Compound XXXII

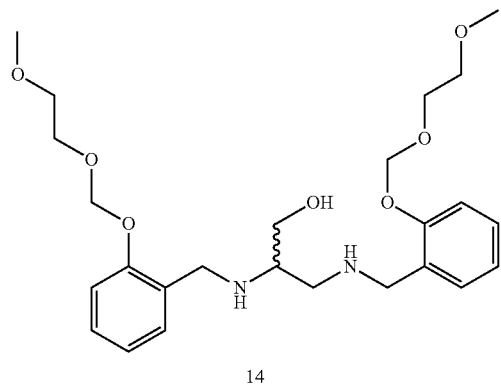

14

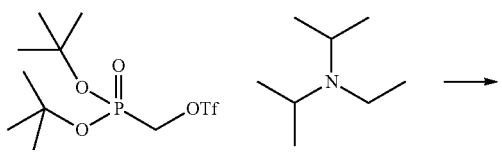

XXXII

To a solution of diamine compound 14 (316 mg, 0.66 mmol) in anhydrous acetonitrile (3 mL) at 0° C. was added triethylamine (570 µL, 3.3 mmol) followed by dropwise addition of (di-tert-butoxyphosphoryl)methyl trifluoromethanesulfonate (610 mg, 1.45 mmol) in acetonitrile (0.5 mL). The reaction mixture was allowed to warm to room temperature and stirred overnight. Following this acetonitrile was removed under high pressure, and dichloromethane was added to dissolve the residue. The organic layer was washed with saturated aqueous potassium carbonate solution (2×25 mL), brine (1×25 mL), dried over $Na_2SO_4$, and filtered. The filtrate was concentrated under reduced pressure to provide the crude product as a pale yellow oil, which was purified by flash chromatography (SiO2, 40 gram column) to give the compound XXXII as a colorless oil (580 mg, yield: 100%). 1H NMR (CD2Cl2, 400 MHz) δ 1.43-1.47 (m, 36H), 2.57 (d, J=12 Hz, 1H), 2.73 (d, J=12 Hz, 1H), 2.82 (t, J=12 Hz, 1H), 2.91-2.96 (m, 2H), 3.02 (t, J=12 Hz, 1H), 3.14-3.22 (m, 1H), 3.34 (s, 3H), 3.35 (s, 3H), 3.44-3.54 (m, 6H), 3.65-3.87 (m, 6H), 3.96 (d, J=8 Hz, 2H), 4.3-4.4 (m, 1H), 5.2 (s, 2H), 5.26 (d, J=4 Hz, 2H), 6.94-7.05 (m, 2H), 7.08-7.13 (m, 2H), 7.15-7.24 (m, 2H), 7.44 (d, J=8 Hz, 1H), and 7.68 (d, J=8 Hz, 1H); LCMS m/z=891 [M+H]+, 913 [M+Na]+.

Example 9

Preparation of Compound XXXIII

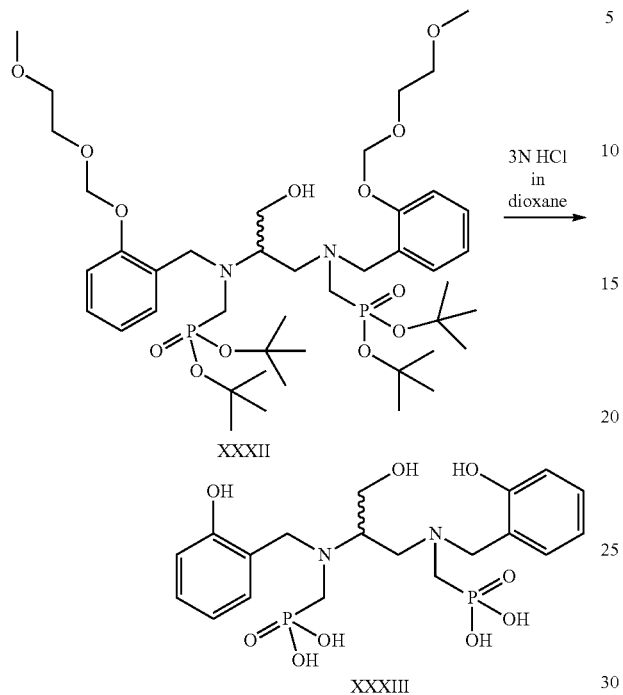

To a solution of compound XXXII (430 mg, 0.48 mmol) in 7.2 mL of dioxane at 0° C. in an ice bath, 2.4 mL of 4 N HCl in dioxane was added. Following the addition, the ice bath was quickly removed, and the colorless solution was stirred at room temperature for 2 hrs. Anhydrous diethyl ether was added, and the mixture was subjected to ultrasound treatment for a few minutes. The resulting suspension was then subjected to centrifugation and the precipitate was washed with ether. The white solid that was obtained was dissolved in 2 mL of water and lyophilized to give the compound XXXIII as a white powder, which was used directly for the next step without further purification. LCMS m/z=491 [M+H]$^+$

Example 10

Preparation of Compound VI

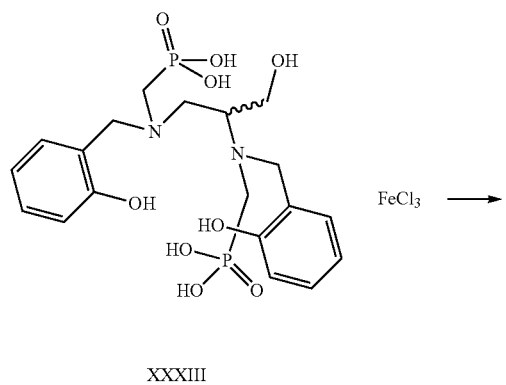

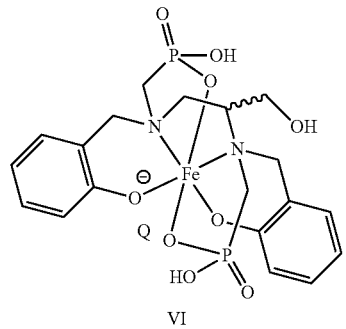

A solution of FeCl$_3$ (85 mg, 0.53 mmol) was added to a suspension of compound XXXIII in 4 mL of water. The reaction mixture was stirred until a rose colored solution was formed. The pH of the solution was adjusted to 5 by adding N-methyl-D-glucamine (400 mg, 1.55 mmol). The resulting purple precipitate was collected by centrifugation, washed with water (3 mL), and suspended in 5 mL of water. Following this, N-methyl-D-glucamine (250 mg, 1.30 mmol) was added to adjust the pH of the solution to 9 and yield compound VI as a clear red solution. UV-V is [DI] $\lambda_{max}$=461 nm. m/z=542 [M]+.

Relaxivity Determinations

A stock solution having a concentration of 1 mM of the contrast enhancement agent was prepared in phosphate buffered saline (PBS) and the iron concentration was verified by elemental analysis. Separate 0.75 mM, 0.50 mM and 0.25 mM samples were prepared from the stock by dilution in PBS and the T$_1$ and T$_2$ relaxations times were recorded in triplicate for each sample on a Bruker Minispec mq60 instrument (60 MHz, 40° C.). The relaxivities (r$_1$ and r$_2$) were obtained as the gradient of 1/T$_x$ (x=1, 2) plotted against Fe chelate concentration following linear least squares regression analysis. Data for contrast enhancement agents having structures IV, V, VI and VII, and non-hydroxylated control samples (CEx.1, CEx.2 and CEx.3). Data are gathered in Table 8 below and illustrate the surprising effect of phosphorylation and hydroxylation on the relaxivities exhibited by the contrast enhancement agents provided by the present invention relative to the control samples (CEx.1-CEx.3).

TABLE 8

Relaxivities, and Protein and Bone Binding Affinities of Representative Contrast Enhancement Agents

| Chelate Structure | | $r_1$(mM$^{-1}$·s$^{-1}$) 1.4T, PBS | $r_2$(mM$^{-1}$·s$^{-1}$) 1.4T, PBS | 1 hr Protein Binding | 24 hr Bone Binding |
|---|---|---|---|---|---|
| Control (CEx. 1) | [structure] | 0.5 | 0.5 | 33 | NM* |
| Control (CEx. 2) | [structure] | 1.3 | 1.5† (1.6) | 49 | 38 |
| Control (CEx. 3) | [structure] | 0.9 | 1.0 | 0 | 16 |
| IV | [structure] | 0.9 | 1.2 | 20 | 5 |

TABLE 8-continued

Relaxivities, and Protein and Bone Binding Affinities of Representative Contrast Enhancement Agents

| Chelate Structure | $r_1(mM^{-1} \cdot s^{-1})$ 1.4T, PBS | $r_2(mM^{-1} \cdot s^{-1})$ 1.4T, PBS | 1 hr Protein Binding | 24 hr Bone Binding |
|---|---|---|---|---|
| V | 1.5† (1.8) | 1.7† (1.9) | 20 | 12 |
| VI | 0.9 | 1.3 | 44 | 40 |
| VII | 1.2 | 1.4 | 43 | 18 |

*NM = Not Measured,
†Revised value provided here relative to original value reported in related U.S. application Ser. No. 12/751286 as a result of additional measurements, (original value).

Ascorbic Acid Oxidation Assay

The UV-Vis spectrum of an ascorbic acid solution (67 µM, 12 µg·mL-1) in phosphate buffered saline (PBS) (3 mL) was recorded. The absorbance intensity at $\lambda_{max}$=265 nm was observed. An aliquot (30 µL) of iron chelate of ethylenediaminetetraacetic acid (FeEDTA) in PBS (2 mM, 0.7 mg·mL-1) was added to afford a catalytic quantity of FeEDTA (20 µM, 30 mol %) with respect to ascorbic acid. The absorbance intensity ($\lambda_{max}$=265 nm) was recorded at intervals of 1 minute for a period of 45 minutes and the data normalized to the $t_0$ absorbance. The experiment was then repeated identically using iron chelate complex FeHBEDP(OH)$_3$ (20 µM, 30 mol %). It is observed from FIG. 1 that the coordinately unsaturated Fe complex (FeEDTA) consumes ascorbic acid completely whereas the coordinately saturated Fe complex, (FeHBEDP(OH)$_3$) exhibits negligible consumption of ascorbic acid under identical conditions. This suggests the iron complexes of the present invention are REDOX stable and would be unlikely in vivo to generate reactive oxygen species via Fenton chemistry, thereby providing an additional level of certainty with respect to the agent's safety in human subjects.

Protein Binding Assay

Figure 2:
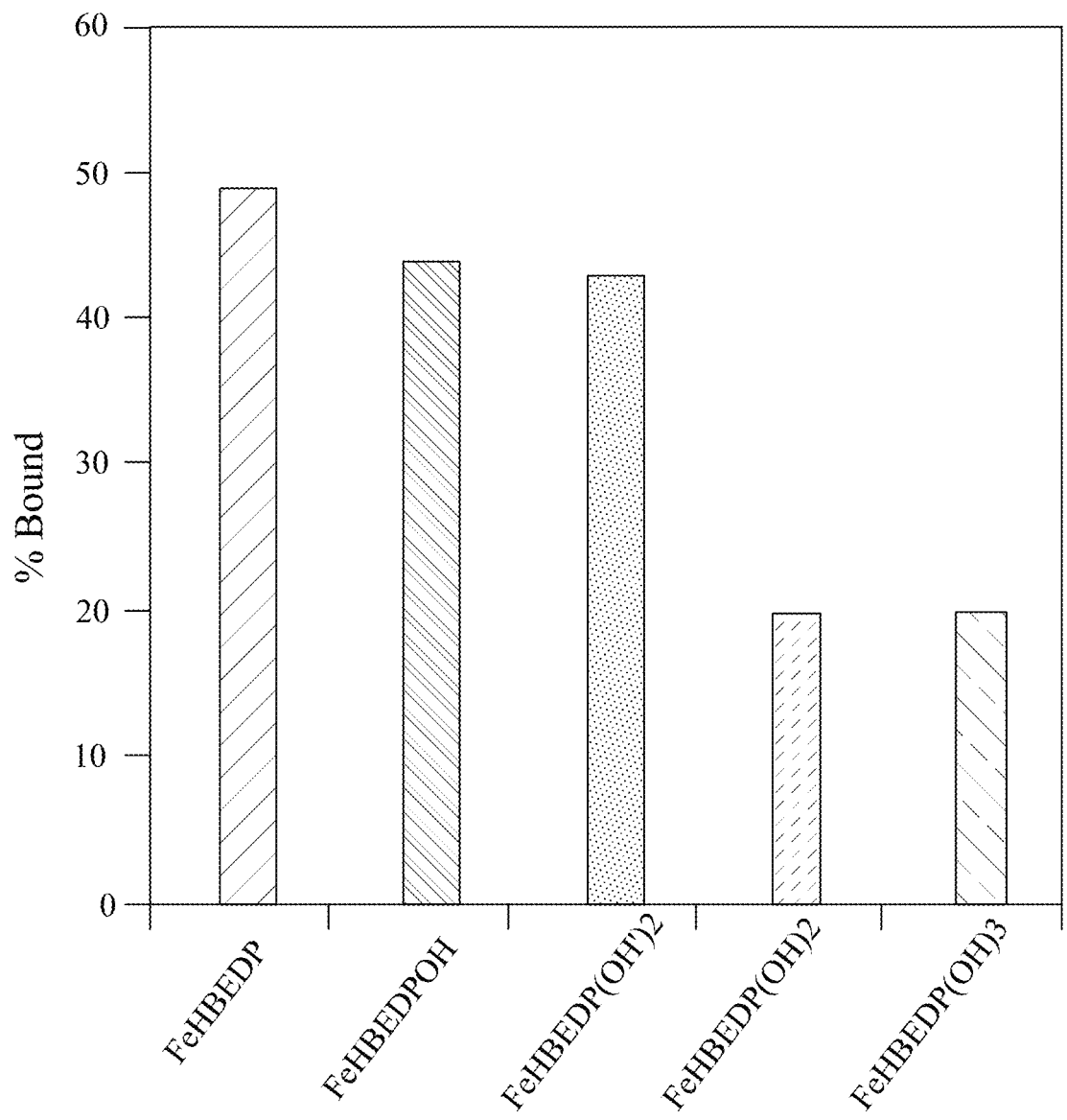
FIG. 2 is a graphical representation of the effect of hydroxylation on iron chelate (1 mM [Fe]) protein binding in accordance with an embodiment of the invention.

A 5 mM stock solution of the FeHBEDP(OH)$_3$ (the iron chelate having structure V) was prepared in phosphate buffer saline (PBS) and the UV-Vis spectrum recorded. The wavelength and intensity of the absorbance maximum ($\lambda_{max}$) in the visible region was recorded. An aliquot of the FeHBEDP (OH)$_3$ stock (500 uL) solution was added to a PBS solution (2 mL) containing bovine serum albumin (BSA) (8 wgt. %). A control sample was prepared by diluting a second aliquot (500 uL) of the FeHBED(OH)$_3$ stock with PBS (2 mL). The samples were vortexed briefly and then allowed to sit for 1 hour. At the stipulated time the resulting pale red solutions were transferred to Amicon Ultra filters (4 ml, MWCO=30 KDa). The solutions were centrifuged (3000 rcf, 15 minutes) and the permeate was taken directly for UV-Vis measurement. The wavelength and intensity of the $\lambda_{max}$ in the visible region for the solution were recorded. The relative amount of free and protein-bound FeHBEDP(OH)$_3$ was calculated from the $\lambda_{max}$ intensity ratio of the assay to control samples. From FIG. 2 it may be observed that the polyhydroxylated Fe complex (FeHBEDP(OH)$_3$) has significantly lower protein binding than the parent non-hydroxylated Fe complex (FeHBEDP) (CEx.2). As shown in Table 8 the Fe complexes having structures VI and VII have slightly lower protein binding affinities than the parent non-hydroxylated Fe complex (FeHBEDP) (CEx.2), while having higher protein binding affinities than the polyhydroxylated Fe complexes having structures IV and V. Protein binding behavior appears to be dependant on the degree and position of hydroxylation. Hydroxylation of aromatic carbon atoms appears to have an important impact on the agent's affinity for protein.

Hydroxy Apatite (Bone) Binding Assay

Figure 3:
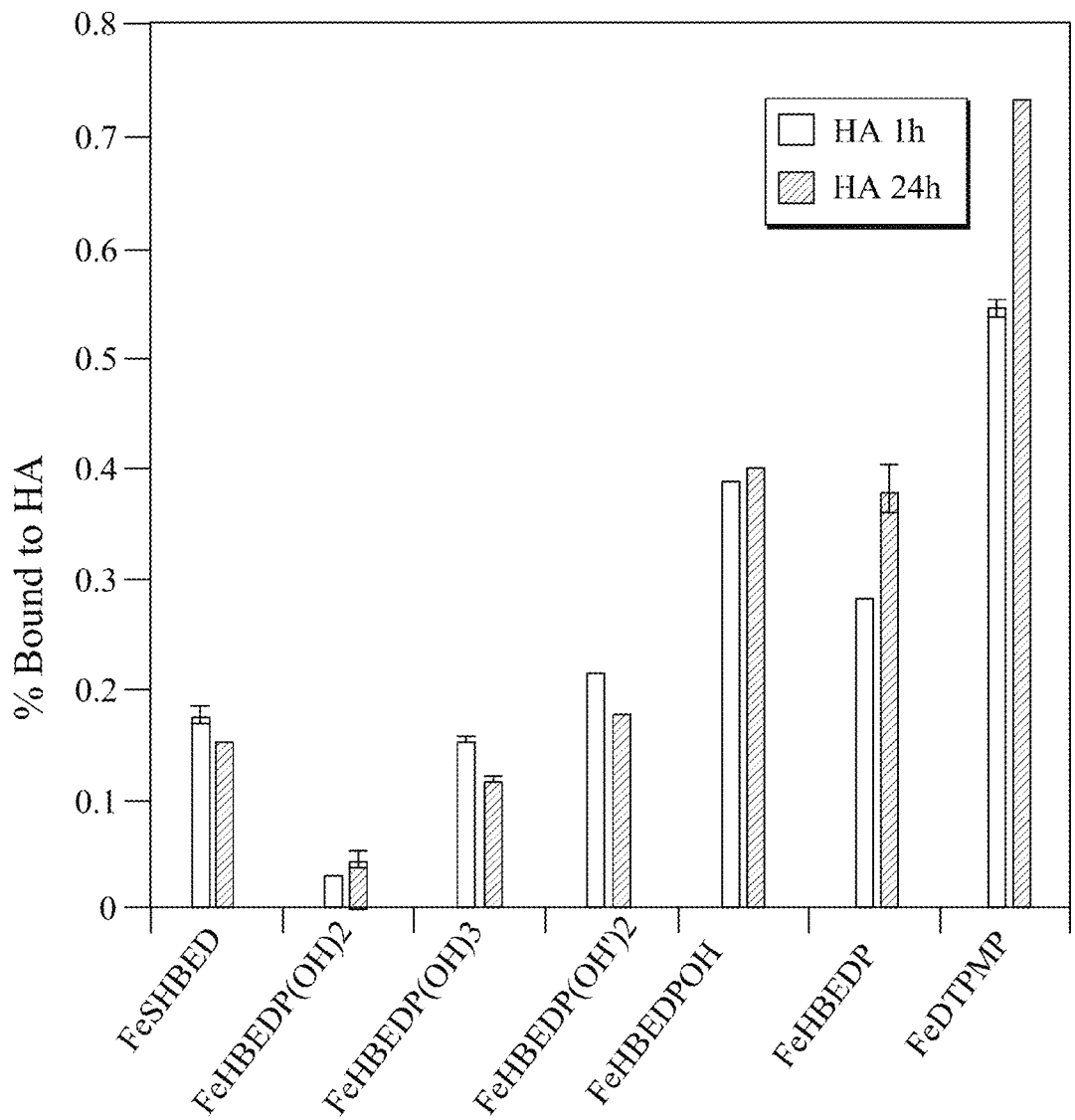
FIG. 3 is a graphical representation of the binding affinity of iron chelates (2 mM [Fe]) for type I hydroxy-apatite (HA) in accordance with an embodiment of the invention.

A 2 mM stock solution of the iron compound of structure V (FeHBEDP(OH)$_3$) was prepared in deionized water and the UV-Vis spectrum was recorded. The wavelength and intensity of the absorbance maximum ($\lambda_{max}$) in the visible region were noted. Hydroxyapatite type 1 (HA, obtained from Sigma Aldrich) was washed with deionized water and the solid was isolated by centrifugation at 3000 rcf, for 15 min, followed by decanting of the aqueous solution. The remaining slurry was allowed to dry and a portion of the resulting white solid (250 mg) was combined with the 2 mM solution of FeHBEDP (OH)$_3$ (2 mL) in an Eppendorf tube. A control solution of a stock solution containing the iron chelate having structure V (FeHBEDP(OH)$_3$) (2 mL, 2 mM) was prepared in a second Eppendorf tube. Aliquots (200 uL) of the assay and control solutions were diluted with deionized water (1.8 mL) after a period of 1 h and 24 h. The UV-Vis spectra were recorded, and the wavelength and intensity of the λmax in the visible region were observed. The λmax intensity ratio of the assay to control samples having no hydroxy apatite was then calculated to estimate the relative amounts of free and bound FeHBEDP (OH)$_3$ at each timepoint. The following chelates were evaluated: FeSHBED (CEx. 3, a control containing no phosphonate groups), FeDTPMP (CEx.4, a control bearing multiple phosphonates), FeHBEDP (CEx.2); and the polyphosphonate containing Fe chelates of the invention having structures IV, V, VI and VII. It was observed that the polyphosphonate containing Fe chelates provided by the present invention generally demonstrated weaker binding affinity for HA (which is taken as a measure of bone binding affinity) relative to the control samples (See Table 8 and FIG. 3). Unaccountably, the iron chelate having structure VI displayed a relatively high bone binding affinity. It is noteworthy that the data for iron chelates IV-VII suggests that a greater number of hydroxyl groups reduces the overall bone binding affinity relative to an unhydroxylated FeHBEDP).

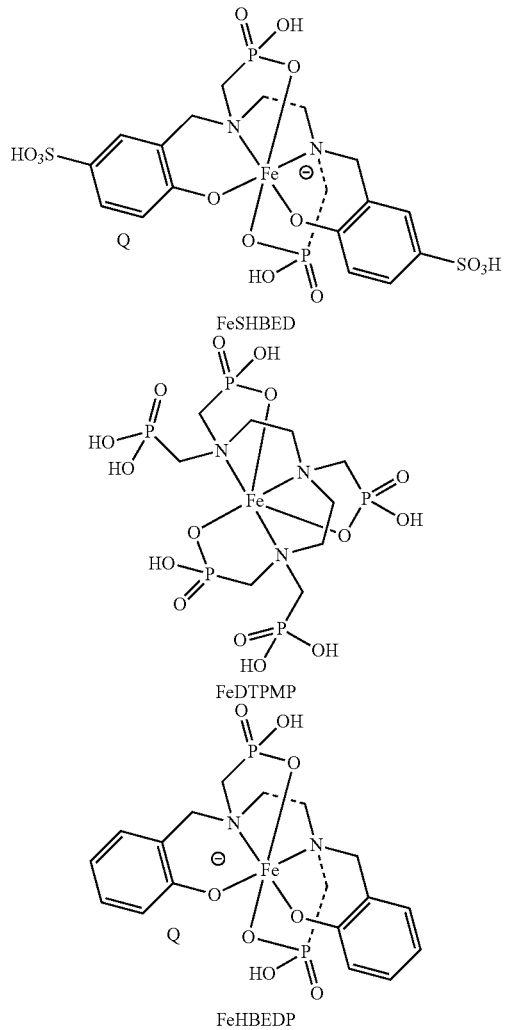

FeSHBED

FeDTPMP

FeHBEDP

Tumor Imaging

Cell Preparation: C6 glioma cells (available from ATCC™) were trypsinized using 1× trypsin-EDTA. The cells were washed using IX phosphate buffered saline (PBS) and aliquots of 2×10$^6$ cells were made in 1×PBS (100 uL). Prior to injection into the subject, 50 µL of basement membrane matrix (Matrigel™, BD Biosciences) was added to each aliquot.

Tumor Induction: All procedures involving animals were completed under protocols approved by the GE Global Research Institutional Animal Care and Use Committee. Female, 10-12 weeks old, CD1-nude mice (Charles River Laboratories) were briefly anesthetized with 2% isoflurane and injected with 2×10$^6$ C6 glioma cells in 1×PBS (100 µL) and Matrigel SC to their left flank. The animals were monitored for 7 days post tumor cell injections at which point, precontrast agent MR images of the resulting lesions, typically 1 cm in diameter, were collected using the FSPGR sequence described below.

Imaging: All imaging was performed on a GE Signa 1.5T clinical MR scanner, equipped with a 5 cm diameter custom solenoid RF receiver coil positioned at the center of the scanner bore. The animals were injected with a medical formulation comprising FeHBEDPOH (the iron chelate having structure VI, Q=protonated meglumine) (0.3 mmol·kg-1 [Fe], 75 mM, ~100 µL), through the tail vein prior to imaging. After administration of the medical formulation, the animals were immediately anesthetized using 2% isoflurane anesthesia and placed in the RF receiver coil. A series of 2D fast spoiled gradient echo (FSPGR) imaging sequences were collected (TE=3.9 ms, TR=150 ms, FA=90°, NEX=5, Freq./Phase=256×192, slice thickness=1 mm, FOV=5 cm) at the following timepoints: 5 minutes, 10 minutes, 15 minutes, 30 minutes, 2 hours, and 24 hours. Imaging slices sampling the kidney and liver, in addition to the whole tumor, were collected with a total acquisition time of 4 minutes per series.

Image Analysis: Post imaging analysis was performed using a Cine custom software tool (CineTool v8.0.9, GE Healthcare) built upon the IDL platform (IDL v. 6.3, ITT Corp., Boulder, Colo.). Regions of Interest (ROIs) were drawn manually and the intensities normalized to internal corn oil phantoms for comparison to the precontrast MR images.

In addition to iron chelate VI (FeHBEDPOH), image data was collected for a series of iron chelate contrast enhancement agents including FeHBEDP, iron chelate IV (FeHBEDP(OH)$_2$), and iron chelate V (FeHBEDP(OH)$_3$). The iron chelates FeHBEDPOH, FeHBEDP(OH)$_2$ and FeHBEDP(OH)$_3$ can be viewed as hydroxylated variants of parent iron chelate FeHBEDP and are referred to collectively herein as the FeHBEDP(OH)$_x$ series (where the subscript x includes 0, 1, 2 and 3). Hydroxylation in the FeHBEDP(OH)$_x$ series was found to alter the relative physiochemistry and resulting imaging efficacy of contrast enhancement agents in this series. Progressive hydroxylation of the parent iron chelate FeHBEDP reduced and ultimately significantly inhibited in-vitro residual hydroxy apatite binding in a non-regiospecific manner. The elimination or reduction of bone binding affinity is believed to limit in-vivo bone retention and thereby improve the overall agent safety profile via more rapid elimination.

Agent hydroxylation was also found to reduce protein binding in a regiospecific manner and to alter the in-vivo agent distribution behavior, as established by magnetic resonance imaging (MRI). Aromatic hydroxymethylation lead to a 60% reduction in protein binding in-vitro and enhanced elimination of the agents via the kidneys, as determined by strong MR enhancement of the kidney and bladder images with no significant liver image enhancement. However, in the cases of FeHBEDP and FeHBEDPOH, where the aromatic rings were not hydroxylated, the level of in-vitro protein binding was significantly higher and an initial MR enhancement of the liver image was observed, in addition to strong enhancement of the kidney and bladder images. For all agents, the tissue image enhancement decreased over the course of two hours until enhancement was observed only in the bladder. A follow up MR scan at 24 h post agent injection revealed tissues had returned to background levels of enhancement and suggested elimination of essentially all of the administered MR contrast enhancement agent.

Figure 4:
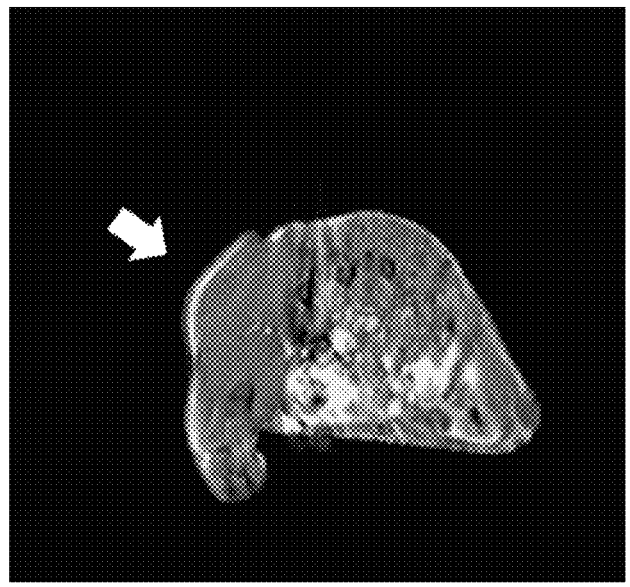
FIG. 4 illustrates tumor image contrast enhancement in accordance with an embodiment of the invention.
Figure 4:
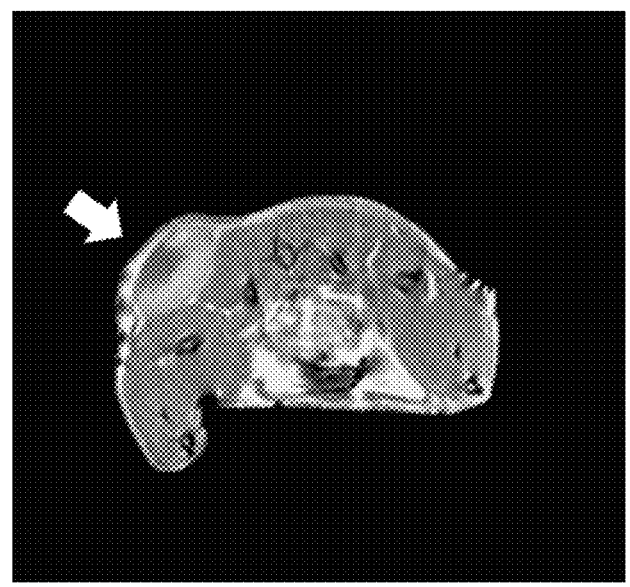

FIG. 4 illustrates T1-weighted MR images before ("PRE") administering and five minutes post injection ("POST") of the FeHBEDPOH MR contrast agent (0.3 mmol·kg$^{-1}$) in a C6-glioma-bearing mouse model described above. The C6 glioma lesion (tumor), marked by the arrows, is strongly enhanced when compared to the surrounding muscle tissue or the precontrast image.

Figure 5:
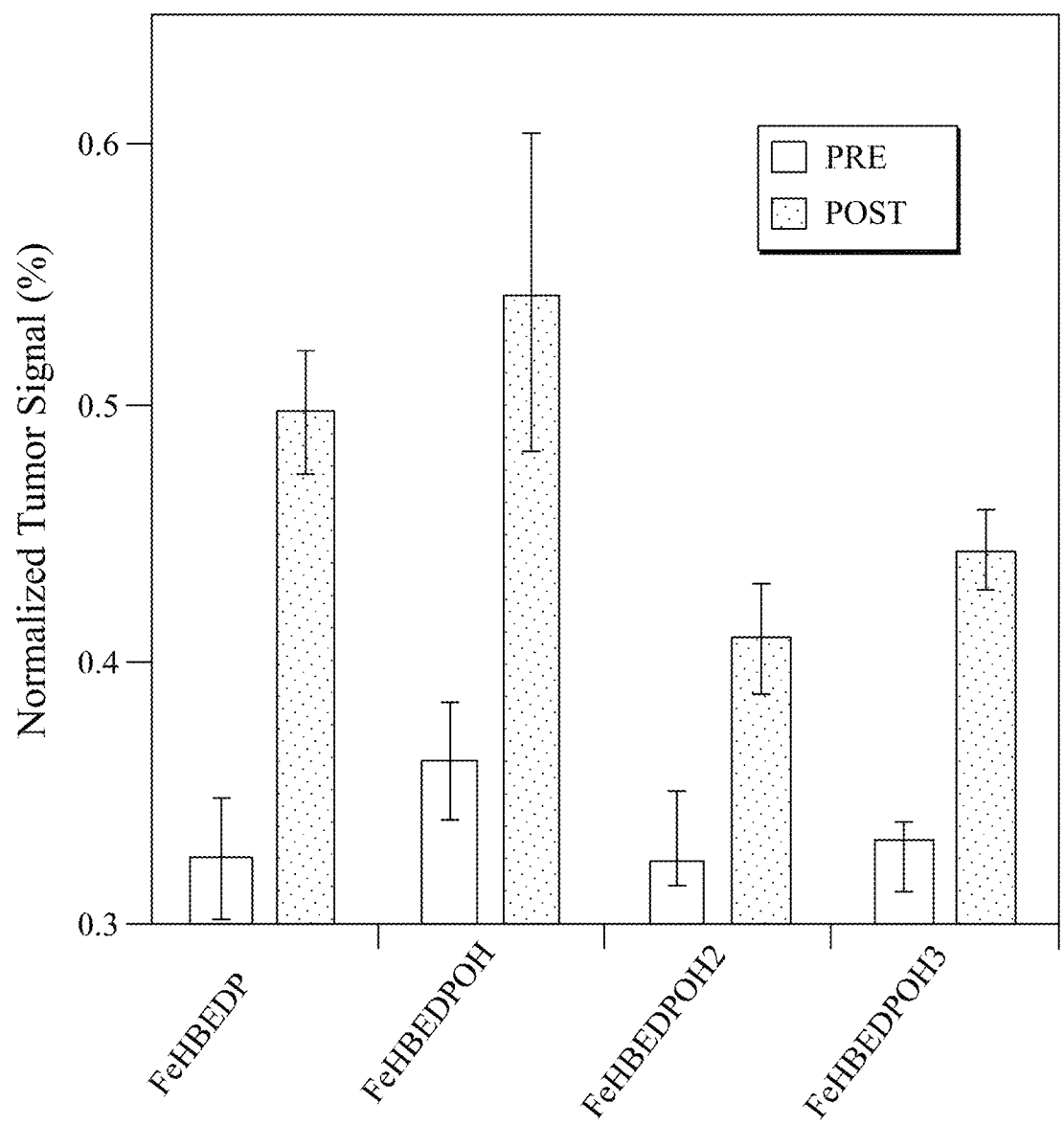
FIG. 5 illustrates tumor image contrast enhancement for a series of contrast enhancement agents in accordance with one or more embodiments of the invention.

FIG. 5 summarizes performance data for individual contrast enhancement agents in the FeHBEDP(OH)$_x$ series in the C6 glioma-bearing mouse model described above. T1 MR signal data before and five minutes post injection of the iron chelate contrast enhancement agent are given. In each case, useful tumor image enhancement is observed. For contrast enhancement agents exhibiting higher protein binding (FeHBEDP and FeHBEDPOH), stronger tumor image enhancement was observed relative to the contrast enhancement agents FeHBEDPOH$_2$ and FeHBEDPOH$_3$ which exhibited relatively lower protein binding efficiency. Thus, the contrast enhancement agents used according to the method of the present invention may be selected to balance protein binding characteristics with image contrast enhancement as needed. The present invention thus provides additional flexibility in the selection of the most suitable contrast enhancement agent depending on the nature of the imaging protocol to be performed.

The foregoing examples are merely illustrative, serving to illustrate only some of the features of the invention. The appended claims are intended to claim the invention as broadly as it has been conceived and the examples herein presented are illustrative of selected embodiments from a manifold of all possible embodiments. Accordingly, it is the Applicants' intention that the appended claims are not to be limited by the choice of examples utilized to illustrate features of the present invention. As used in the claims, the word "comprises" and its grammatical variants logically also subtend and include phrases of varying and differing extent such as for example, but not limited thereto, "consisting essentially of" and "consisting of." Where necessary, ranges have been supplied; those ranges are inclusive of all sub-ranges there between. It is to be expected that variations in these ranges will suggest themselves to a practitioner having ordinary skill in the art and where not already dedicated to the public, those variations should where possible be construed to be covered by the appended claims. It is also anticipated that advances in science and technology will make equivalents and substitutions possible that are not now contemplated by reason of the imprecision of language and these variations should also be construed where possible to be covered by the appended claims.

What is claimed is:
1. A method of diagnostic imaging comprising:
 (a) administering a medical formulation to a subject, the formulation comprising a contrast enhancement agent having structure I and salts thereof

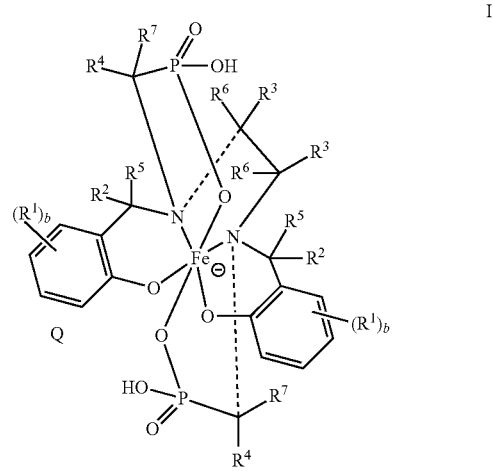

wherein R$^1$ is independently at each occurrence a hydroxy group, a C$_1$-C$_3$ hydroxyalkyl group, or a C$_1$-C$_3$ alkyl group, and b is 0-4; R$^2$-R$^7$ are independently at each occurrence hydrogen, a $C_1$-$C_3$ hydroxyalkyl group, or a $C_1$-$C_3$ alkyl group, with the proviso that at least one of $R^1$-$R^7$ is a hydroxy group or a $C_1$-$C_3$ hydroxyalkyl group; and wherein Q is one or more charge balancing counterions; and one or more pharmaceutically acceptable carriers and excipients; and (b) subjecting the subject to a diagnostic imaging technique.

2. The method according to claim 1, wherein said administering is carried out by injection or ingestion.

3. The method according to claim 1, wherein said administering is carried out by injection.

4. The method according to claim 1, wherein said diagnostic imaging technique is magnetic resonance imaging.

5. The method according to claim 1, wherein said diagnostic imaging technique provides an image of the subject's circulatory system, genitourinary system, hepatobiliary system, central nervous system, tumor, or abscess.

6. The method according to claim 1, wherein the contrast enhancement agent is a racemate, a single enantiomer, an enantiomerically enriched composition, or a mixture of diastereomers.

7. The method according to claim 1, wherein the contrast enhancement agent has structure IV and salts thereof.

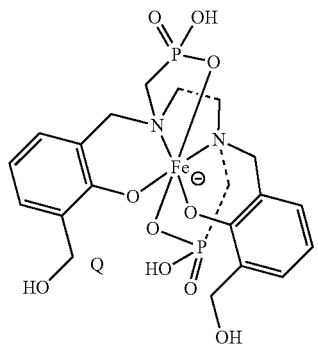

IV wherein Q is one or more charge balancing counterions.

* * * * *